US010865409B2

(12) United States Patent
Keefe et al.

(10) Patent No.: US 10,865,409 B2
(45) Date of Patent: Dec. 15, 2020

(54) METHODS FOR TAGGING DNA-ENCODED LIBRARIES

(75) Inventors: Anthony D. Keefe, Cambridge, MA (US); Richard W. Wagner, Cambridge, MA (US); Alexander Litovchick, Sudbury, MA (US); Matthew Clark, Lexington, MA (US); John W. Cuozzo, Natick, MA (US); Ying Zhang, Lexington, MA (US); Paolo A. Centrella, Acton, MA (US); Christopher D. Hupp, Shrewsbury, MA (US)

(73) Assignee: X-Chem, Inc., Waltham, MA (US)

( * ) Notice: Subject to any disclaimer, the term of this patent is extended or adjusted under 35 U.S.C. 154(b) by 57 days.

(21) Appl. No.: 14/343,306

(22) PCT Filed: Sep. 7, 2012

(86) PCT No.: PCT/US2012/054228
§ 371 (c)(1),
(2), (4) Date: Jun. 20, 2014

(65) Prior Publication Data
US 2014/0315762 A1  Oct. 23, 2014

Related U.S. Application Data

(60) Provisional application No. 61/536,929, filed on Sep. 20, 2011, provisional application No. 61/531,820, filed on Sep. 7, 2011.

(51) Int. Cl.
*C12N 15/10* (2006.01)
*C40B 50/16* (2006.01)

(52) U.S. Cl.
CPC ......... *C12N 15/1065* (2013.01); *C12N 15/10* (2013.01); *C12N 15/1068* (2013.01); *C12N 15/1093* (2013.01); *C40B 50/16* (2013.01); *C07B 2200/11* (2013.01)

(58) Field of Classification Search
None
See application file for complete search history.

(56) References Cited

U.S. PATENT DOCUMENTS

| | | | |
|---|---|---|---|
| 5,013,830 A † | 5/1991 | Ohtsuka | |
| 5,476,930 A | 12/1995 | Letsinger et al. | |
| 5,525,734 A | 6/1996 | Gallop et al. | |
| 5,525,735 A | 6/1996 | Gallop et al. | |
| 5,571,677 A | 11/1996 | Gryaznov | |
| 5,571,903 A | 11/1996 | Gryaznov | |
| 5,573,905 A | 11/1996 | Lerner et al. | |
| 5,585,481 A | 12/1996 | Arnold, Jr. et al. | |
| 5,604,097 A | 2/1997 | Brenner | |
| 5,633,360 A | 5/1997 | Bischofberger et al. | |
| 5,635,400 A | 6/1997 | Brenner | |
| 5,639,603 A | 6/1997 | Dower et al. | |
| 5,654,413 A | 8/1997 | Brenner | |
| 5,656,739 A | 8/1997 | Cubicciotti | |
| 5,670,633 A † | 9/1997 | Cook | |
| 5,681,943 A | 10/1997 | Letsinger et al. | |
| 5,695,934 A | 12/1997 | Brenner | |
| 5,696,251 A | 12/1997 | Arnold, Jr. et al. | |
| 5,708,153 A | 1/1998 | Dower et al. | |
| 5,723,289 A | 3/1998 | Eaton et al. | |
| 5,723,598 A | 3/1998 | Lerner et al. | |
| 5,763,175 A | 6/1998 | Brenner | |
| 5,770,358 A | 6/1998 | Dower et al. | |
| 5,770,367 A | 6/1998 | Southern et al. | |
| 5,770,455 A | 6/1998 | Cargill et al. | |
| 5,780,231 A | 7/1998 | Brenner | |
| 5,780,613 A | 7/1998 | Letsinger et al. | |
| 5,789,162 A | 8/1998 | Dower et al. | |
| 5,807,683 A | 9/1998 | Brenner | |
| 5,840,485 A | 11/1998 | Lebl et al. | |
| 5,846,719 A | 12/1998 | Brenner et al. | |
| 5,846,839 A | 12/1998 | Gallop et al. | |
| 5,863,722 A | 1/1999 | Brenner | |
| 5,888,737 A | 3/1999 | DuBridge et al. | |
| 5,942,609 A | 8/1999 | Hunkapiller et al. | |
| 5,958,691 A | 9/1999 | Pieken et al. | |
| 5,962,228 A | 10/1999 | Brenner | |
| 6,013,445 A | 1/2000 | Albrecht et al. | |
| 6,027,890 A | 2/2000 | Ness et al. | |
| 6,060,596 A | 5/2000 | Lerner et al. | |

(Continued)

FOREIGN PATENT DOCUMENTS

CN       1898257 A     1/2007
CN     101321877 A    12/2008
(Continued)

OTHER PUBLICATIONS

Wang et al.( Nucleic Acids Research, 1995, vol. 23, No. 7 1157-1164). (Year: 1995).*
Lipinski et al., "Experimental and computational approaches to estimate solubility and permeability in drug discovery and development settings," Adv Drug Deliv Rev. 46(1-3):3-26 (2001).
Written Opinion for Singapore Application No. 11201400374T, dated Sep. 18, 2015 (11 pages).
Office Action for Canadian Patent Application No. 2,752,543, dated Nov. 30, 2015 (4 pages).
Extended European Search Report for European Patent Application No. 13816635.0, dated Jan. 5, 2016 (10 pages).
Further Examination Report for New Zealand Patent Application No. 621592, dated Jan. 18, 2016 (2 pages).
Office Action and English translation for Chinese Patent Application No. 201380047930.X, dated Dec. 29, 2015 (13 pages).

(Continued)

*Primary Examiner* — Tracy Vivlemore
*Assistant Examiner* — Sahana S Kaup
(74) *Attorney, Agent, or Firm* — Clark & Elbing LLP

(57) ABSTRACT

The present invention relates to oligonucleotide-encoded libraries and methods of tagging such libraries. In particular, the methods and oligonucleotides can include one or more 2'-substituted nucleotides, such as 2'-O-methyl or 2'-fluoro nucleotides, and other conditions or reagents to enhance enzyme ligation or one or more chemical functionalities to support chemical ligation.

18 Claims, 48 Drawing Sheets

Specification includes a Sequence Listing.

(56) References Cited

U.S. PATENT DOCUMENTS

| | | | |
|---|---|---|---|
| 6,087,112 A † | 7/2000 | Dale | |
| 6,090,912 A | 7/2000 | Lebl et al. | |
| 6,117,976 A | 9/2000 | Neri et al. | |
| 6,140,489 A | 10/2000 | Brenner | |
| 6,140,493 A | 10/2000 | Dower et al. | |
| 6,143,497 A | 11/2000 | Dower et al. | |
| 6,150,516 A | 11/2000 | Brenner et al. | |
| 6,165,717 A | 12/2000 | Dower et al. | |
| 6,172,214 B1 | 1/2001 | Brenner | |
| 6,172,218 B1 | 1/2001 | Brenner | |
| 6,214,553 B1 | 4/2001 | Szostak et al. | |
| 6,218,111 B1 | 4/2001 | Southern et al. | |
| 6,235,475 B1 | 5/2001 | Brenner et al. | |
| 6,281,344 B1 | 8/2001 | Szostak et al. | |
| 6,329,177 B1 * | 12/2001 | Havlina | C07H 21/00 435/6.12 |
| 6,352,828 B1 | 3/2002 | Brenner | |
| 6,368,874 B1 | 4/2002 | Gallop et al. | |
| 6,406,848 B1 | 6/2002 | Bridgham et al. | |
| 6,416,949 B1 | 7/2002 | Dower et al. | |
| 6,479,262 B1 * | 11/2002 | Delagrave | C07H 21/00 424/94.1 |
| 6,503,759 B1 | 1/2003 | Still et al. | |
| 6,537,776 B1 | 3/2003 | Short | |
| 6,537,803 B1 | 3/2003 | Amara et al. | |
| 6,576,426 B2 | 6/2003 | Southern et al. | |
| 6,607,878 B2 | 8/2003 | Sorge | |
| 6,627,748 B1 | 9/2003 | Ju et al. | |
| 6,654,505 B2 | 11/2003 | Bridgham et al. | |
| 6,706,481 B2 | 3/2004 | Rajendran et al. | |
| 6,806,052 B2 | 10/2004 | Bridgham et al. | |
| 6,831,994 B2 | 12/2004 | Bridgham et al. | |
| 6,844,324 B1 | 1/2005 | Zhang et al. | |
| 6,846,655 B1 | 1/2005 | Wagner et al. | |
| 6,867,290 B2 | 3/2005 | Goldsborough | |
| 6,875,736 B2 | 4/2005 | Rana | |
| 6,936,467 B2 * | 8/2005 | Kmiec | C12N 15/102 435/455 |
| 6,936,477 B2 | 8/2005 | Still et al. | |
| 6,994,963 B1 | 2/2006 | Murphy et al. | |
| 7,033,753 B1 | 4/2006 | Kool | |
| RE39,545 E | 4/2007 | Cargill | |
| RE39,571 E | 4/2007 | Cargill | |
| RE39,606 E | 5/2007 | Cargill | |
| 7,217,522 B2 | 5/2007 | Brenner | |
| RE39,793 E | 8/2007 | Brenner | |
| 7,282,370 B2 | 10/2007 | Bridgham et al. | |
| 7,365,179 B2 | 4/2008 | Brenner | |
| 7,393,665 B2 | 7/2008 | Brenner | |
| 7,407,757 B2 | 8/2008 | Brenner | |
| 7,413,536 B1 | 8/2008 | Dower et al. | |
| 7,413,854 B2 | 8/2008 | Pedersen et al. | |
| 7,442,160 B2 | 10/2008 | Liu et al. | |
| 7,479,472 B1 | 1/2009 | Harbury et al. | |
| 7,491,494 B2 | 2/2009 | Liu et al. | |
| 7,537,897 B2 | 5/2009 | Brenner et al. | |
| 7,557,068 B2 | 7/2009 | Liu et al. | |
| 7,704,925 B2 | 4/2010 | Gouliaev et al. | |
| 7,727,713 B2 | 6/2010 | Pedersen et al. | |
| 7,749,699 B2 | 7/2010 | Kool | |
| 7,771,935 B2 | 8/2010 | Liu et al. | |
| 7,915,201 B2 | 3/2011 | Franch et al. | |
| 7,935,658 B2 | 5/2011 | Morgan et al. | |
| 7,972,992 B2 | 7/2011 | Morgan et al. | |
| 7,972,994 B2 | 7/2011 | Morgan et al. | |
| 7,989,395 B2 | 8/2011 | Morgan et al. | |
| 7,998,673 B2 | 8/2011 | French et al. | |
| RE43,097 E | 1/2012 | Albrecht et al. | |
| 8,148,068 B2 | 4/2012 | Brenner | |
| 8,206,901 B2 | 6/2012 | Freskgard et al. | |
| 8,361,713 B2 | 1/2013 | Bridgham et al. | |
| 8,722,583 B2 † | 5/2014 | Gouliaev | |
| 2001/0031475 A1 | 10/2001 | Gallop et al. | |
| 2002/0034732 A1 | 3/2002 | Capon et al. | |
| 2002/0072887 A1 | 6/2002 | Szalma et al. | |
| 2003/0049616 A1 | 3/2003 | Brenner et al. | |
| 2003/0059826 A1 | 3/2003 | Janda et al. | |
| 2003/0119051 A1 | 6/2003 | Wiessler et al. | |
| 2003/0143561 A1 | 7/2003 | Pedersen et al. | |
| 2003/0187240 A1 † | 10/2003 | Cook | |
| 2003/0215846 A1 | 11/2003 | Watt et al. | |
| 2004/0014090 A1 | 1/2004 | Neri et al. | |
| 2004/0049008 A1 | 3/2004 | Pedersen et al. | |
| 2004/0083427 A1 | 4/2004 | Wada | |
| 2004/0259102 A1 | 12/2004 | Kool | |
| 2005/0059049 A1 | 3/2005 | Moen et al. | |
| 2005/0100968 A1 | 5/2005 | Gallop et al. | |
| 2005/0158765 A1 | 7/2005 | Morgan et al. | |
| 2005/0176948 A1 | 8/2005 | Gouliaev et al. | |
| 2005/0221316 A1 | 10/2005 | Pedersen et al. | |
| 2005/0221318 A1 | 10/2005 | Gouliaev et al. | |
| 2005/0227281 A1 | 10/2005 | Liu et al. | |
| 2005/0247001 A1 | 11/2005 | Gouliaev et al. | |
| 2005/0255491 A1 | 11/2005 | Lee et al. | |
| 2006/0099589 A1 | 5/2006 | Pedersen et al. | |
| 2006/0099592 A1 | 5/2006 | Freskgard et al. | |
| 2006/0099626 A1 | 5/2006 | Harbury et al. | |
| 2006/0115829 A1 | 6/2006 | Mao et al. | |
| 2006/0121470 A1 | 6/2006 | Pedersen | |
| 2006/0154246 A1 | 7/2006 | Neri et al. | |
| 2006/0160125 A1 | 7/2006 | Kool | |
| 2006/0166197 A1 | 7/2006 | Gouliaev et al. | |
| 2006/0177833 A1 | 8/2006 | Brenner | |
| 2006/0193869 A1 | 8/2006 | Barrat et al. | |
| 2006/0199192 A1 | 9/2006 | Kool et al. | |
| 2006/0211030 A1 | 9/2006 | Brenner | |
| 2006/0234231 A1 | 10/2006 | Freskgard et al. | |
| 2006/0246450 A1 | 11/2006 | Franch et al. | |
| 2006/0269920 A1 | 11/2006 | Freskgard et al. | |
| 2006/0292603 A1 | 12/2006 | Gouliaev et al. | |
| 2007/0026397 A1 | 2/2007 | Freskgard et al. | |
| 2007/0042401 A1 | 2/2007 | Morgan et al. | |
| 2007/0213519 A1 | 9/2007 | Gouliaev et al. | |
| 2007/0224607 A1 | 9/2007 | Morgan et al. | |
| 2008/0193983 A1 | 8/2008 | Gouliaev et al. | |
| 2008/0220982 A1 | 9/2008 | Vu | |
| 2008/0305957 A1 | 12/2008 | Thisted et al. | |
| 2008/0318802 A1 | 12/2008 | Brenner | |
| 2009/0005256 A1 | 1/2009 | Bittker et al. | |
| 2009/0011957 A1 | 1/2009 | Gouliaev et al. | |
| 2009/0035824 A1 | 2/2009 | Liu et al. | |
| 2009/0062147 A1 | 3/2009 | Morgan et al. | |
| 2009/0143232 A1 | 6/2009 | Pedersen et al. | |
| 2009/0143244 A1 | 6/2009 | Bridgham et al. | |
| 2009/0239211 A1 | 9/2009 | Freskgard et al. | |
| 2009/0239768 A1 | 9/2009 | Hansen et al. | |
| 2009/0264300 A1 | 10/2009 | Franch et al. | |
| 2010/0016177 A1 | 1/2010 | Pedersen et al. | |
| 2010/0094036 A1 | 4/2010 | Hirata et al. | |
| 2010/0159526 A1 * | 6/2010 | Jendrisak | C12N 15/1096 435/91.1 |
| 2010/0184611 A1 | 7/2010 | Neri et al. | |
| 2010/0184661 A1 | 7/2010 | Luo et al. | |
| 2011/0003290 A1 | 1/2011 | Gale et al. | |
| 2011/0104785 A1 * | 5/2011 | Vaidyanathan | C12N 15/10 435/196 |
| 2011/0136697 A1 | 6/2011 | Morgan et al. | |
| 2011/0183863 A1 | 7/2011 | Wagner et al. | |
| 2011/0251089 A1 | 10/2011 | Morgan et al. | |
| 2011/0262898 A1 | 10/2011 | Dong et al. | |
| 2011/0319278 A1 | 12/2011 | Neri et al. | |
| 2012/0004137 A1 | 1/2012 | Wagner et al. | |
| 2012/0053091 A1 | 3/2012 | Wagner | |
| 2012/0071329 A1 | 3/2012 | Morgan et al. | |
| 2012/0107840 A1 | 5/2012 | Wagner et al. | |
| 2012/0245040 A1 | 9/2012 | Morgan et al. | |
| 2013/0046084 A1 | 2/2013 | Brown et al. | |
| 2013/0102545 A1 | 4/2013 | Gao et al. | |
| 2013/0281324 A1 | 10/2013 | Gouliaev et al. | |

FOREIGN PATENT DOCUMENTS

| | | |
|---|---|---|
| CN | 102317513 A | 1/2012 |
| DE | 19646372 C1 | 6/1997 |

(56) References Cited

FOREIGN PATENT DOCUMENTS

| | | |
|---|---|---|
| DE | 19642751 A1 | 4/1998 |
| EP | 1533385 A1 | 5/2005 |
| EP | 1423400 B1 | 8/2006 |
| EP | 1905829 A2 | 4/2008 |
| EP | 1828381 B1 | 1/2009 |
| EP | 2175019 A2 | 4/2010 |
| EP | 2186897 A1 | 5/2010 |
| EP | 2236606 A2 | 10/2010 |
| EP | 1957644 B1 | 12/2010 |
| EP | 2258870 A2 | 12/2010 |
| EP | 2305808 A1 | 4/2011 |
| EP | 2311786 A2 | 4/2011 |
| EP | 1558744 B1 | 6/2011 |
| EP | 2336315 A2 | 6/2011 |
| EP | 2338990 A2 | 6/2011 |
| EP | 2341140 A1 | 7/2011 |
| EP | 2348124 A2 | 7/2011 |
| EP | 2348125 A2 | 7/2011 |
| EP | 2216338 B1 | 3/2013 |
| EP | 2272856 B1 | 11/2015 |
| GB | 94922966 | 7/1993 |
| JP | 5292967 A | 11/1993 |
| JP | 8000268 A | 1/1996 |
| JP | 2002315577 A | 10/2002 |
| JP | 2007-529994 A | 11/2007 |
| WO | WO-92/22875 A1 | 12/1992 |
| WO | WO-93/06121 A1 | 4/1993 |
| WO | WO-93/20242 A1 | 10/1993 |
| WO | WO-94/08051 A1 | 4/1994 |
| WO | WO-95/04160 A1 | 2/1995 |
| WO | WO-95/06293 A1 | 3/1995 |
| WO | WO-95/12608 A1 | 5/1995 |
| WO | WO-96/35699 A1 | 11/1996 |
| WO | WO-96/38726 A1 | 12/1996 |
| WO | WO-97/32999 A1 | 9/1997 |
| WO | WO-98/31700 A1 | 7/1998 |
| WO | WO-99/10485 A1 | 3/1999 |
| WO | WO-99/18240 A2 | 4/1999 |
| WO | WO-00/20639 A1 | 4/2000 |
| WO | WO-00/23458 A1 | 4/2000 |
| WO | WO-00/32823 A1 | 6/2000 |
| WO | WO-00/61775 A1 | 10/2000 |
| WO | WO-01/16352 A1 | 3/2001 |
| WO | WO-02/40664 A1 | 5/2002 |
| WO | WO-02/074929 A2 | 9/2002 |
| WO | WO-02/102820 A1 | 12/2002 |
| WO | WO-02/103008 A2 | 12/2002 |
| WO | WO-03/078050 A2 | 9/2003 |
| WO | WO-03/078445 A2 | 9/2003 |
| WO | WO-03/078446 A2 | 9/2003 |
| WO | WO-03/078625 A2 | 9/2003 |
| WO | WO-03/078626 A2 | 9/2003 |
| WO | WO-03/078627 A2 | 9/2003 |
| WO | WO-2004/001042 A2 | 12/2003 |
| WO | WO-2004/009814 A1 | 1/2004 |
| WO | WO-2004/013070 A2 | 2/2004 |
| WO | WO-2004/016767 A2 | 2/2004 |
| WO | WO-2004/024929 A2 | 3/2004 |
| WO | 2004039825 † | 5/2004 |
| WO | WO-2004/039825 A2 | 5/2004 |
| WO | WO-2004/056994 A2 | 7/2004 |
| WO | WO-2004/074429 A2 | 9/2004 |
| WO | WO-2004/074501 A2 | 9/2004 |
| WO | WO-2004/083427 A2 | 9/2004 |
| WO | WO-2005/008240 A2 | 1/2005 |
| WO | WO-2005/026387 A1 | 3/2005 |
| WO | WO-2005/058479 A2 | 6/2005 |
| WO | WO-2005/078122 A2 | 8/2005 |
| WO | WO-2005/090566 A2 | 9/2005 |
| WO | WO-2006/048025 A1 | 5/2006 |
| WO | WO-2006/053571 A2 | 5/2006 |
| WO | WO-2006/079061 A2 | 7/2006 |
| WO | WO-2006/135786 A2 | 12/2006 |
| WO | WO-2007/041201 A2 | 4/2007 |
| WO | WO-2007/053358 A2 | 5/2007 |
| WO | WO-2007/062664 A2 | 6/2007 |
| WO | WO007062664 * | 6/2007 |
| WO | WO-2009/066447 A1 | 5/2009 |
| WO | WO-2009/077173 A2 | 6/2009 |
| WO | WO-2009/152824 A1 | 12/2009 |
| WO | WO-2010/086602 A1 | 8/2010 |
| WO | WO-2010/094027 A1 | 8/2010 |
| WO | WO-2010/094036 A1 | 8/2010 |
| WO | WO-2010/094040 A1 | 8/2010 |
| WO | WO2010094036 * | 8/2010 |
| WO | WO-2011/120042 A1 | 9/2011 |
| WO | WO-2012/125733 A2 | 9/2012 |
| WO | WO-2013/036810 A1 | 3/2013 |
| WO | WO-2014/012010 A1 | 1/2014 |
| WO | WO-2015/091207 A1 | 6/2015 |

OTHER PUBLICATIONS

Third-Party Observation pursuant to Art. 115 EPC for European Patent Application No. 10741877, filed Mar. 14, 2016 (38 pages).
Mullah et al., "Efficient synthesis of double dye-labeled oligodeoxyribonucleotide probes and their application in a real time PCR assay," Nucleic Acids Res. 26(4):1026-031 (1998).
Thelwell et al., "Mode of action and application of Scorpion primers to mutation detection," Nucleic Acids Res. 28(19):3752-61 (2000).
Wagner, "Gene inhibition using antisense oligodeoxynucleotides," Nature. 372:333-5 (1994).
Wagner et al., "Antisense gene inhibition by oligonucleotides containing C-5 propyne pyrimidines," Science. 260:1510-3 (1993).
Yamana et al., "Synthesis and binding properties of oligonucleotides containing an azobenzene linker," Nucleosides and Nucleotides. 17(1-3):233-42 (1998).
Communication pursuant to Article 94(3) EPC for European Patent Application No. 10741877.4, dated Mar. 24, 2016 (6 pages).
Anonymous, "PDC-CE Phosphoramidite," Glen Research Report of Products for RNA and DNA Oligonucleotide Synthesis. (2004) (3 pages).
Anonymous, "PDU-CE Phosphoramidite," Glen Research Report of Products for RNA and DNA Oligonucleotide Synthesis. (2004) (3 pages).
Anonymous, "5-F-DU-CE Phosphoramidite," Glen Research Report of Products for RNA and DNA Oligonucleotide Synthesis. (2004) (3 pages).
Anonymous, "Versatile New Reagents: Pyrene-dU and Perylene-dU," Glen Research Report of Products for RNA and DNA Oligonucleotide Synthesis. (2008) (2 pages).
Korshun et al., "5-(1-pyrenylethynyl)-2'-deoxyuridine, a novel fluorescent nucleoside analog," Bioorg Khim. 22:923-5 (1996).
Examination Report for Australian Patent Application No. 2012304387, dated Feb. 23, 2016 (3 pages).
Zietlow et al., "DNA polymerase I-mediated translesion synthesis in RecA-independent DNA interstrand cross-link repair in E. coli," Biochemistry. 47(19):5460-4 (2008).
Office Action and English Translation for Japanese Patent Application No. 2014-529907, dated Jun. 20, 2016 (6 pages).
Communication pursuant to Article 94(3) EPC for European Patent Application No. 12830083.7, dated Aug. 4, 2016 (4 pages).
Communication pursuant to Rule 114(2) EPC for European Patent Application No. 10741877.4, dated Oct. 7, 2016 (29 pages).
First Examination Report for New Zealand Patent Application No. 722289, dated Aug. 3, 2016 (2 pages).
International Preliminary Report on Patentability for International Patent Application No. PCT/US2012/054228, dated Mar. 12, 2014 (6 pages).
Office Action for Chinese Patent Application No. 2012800539302, dated Jan. 28, 2015 (14 pages).
Search Report and Written Opinion for Singaporean Application No. 11201400374T, completed Jan. 5, 2015 (19 pages).
Supplementary European Search Report for European Patent Application No. 12830083.7, dated Mar. 13, 2015 (8 pages).
Abe et al., "Structure analysis of oligonucleotide in organic solvent," Nucleic Acids Symposium Series. 50: 25-26 (2006).

(56) References Cited

OTHER PUBLICATIONS

Amato, "Speeding up a chemical game of chance," Science. 257: 330-331 (1992).
Anonymous, "Non-enzymatic ligation of single-stranded and duplex DNA," Glen Research Report of Products for RNA and DNA Oligonucleotide Synthesis. 10 (1997).
Author manuscript of Didenko et al., "Substantial Background Reduction in Ligase-based Apoptosis Detection Using Newly Designed Hairpin Oligoprobes," available in PMC Jun. 18, 2007, published in final edited form as: Biotechniques. 27: 1130-1132 (1999) (5 pages).
Balanov et al., "Development of DNA-encoded library containing $10^9$ backbone cyclic peptides on 7μM glass beads," Peptides Frontiers of Peptide Science, American Peptide Symposia. 5: 49-50 (2002).
Bartel et al., "Isolation of new ribozymes from a large pod of random sequences," Science. 261: 1411-1418 (1993).
Berezovski et al., "Non-SELEX: selection of aptamers without intermediate amplification of candidate oligonucleotides," Nature Protocols. 1: 1359-1369 (2006).
Brenner et al., "Encoded combinatorial chemistry," Proc Natl Acad Sci USA. 89: 5381-5383 (1992).
Brenner et al., "Gene expression analysis by massively parallel signature sequencing (MPSS) on microbead arrays," Nature Biotechnology. 18: 630-634 (2000).
Brenner et al., "In vitro cloning of complex mixtures of DNA on microbeads: physical separation of differentially expressed cDNAs," Proc Natl Acad Sci USA. 97: 1665-1670 (2000).
Bruick et al., "Template-directed ligation of peptides to oligonucleotides," Chemistry & Biology. 3: 49-56 (1996).
Cherepanov et al., "Scanning mutagenesis using T4 DNA ligase and short degenerate DNA oligonucleotides containing tri-nucleotide mismatches," available on http://wwwsoc.nii.ac.jp/jpbiochem/b/132-1/1fcafttx.htm Apr. 2, 2002, published in final edited form as: J. Biochem. 132:143-147 (2002) (6 pages).
Chiu et al., "Visualizing a correlation between siRNA localization, cellular uptake, and RNAi in living cells," Chemistry & Biology. 11: 1165-1175 (2004).
Clark et al., "Design, synthesis and selection of DNA-encoded small-molecule libraries," Nature Chemical Biology 5: 647-654 (2009).
Ekland et al., "Structurally complex, and highly active RNA ligases derived from random RNA sequences," Science 269: 364-370 (1995).
File History for European Patent Application No. 03757752.5 (1,559 pages).
File History for U.S. Appl. No. 10/525,817 (735 pages).
Gartner and Liu, "The Generality of DNA-Templated Synthesis as a Basis for Evolving Non-Natural Small Molecules," J. Am. Chem. Soc. 123: 6961-6963 (2001).
Goodwin and Lynn, "Template-directed Synthesis: Use of a Reversible Reaction," J. Am. Chem. Soc. 114: 9197-9198 (1992).
Géron-Landre et al., "Sequence-specific fluorescent labeling of double-stranded DNA observed at the single molecule level," Nucl. Acids Res. 31: e125 (2003) (8 pages).
Halpin and Harbury, "DNA Display I. Sequence-Encoded Routing of DNA Populations," PLoS Biology 2: 1015-1021 (2004).
Halpin and Harbury, "DNA Display II. Genetic Manipulation of Combinatorial Chemistry Libraries for Small-Molecule Evolution," PLoS Biology 2: 1022-1030 (2004).
Harada and Orgel, "In vitro selection of optimal DNA substrates for T4 RNA ligase," Proc. Natl. Acad. Sci. USA 90: 1576-1579 (1993).
Herrlein et al., "A Covalent Lock for Self-Assembled Oligonucieotide Conjugates," J. Am. Chem. Soc. 117: 10151-10152 (1995).
International Search Report and Written Opinion for International Patent Application No. PCT/US2012/054228, dated Jan. 7, 2013 (9 pages).
Ito et al., "Modification of lipase with various synthetic polymers and their catalytic activities in organic solvent," Biotechnology Progress 10: 398-402 (1994).

Janda, "Tagged versus untagged libraries: Methods for the generation and screening of combinatorial chemical libraries," Proc Natl Acad Sci USA. 91: 10779-10785 (1994).
Jarosch et al., "In vitro selection using a dual RNA library that allows primerless selection," Nucleic Acids Research 34: e86 (2006) (9 pages).
Jenne and Famulok, "A novel ribozyme with ester transferase activity," Chem. Biol. 5: 23-34 (1998).
Jäschke et al., "Synthesis and properties of oligodeoxyribonucleotide-polyethylene glycol conjugates," Nucleic Acids Research 22: 4810-4817 (1994).
Kempe et al., "Chemical and enzymatic biotin-labeling of oligodeoxyribonucleotides," Nucleic Acids Research 13: 45-57 (1985).
Kinoshita and Nishigaki, "Enzymatic syntheis of code regions for encoded combinatorial chemistry," Nucleic Acids Symposium Series 34: 201-202 (1995).
Kinoshita et al., "Enzymatic synthesis of sequencing primers based on a library of tetramers," Chemistry Express 7: 149-152 (1992).
Kinoshita et al., "Strand Ligation in a Double-stranded DNA by T4 RNA Ligase," Chemistry Letters 9: 797-798 (1996).
Kitamura et al., "Construction of block-shuffled libraries of DNA for evolutionary protein engineering: Y-ligation-based block shuffling," Protein Engineering 15: 843-853 (2002).
Kitamura et al., "Development of systemic in vitro evolution and its application to generation of peptide-aptamer-based inhibitors of cathepsin E," J. Mol. Biol. 387: 1186-1198 (2009).
Lebl, "Parallel Personal Comments on "Classical" Papers in Combinatorial Chemistry,"J. Comb. Chem. 1: 3-24 (1999).
Lee et al., "Ribozyme-catalyzed tRNA aminoacylation," Nature Struct. Biol. 7: 28-33 (2000).
Li and Breaker, "Kinetics of RNA degradation by specific base catalysis of transesterification involving the 2'-hydroxyl group," J. Am. Chem. Soc. 121: 5364-5372 (1999).
Liu, "Development of Amplifiable and Evolvable Unnatural Molecules," website of Dr. D. R. Liu, publicly available Mar. 11, 2000. http://web.archive.ora/web/20000311112631/http://evolve.havard.edu (2 pages).
Liu, "The Chemistry and Chemical Biology of Molecular Evolution," website of Dr. D.R. Liu, publicly available Mar. 1, 2001. http://web.archive.org/web/20010301175107/http://evolve.havard edu (2 pages).
Liu, "The Chemistry of Molecular Evolution," website of Dr. D.R. Liu, publicly available Oct. 15, 2000. http://web.archive.ora/web/20001015144553/http://evolve.havard.edu (3 pages).
Morpurgo et al., "An approach to increased polyplex gene delivery by peptides selected from a phage display library," J. Biochem. Biophys. Methods 52: 31-43 (2002).
Needels et al., "Generation and screening of an oligonucleotide-encoded synthetic peptide library," Proc. Nati. Acad. Sci. USA 90: 10700-10704 (1993).
Nielsen and Janda, "Toward Chemical Implementation of Encoded Combinatorial Libraries," Methods 6: 361-371 (1994).
Nielsen et al., "Synthetic Methods for the Implementation of Encoded Combinatorial Chemistry," J. Am. Chem. Soc. 115: 9812-9813 (1993).
Nishigaki et al., "T4 RNA Ligase: Its potential and applications to molecular biotechnology," Symp Biofunc Chem. 13:394-6 (1998) (English Translation included, 2 pages) (5 pages).
Nishigaki et al., "Y-ligation: An efficient method for ligating single-stranded DNAs and RNAs with T4 RNA ligase," Molecular Diversity 4: 187-190 (1998).
Nishigaki, "RNA Ligases," Encyclopedia of Molecular Biology (2002) (3 pages).
Pochet et al., "Solid-Supported Ligation Primer," Nucleic Acids Research 16: 1619 (1988).
Roberts and Szostak, "RNA-peptide fusions for the in vitro selection of peptides and proteins," Proc. Natl. Acad. Sci. USA 94: 12297-12302 (1997).
Rohatgi et al., "Kinetic and Mechanistic Analysis of Nonenzymatic, Template-Directed Oligoribonucleotide Ligation," J. Am. Chem. Soc. 118: 3332-3339 (1996).

(56) References Cited

OTHER PUBLICATIONS

Rohatgi et al., "Nonenzymatic, Template-Directed Ligation of Oligoribonucleotides is Highly Regioselective for the Formation of 3'-5' Phosphodiester Bonds," *J. Am. Chem. Soc.* 118: 3340-3344 (1996).
Rozenman and Liu, "DNA-Templated Synthesis in Organic Solvents," *ChemBioChem* 7: 253-256 (2006).
Scheuermann et al., "DNA-encoded chemical libraries," *Journal of Biotechnology* 126: 568-581 (2006).
Schmidt et al., "Information transfer from DNA to peptide nucleic acids by template-directed syntheses," *Nucl. Acids Res.* 25: 4792-4796 (1997).
Schmitz and Reetz, "Solid-phase Enzymatic Synthesis of Oligonucleotides," *Org. Lett.* 1: 1729-1731 (1999).
Stryer, Eukaryotic Chromosomes and Gene Expression. *Biochemistry*, W.H. Freeman and Company: New York, 4th ed., 975-988 (1995).
Suga et al., "Structural and Kinetic Characterization of an Acyl Transferase Ribozyme," *J. Am. Chem. Soc.* 120: 1151-1156 (1998).
Suga et al., "Unusual Metal Ion Catalysis in an Acyl-Tranferase Ribozyme," *Biochem.* 37: 10118-10125 (1998).
Summerer and Marx, "DNA-Templated Synthesis: More Versatile than Expected," *Angew. Chem. Int. Ed.* 41: 89-90 (2002).
Supplementary Methods for Clark et al., "Design, Synthesis and selection of DNA-encoded small molecule libraries," *Nature Chemical Biology* 5: 1-57 (2009).
Tabuchi et al., "An Efficient Ligation Method in the Making of an in vitro Virus for in vitro Protein Evolution," *Biol. Proced. Online* 4: 49-54 (2002).
Tamura and Schimmel, "Oligonucleotide-directed peptide synthesis in a ribosome- and ribozyme-free system," *Proc. Natl. Acad. Sci. USA* 98: 1393-1397 (2001).
Tessier et al., "Ligation of Single Stranded Oligodeoxyribonucleotides by T4 RNA Ligase," *Analytical Biochemistry* 158: 171-178 (1986).
Visscher and Schwartz, "Template-directed synthesis of acyclic oligonucleotide analogues," *J. Mol. Evol.* 28: 3-6 (1988).
Walder et al., "Complementary carrier peptide synthesis: general strategy and implications for prebiotic origin of peptide synthesis," *Proc. Nat. Acad. Sci. USA* 76: 51-55 (1979).
Xu and Kool, "Chemical and enzymatic properties of bridging 5'-S-phosphorothioester linkages in DNA," *Nucl. Acids Res.* 26: 3159-3164 (1998).
Xu and Kool, "High sequence fidelity in a non-enzymatic DNA autoligation reaction," *Nucl. Acids Res.* 27:875-881 (1999).
Yoshimura and Fujimoto, "Ultrafast Reversible Photo-Cross-Linking Reaction: Toward in Situ DNA Manipulation," *Org. Lett.* 10: 3227-3230 (2008).
Zhang and Chiang, "Single-stranded DNA ligation by T4 RNA ligase for PCR cloning of 5'-noncoding fragments and coding sequence of a specific gene," *Nucleic Acids Research* 24(5): 990-991 (1996).
Liang et al., "A supra-photoswitch involving sandwiched DNA base pairs and azobenzenes for light-driven nanostructures and nanodevices," *Small.* 5(15):1761-8 (2009).
Third-Party Observation pursuant to Art. 115 EPC for European Patent Application No. 10741877, dated Feb. 16, 2017 (28 pages).
Office Action and English Translation for Japanese Patent Application No. 2014-529907, dated Mar. 15, 2017 (8 pages).
Examination Report No. 2 for Australian Patent Application No. 2012304387, dated Feb. 1, 2017 (3 pages).
Notification of Material filed by a Third Party for Australian Patent Application No. 2012304387, dated Feb. 16, 2017 (44 pages).
Communication pursuant to Article 94(3) EPC for European Patent Application No. 12830083.7, dated Dec. 16, 2016 (4 pages).
Notification of Third-Party Submission of Information and English Translation for Japanese Patent Application No. 2014-529907, dated Jan. 16, 2017 (2 pages).
Third-Party Observation pursuant to Art. 115 EPC for European Patent Application No. 13816635, dated Apr. 28, 2017 (68 pages).
Third-Party Observation pursuant to Art. 115 EPC for European Patent Application No. 12830083, dated May 3, 2017 (9 pages).
Jinfeng et al., "Gene Analysis and Biochip Technique," compiled mainly by Ding, Hubei Science and Technology Press, p. 108-109 (2004) (3 pages).
"Pharmacology Frontier—Signal, Protein factor, Gene and Modern Pharmacology", compiled mainly by Wei Erqing, Science and Technology Press, p. 314-316 (1999) (4 pages).
Blondal et al., "Isolation and characterization of a thermostable RNA ligase 1 from a Thermus scotoductus bacteriophage TS2126 with good single-stranded DNA ligation properties," Nucleic Acids Res. 33(1):135-42 (2005).
Cummins et al., "Characterization of fully 2'-modified oligoribonucleotide hetero- and homoduplex hybridization and nuclease sensitivity," Nucleic Acids Res. 23(11):2019-24 (1995).
Sastry et al., "Cross-linking of DNA-binding proteins to DNA with psoralen and psoralen furan-side monoadducts. Comparison of action spectra with DNA-DNA cross-linking," J Biol Chem. 272(6):3715-23 (1997).
Third-Party Observation pursuant to Art. 115 EPC for European Patent Application No. 12830083, dated Dec. 8, 2016 (51 pages).
Uhlenbeck et al., "2. T4 RNA Ligase," The Enzymes. 15:31-58 (1982).
Third-Party Observation pursuant to Art. 115 EPC for European Patent Application No. 12830083, dated Oct. 9, 2017 (13 pages).
Hoepfner et al., "Amplified primer extension assay for psoralen photoproducts provides a sensitive assay for a (CG)6TA(CG)2(TG)8 Z-DNA torsionally tuned probe: preferential psoralen photobinding to one strand of a B-Z junction," Biochemistry 32(29):7542-8 (1993).
Tornaletti et al., "Transcription arrest at an abasic site in the transcribed strand of template DNA," Chem Res Toxicol. 19(9):1215-20 (2006).
Dimitri et al., "Transcription elongation past O6-methylguanine by human RNA polymerase II and bacteriophage T7 RNA polymerase," Nucleic Acids Res. 36(20):6459-71 (2008).
Engelhart et al., "Nonenzymatic ligation of DNA with a reversible step and a final linkage that can be used in PCR," Chembiochem. 13(8):1121-4 (2012).
Third-Party Observation pursuant to Art. 115 EPC for European Patent Application No. 12830083, filed May 3, 2017 (9 pages).
Paredes et al., "Click chemistry for rapid labeling and ligation of RNA," ChemBIoChem 12:125-31 (2011).
El-Sagheer et al., "Click nucleic acid ligation: applications in biology and nanotechnology," Acc Chem Res. 45(8):1258-67 (2012).
Office Action for Eurasian Patent Application No. 201490534, dated Jun. 21, 2017 (2 pages).
Office Action for Canadian Application No. 2,848,023, dated May 11, 2018 (6 pages).
Asanuma et al., "Photocontrol of DNA duplex formation by using azobenzene-bearing oligonucleotides," Chembiochem. 2(1):39-44 (2001).
Beaucage et al., "The functionalization of oligonucleotides via phosphoramidite derivatives," Tetrahedron 49(10):1925-63 (1993).
Bonora et al., "Synthesis and characterization of high-molecular mass polyethylene glycol-conjugated oligonucleotides," Bioconjug Chem. 8(6):793-7 (1997).
Cui, "Have the primary structures of biomacromolecules been selected in a Darwinian fashion to adapt to the surrounding environments of our planet?," IUBMB Life 61(8):860-3 (2009).
Decision of Rejection for Japanese Application No. 2014-529907, dated Jan. 9, 2018 (10 pages).
Efimov et al., "Cross-linked nucleic acids: formation, structure, and biological function," Russ J Bioorg Chem. 36(1):49-72 (2010).
Examination Report for African Patent Application No. AP/P/2014/007483, dated Oct. 27, 2016 (4 pages).
Examination Report for Australian Application No. 2017201146, dated Feb. 19, 2018 (3 pages).
Glen Research Information and MSDS for 5'-Dimethoxytrityl-5-[N-(trifluoroacetylaminohexyl)-3-acrylimido]-2'-deoxyUridine,3'-[(2-cyanoethyl)-(N,N-diisopropyl)]-phosphoramidite (Catalogue No. 10-1039-xx from Apr. 14, 2005 and Aug. 19, 2004), available at: https://web.archive.org/web/20050414005644/http://www.glenresearch.

(56) References Cited

OTHER PUBLICATIONS com/ProductFiles/10-1039.html ; https://web.archive.org/web/20040819072021/http://www.glenresearch.com/ProductFiles/MSDS/m10-1039.html (4 pages.)
Glen Research Information and MSDS for 5-F-dU-CE Phosphoramidite (Catalogue No. 10-1092-xx from Oct. 28, 2004 and Apr. 28, 2005), available at: https://web.archive.org/web/20050428232151/http://www.glenresearch.com/ProductFiles/10-1092.html; https://web.archive.org/web/20041028091346/http://www.glenresearch.com/ProductFiles/MSDS/m10-1092.html (4 pages.)
Glen Research Information and MSDS for pdC-CE Phosphoramidite (Catalogue No. 10-1014-xx from Sep. 1, 2004 and Mar. 8, 2005), available at: https://web.archive.org/web/20050308232245/http://www.glenresearch.com:80/ProductFiles/10-1014.html; https://web.archive.org/web/20040901150244/http://www.glenresearch.com/ProductFiles/MSDS/m10-1014.html (4 pages).
Glen Research Information and MSDS for pdU-CE Phosphoramidite (Catalogue No. 10-1054-xx from Oct. 28, 2004 and Mar. 8, 2005), available at: https://web.archive.org/web/20050308232237/http://www.glenresearch.com/ProductFiles/10-1054.html; https://web.archi ve.org/web/20041028103548/http://www.glenresearch.com/ProductFiles/MSDS/m10-1054.html (3 pages).
Glen Research Information for Pyrene-dU-CE Phosphoramidite (Catalogue No. 10-1590-xx from Aug. 21, 2008 and Dec. 2, 2008), available at: https://web.archive.org/web/20081202060550/http://www.glenresearch.com/Catalog/structural.html#a101590; https://web.archive.org/web/20080821194747/http://www.glenresearch.com/GlenReports/GR19-28.html (9 pages).
Integrated DNA Technologies, Inc. for "Int Spacer 9" (iSp9—Product No. 1391 from Oct. 16, 2006 and Nov. 9, 2006) available at <https://web.archive.org/web/20071109184957/http://www.idtdna.com:80/Catalog/Modifications/RNAModifications.aspx https://web.archive.org/web/20061016193020/https://www.idtdna.com/catalog/Modifications/Modifications.aspx?ProductID-1391> (2 pages).
Integrated DNA Technologies, Inc. for "Int Uni-Link™ Amino Modifier" (iUniAmM—Product No. 1440 from Oct. 16, 2006 and Nov. 15, 2006) available at <https://web.archive.org/web/20061115041630/http://www.idtdna.com:80/Catalog/Modifications/RNAModifications.aspxhttps://web.archive.org/web/20061016184659/https://www.idtdna.com/Catalog/Modifications/Modifications.aspx?ProductID-1440> (2 pages).
Jäschke, Chapter 18: Oligonucleotide-Poly(ethylene glycol) Conjugates: Synthesis, Properties, and Applications. *ACS Symposium Series*, p. 265-83 (1997).
Lewis et al., "Synthesis, structure, and photochemistry of exceptionally stable synthetic DNA hairpins with stilbene diether linkers," J Am Chem Soc. 124(41):12165-73 (2002).
Malakhov et al., "Synthesis and fluorescent properties of 5-(1-pyrenylethynyl)-2'-deoxyuridine-containing oligodeoxynucleotides," Russ J Bioorg Chem. 26(1):34-44 (2000).
Notice of Preliminary Rejection for Korean Patent Application No. 10-2017-7029869, dated Feb. 15, 2018 (10 pages).
Polyethylene Glycols. Prepared at the 31st JECFA (1987), published in 1988 in FAO Food and Nutrition Paper 38 (FNP 38), and in 1992 in vol. 3 of "Compendium of Food Additive Specifications" (FNP 52) (11 pages).
Ren et al., "Formation of Stable DNA Loops by Incorporation of Nonpolar, Non-Hydrogen-Bonding Nucleoside Isosteres," Available in PMC Sep. 27, 2010, published in final edited form as: Angew Chem Int Ed Engl. 35(7):743-6 (1996) (8 pages).
Salunkhe et al., "Control of folding and binding of oligonucleotides by use of a nonnucleotide linker," J Am Chem Soc. 114(23):8768-72 (1992).
Supporting information for Rozenman and Liu, ChemBioChem, pp. S1-S18 (2006).
Wang et al., "A thermostable azo-linker for reversible photoregulation of DNA replication," Tetrahedron Letters 49(34):5087-9 (2008).
Wu et al., "Reversible stability switching of a hairpin DNA via a photo-responsive linker unit," Chem Commun (Camb). 14(14):1915-7 (2009).

Yamana et al., "Synthesis of oligonucleotides containing a new azobenzene fragment with efficient photoisomerizability," Bioorg Med Chem. 7(12):2977-83 (1999).
Preliminary Search Report for European Patent Application No. 18158771.8, dated Apr. 10, 2018 (21 pages).
Decision of Rejection and English Translation for Chinese Application No. 201280053930.2, dated Jan. 29, 2018 (11 pages).
English Translation of Office Action for Israeli Application No. 231191, dated Feb. 20, 2018 (3 pages).
Extended European Search Report for European Application No. 18158771.8, dated Jul. 26, 2018 (18 pages).
Further Examination Report for New Zealand Patent Application No. 722289, dated Nov. 27, 2017 (2 pages).
First Examination Report for New Zealand Patent Application No. 736922, dated Nov. 27, 2017 (4 pages).
Examination Report for Indian Patent Application No. 2574/CHENP/2014, dated Apr. 11, 2019 (6 pages).
Asanuma et al., "Synthesis of azobenzene-tethered DNA for reversible photo-regulation of DNA functions: hybridization and transcription," Protocol. 2(1):203-212 (2007) (11 pages).
Berger et al., "Chemistry on nucleic acid templates," *Chem Biodivers.* 7(10):2581-615 (2010).
Chapter 5: Crosslinking and Photoactivatable Reagents. *Molecular Probes Handbook: A Guide to Fluorescent Probes and Labeling Technologies, 11th Edition.* ThermoFischer Scientific. (2010) (18 pages).
Clark et al., Supplementary Methods for "Design, synthesis and selection of DNA-encoded small-molecule libraries," Nat Chem Biol. 5(9):647-54 (2009) (57 pages).
Communication of Opposition to European Patent No. 2,748,357, dated Jan. 4, 2019 (42 Pages).
El-Sagheer et al., "Efficient RNA synthesis by in vitro transcription of a triazole-modified DNA template," Chem Commun (Camb). 47(44):12057-8 (2011).
Fujimoto et al., "A light-controlled reversible DNA photoligation via carbazole-tethered 5-carboxyvinyluracil," Org Lett. 10(3):397-400 (2008).
Jinfeng Ding et al., "Gene analysis and Bio-chip technology," Wuhan: Hubei Science and Technology Press. (2004) (5 pages).
Kanaya et al., "Template-Directed Polymerization of Oligoadenylates Using Cyanogen Bromide," Biochemistry. 25(23):7423-30 (1986).
Kleiner et al., "In Vitro Selection of a DNA-Templated Small-Molecule Library Reveals a Class of Macrocyclic Kinase Inhibitors," J Am Chem Soc. 132(33):11779-11791 (2010).
Kocalka et al., "Rapid and Efficient DNA Strand Cross-Linking by Click Chemistry," Chembiochem. 9(8):1280-5 (2008).
Kore et al., "Efficient synthesis of 3-cyanovinylcarbazole-1'-beta-deoxyriboside-5'-triphosphate: a reversible photo-cross-linking probe," Tetrahedron Lett. 53(31):4012-14 (2012).
Leggett et al., "NextClip: an analysis and read preparation tool for Nextera Long Mate Pair libraries," Bioinformatics 30(4):566-8 (2014).
Li et al., "DNA-templated organic synthesis: nature's strategy for controlling chemical reactivity applied to synthetic molecules," Angew Chem Int Ed Engl. 43(37):4848-70 (2004).
Litovchick et al., "Encoded Library Synthesis Using Chemical Ligation and the Discovery of sEH Inhibitors from a 334-Million Member Library," Sci Rep. 5:10916 (2015) (8 pages).
Litovchick et al., "Universal strategies for the DNA-encoding of libraries of small molecules using the chemical ligation of oligonucleotide tags," Artif DNA PNA XNA. 5(1):e27896 (2014) (11 pages).
Luebke et al., "Nonenzymatic ligation of double-helical DNA by alternate-strand triple helix formation," Nucleic Acids Res. 20(12):3005-9 (1992).
Nakamura et al., "Template directed reversible photochemical ligation of oligodeoxynucleotides," Molecules 17(1):163-78 (2012).
Notice of Acceptance for Australian Application No. 2017201146, dated Feb. 13, 2019 (3 pages).
Notice of Preliminary Rejection for Korean Application No. 10-2014-7007749, dated Sep. 13, 2018 (6 pages).
Ogino et al., "Template-directed DNA photoligation via alpha-5-cyanovinyldeoxyuridine," Org Lett. 7(14):2853-6 (2005).

(56) References Cited

OTHER PUBLICATIONS

*Pharmacological frontier—signal, protein factor, gene and modern pharmacology.* Edited by Wei, Erqing. Beijing: Science Publishing House. 314-316 (1999) (8 pages).
Pre-Appeal Examination Report for Japanese Application No. 2014-529907, dated Jul. 10, 2018 (8 pages).
Pujari et al., "Cross-Linked DNA Generated by 'Bis-click' Reactions with Bis-functional Azides: Site Independent Ligation of Oligonucleotides via Nucleobase Alkynyl Chains," J Org Chem. 75(24):8693-6 (2010).
Qiu et al., "A diazirine-based nucleoside analogue for efficient DNA interstrand photocross-linking," J Am Chem Soc. 130(44):14398-9 (2008).
Second Written Opinion for Singaporean Patent Application No. 2014011381, dated Oct. 19, 2017 (8 pages).
Xiong et al., "Cross-Linked DNA: Site-Selective 'Click' Ligation in Duplexes with Bis-Azides and Stability Changes Caused by Internal Cross-Links," Bioconjug Chem. 23(6):1230-43 (2012).
Xiong et al., "Stepwise 'Click' Chemistry for the Template Independent Construction of a Broad Variety of Cross-Linked Oligonucleotides: Influence of Linker Length, Position, and Linking Number on DNA Duplex Stability," J Org Chem. 76:5584-5597 (2011).
Yoshimura et al., "Highly selective and sensitive template-directed photoligation of DNA via 5-carbamoylvinyl-2'-deoxycytidine," Org Lett. 8(22):5049-51 (2006).
Yoshimura et al., Supporting Information for "Ultrafast Reversible Photocrosslinking Reaction: Toward in Situ DNA Manipulation," Org Lett. (2008) (20 pages).
Notification of Defects for Israeli Patent Application No. 231191, dated Mar. 26, 2019, received May 20, 2019 (6 pages).
Khakshoor et al., "Chemistry of nucleic acids: impacts in multiple fields," Chem Commun. 47(25):7018-24 (2011).
Lallana et al., "Reliable and efficient procedures for the conjugation of biomolecules through Huisgen azide-alkyne cycloadditions," Angew Chem Int Ed Engl. 50(38):8794-804 (2011).
Notice of Preliminary Rejection for Korean Patent Application No. 10-2014-7007749, dated May 28, 2019 (4 pages).
Notice of Reasons for Rejection for Japanese Patent Application No. 2018-089600, dated Aug. 21, 2019 (13 pages).
Examination Report for Canadian Patent Application No. 2,848,023, dated Dec. 10, 2019 (3 pages).
Examination Report No. 1 for Australian Patent Application No. 2019200965, dated Jan. 17, 2020 (3 pages).
Notice of Reasons for Rejection for Japanese Application No. 2014-529907, dated Nov. 14, 2019 (10 pages).
Search Report and Written Opinion for Singaporean Application No. 10201605812Y, dated May 21, 2020 (8 pages).
Interlocutory Decision in Opposition Proceedings (Art. 101(3)(a) and 106(2) EPC) for European Application No. 13816635.0, dated Apr. 7, 2020 (144 pages).
Letter from the Opponent in Response to the Summons to Attend Oral Proceedings Pursuant to Rule 115(1) EPC for European Patent No. 2748357, dated Apr. 30, 2020 (7 pp.).
Office Action for Eurasian Patent Application No. 201990336, dated Apr. 17, 2020 (4 pages).
Zhao et al., "Effects of 2'-O-methyl nucleotide on ligation capability of T4 DNA ligase," Acta Biochim Biophys Sin (Shanghai). 46(9):727-37 (2014).
Uhlenbeck and Gumport ("Uhlenbeck & Gumport"), The Enzymes, vol. XV, pp. 31-58 (1982).†
Blondal et al. ("Blondal"), Nucl. Acids. Res. vol. 33, pp. 135-142 (2005).†
Tessier et al. ("Tessier"), Anal. Biochem. vol. 158, pp. 171-178 (1986).†
Cummins et al. ("Cummins"), Nucl. Acids Res. vol. 23, No. 11, pp. 2019-2024 (1995).†

\* cited by examiner
† cited by third party

| donor length / acceptor length | 5 | 8 | 15 |
|---|---|---|---|
| 5 | 0.68 | 0.66 | 0.86 |
| 8 | 0.60 | 0.88 | 0.76 |
| 15 | 0.57 | 0.74 | 0.80 |

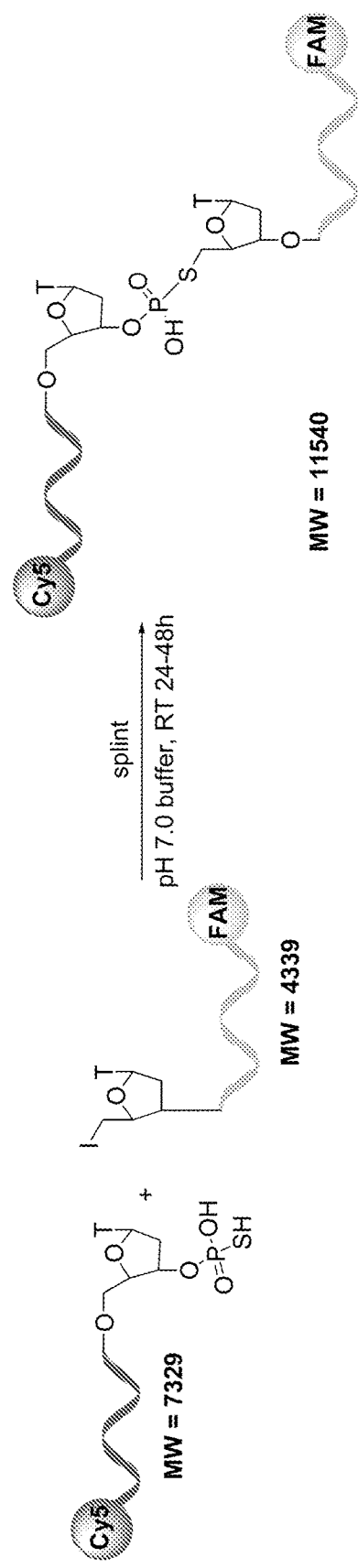
Figure 12A
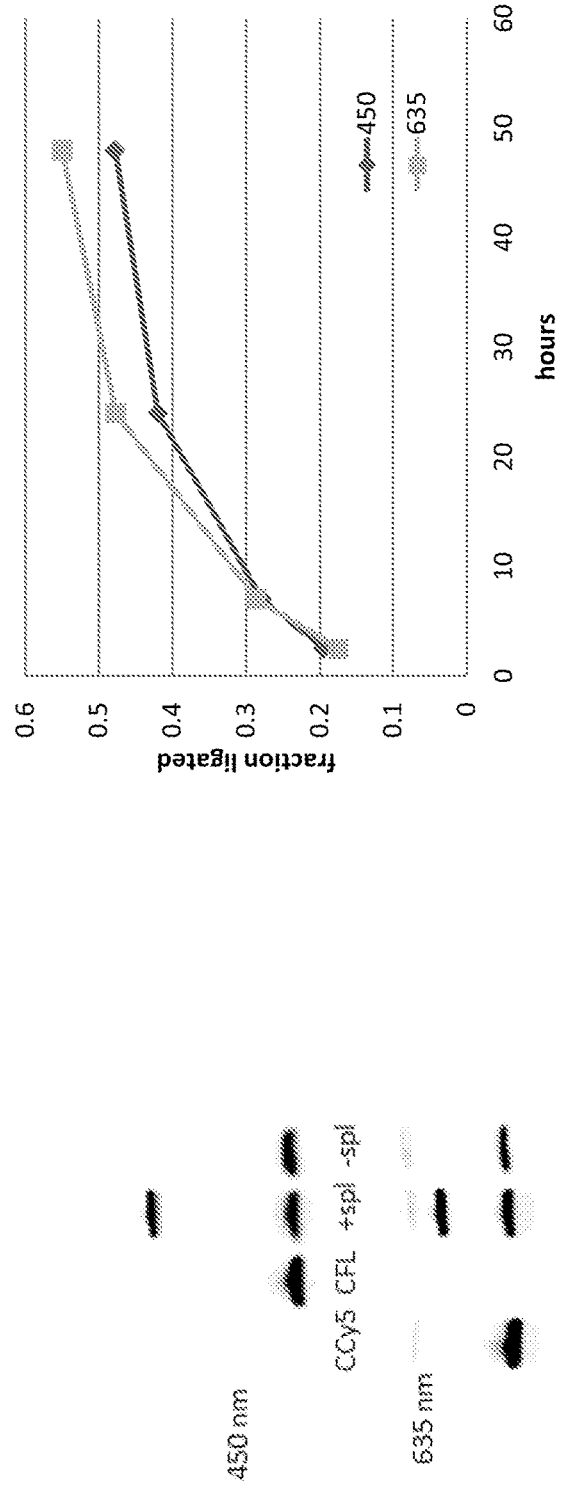
Figure 12C
Figure 12B

No splint: incubation for 7 days with 50 µM oligonucleotides

Only starting materials: Iodo dT_12_Fam (4339) and Cy5_21_ThioPhosphate (7329)

Splint: incubation for 7 days with 50 µM oligonucleotides

Product (11542)

(Peak 1- tag, peak 2- adenylated HP)

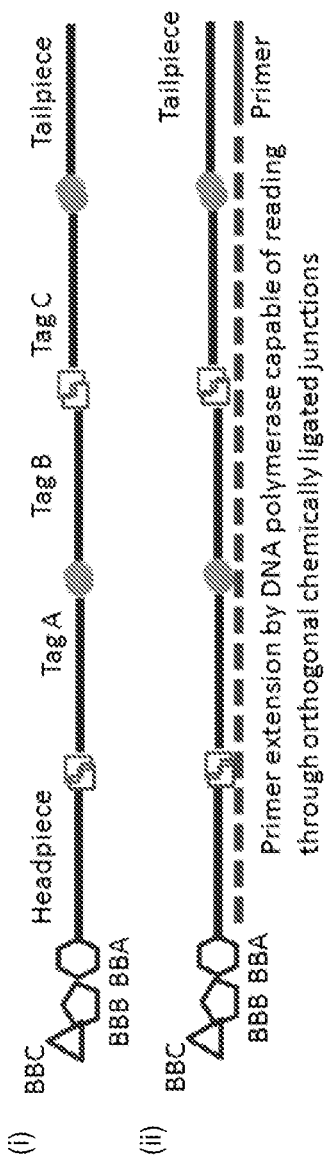
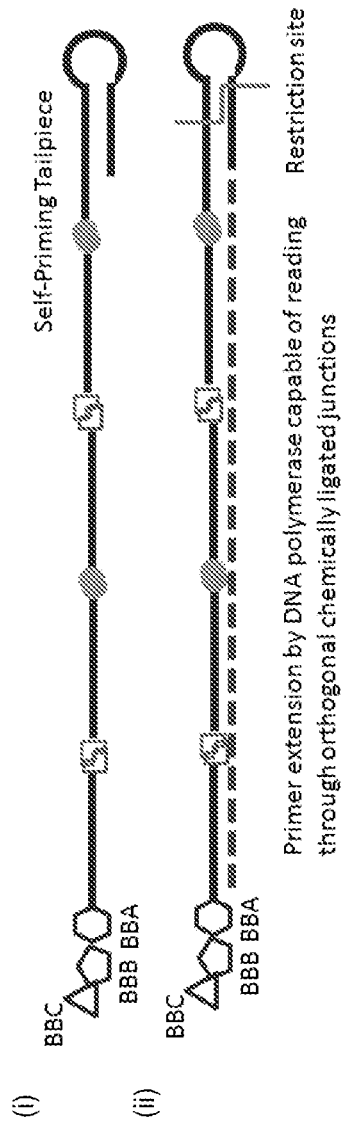
Figure 22B
Figure 22C

SEQUENCE LISTING

```
<160> NUMBER OF SEQ ID NOS: 39

<210> SEQ ID NO 1
<211> LENGTH: 7
<212> TYPE: DNA
<213> ORGANISM: Artificial Sequence
<220> FEATURE:
<223> OTHER INFORMATION: Synthetic Construct

<400> SEQUENCE: 1 gtgctgc                                                                    7

<210> SEQ ID NO 2
<211> LENGTH: 9
<212> TYPE: DNA
<213> ORGANISM: Artificial Sequence
<220> FEATURE:
<223> OTHER INFORMATION: Synthetic Construct

<400> SEQUENCE: 2 gcagcaccc                                                                  9

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is N-alpha-benzyloxycarbonyl
<220> FEATURE:
<221> NAME/KEY: MISC_FEATURE
<222> LOCATION: (8)..(8)
<223> OTHER INFORMATION: Xaa is OSu (N-succinimidyl ester)

<400> SEQUENCE: 3

Xaa Gly Gly Gly Gly Gly Gly Xaa
 1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is azidohomoalanine
<220> FEATURE:
```

```
<221> NAME/KEY: MISC_FEATURE
<222> LOCATION: (5)..(5)
<223> OTHER INFORMATION: Xaa is OSu (N-succinimidyl ester)

<400> SEQUENCE: 4

Xaa Gly Gly Gly Xaa
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is propargylglycine
<220> FEATURE:
<221> NAME/KEY: MISC_FEATURE
<222> LOCATION: (5)..(5)
<223> OTHER INFORMATION: Xaa is OSu (N-succinimidyl ester)

<400> SEQUENCE: 5

Xaa Gly Gly Gly Xaa
1               5

<210> SEQ ID NO 6
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal phosphate group
<220> FEATURE:
<221> NAME/KEY: misc_feature
<222> LOCATION: (18)..(18)
<223> OTHER INFORMATION: 3' terminal 6-FAM

<400> SEQUENCE: 6
gctgtgcagg tagagtgc                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal phosphate group
<220> FEATURE:
<221> NAME/KEY: misc_feature
<222> LOCATION: (1)..(1)
<223> OTHER INFORMATION: 2'-OMe is attached to g
<220> FEATURE:
<221> NAME/KEY: misc_feature
<222> LOCATION: (18)..(18)
<223> OTHER INFORMATION: 3' terminal 6-FAM

<400> SEQUENCE: 7
gctgtgcagg tagagtgc                                                 18

<210> SEQ ID NO 8
<211> LENGTH: 15
<212> TYPE: RNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal phosphate group
<220> FEATURE:
<221> NAME/KEY: misc_feature
<222> LOCATION: (1)..(1)
<223> OTHER INFORMATION: 2'-OMe is attached to g
<220> FEATURE:
<221> NAME/KEY: misc_feature
<222> LOCATION: (2)..(2)
<223> OTHER INFORMATION: 2'-OMe is attached to u
<220> FEATURE:
<221> NAME/KEY: misc_feature
<222> LOCATION: (3)..(3)
<223> OTHER INFORMATION: 2'-OMe is attached to g
<220> FEATURE:
<221> NAME/KEY: misc_feature
<222> LOCATION: (4)..(4)
<223> OTHER INFORMATION: 2'-OMe is attached to c
<220> FEATURE:
<221> NAME/KEY: misc_feature
<222> LOCATION: (5)..(5)
<223> OTHER INFORMATION: 2'-OMe is attached to a
<220> FEATURE:
<221> NAME/KEY: misc_feature
<222> LOCATION: (6)..(6)
<223> OTHER INFORMATION: 2'-OMe is attached to g
<220> FEATURE:
<221> NAME/KEY: misc_feature
<222> LOCATION: (7)..(7)
<223> OTHER INFORMATION: 2'-OMe is attached to g
<220> FEATURE:
<221> NAME/KEY: misc_feature
<222> LOCATION: (8)..(8)
<223> OTHER INFORMATION: 2'-OMe is attached to u
<220> FEATURE:
<221> NAME/KEY: misc_feature
<222> LOCATION: (9)..(9)
<223> OTHER INFORMATION: 2'-OMe is attached to a
<220> FEATURE:
<221> NAME/KEY: misc_feature
<222> LOCATION: (10)..(10)
<223> OTHER INFORMATION: 2'-OMe is attached to g
<220> FEATURE:
<221> NAME/KEY: misc_feature
<222> LOCATION: (11)..(11)
<223> OTHER INFORMATION: 2'-OMe is attached to a
<220> FEATURE:
<221> NAME/KEY: misc_feature
<222> LOCATION: (12)..(12)
<223> OTHER INFORMATION: 2'-OMe is attached to g
<220> FEATURE:
<221> NAME/KEY: misc_feature
<222> LOCATION: (13)..(13)
<223> OTHER INFORMATION: 2'-OMe is attached to u
<220> FEATURE:
<221> NAME/KEY: misc_feature
<222> LOCATION: (14)..(14)
<223> OTHER INFORMATION: 2'-OMe is attached to g
<220> FEATURE:
<221> NAME/KEY: misc_feature
<222> LOCATION: (15)..(15)
<223> OTHER INFORMATION: 2'-OMe is attached to c
<220> FEATURE:
<221> NAME/KEY: misc_feature
<222> LOCATION: (15)..(15)
<223> OTHER INFORMATION: 3' terminal 6-FAM

<400> SEQUENCE: 8
gugcagguag agugc                                                        15

<210> SEQ ID NO 9
<211> LENGTH: 15
<212> TYPE: DNA
```

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal HO-
<220> FEATURE:
<221> NAME/KEY: misc_feature
<222> LOCATION: (15)..(15)
<223> OTHER INFORMATION: 2'-OMe is attached to g
<220> FEATURE:
<221> NAME/KEY: misc_feature
<222> LOCATION: (15)..(15)
<223> OTHER INFORMATION: 3' terminal -OH

<400> SEQUENCE: 9
tacgtatacg actgg                                                  15

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal HO-
<220> FEATURE:
<221> NAME/KEY: misc_feature
<222> LOCATION: (21)..(21)
<223> OTHER INFORMATION: 3' terminal -OH

<400> SEQUENCE: 10
gcagactacg tatacgactg g                                           21

<210> SEQ ID NO 11
<211> LENGTH: 15
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal HO-
<220> FEATURE:
<221> NAME/KEY: misc_feature
<222> LOCATION: (1)..(1)
<223> OTHER INFORMATION: 2'-OMe is attached to u
<220> FEATURE:
<221> NAME/KEY: misc_feature
<222> LOCATION: (2)..(2)
<223> OTHER INFORMATION: 2'-OMe is attached to a
<220> FEATURE:
<221> NAME/KEY: misc_feature
<222> LOCATION: (3)..(3)
<223> OTHER INFORMATION: 2'-OMe is attached to c
<220> FEATURE:
<221> NAME/KEY: misc_feature
<222> LOCATION: (4)..(4)
<223> OTHER INFORMATION: 2'-OMe is attached to g
<220> FEATURE:
<221> NAME/KEY: misc_feature
<222> LOCATION: (5)..(5)
<223> OTHER INFORMATION: 2'-OMe is attached to u
<220> FEATURE:
<221> NAME/KEY: misc_feature
<222> LOCATION: (6)..(6)
<223> OTHER INFORMATION: 2'-OMe is attached to a
<220> FEATURE:
<221> NAME/KEY: misc_feature
<222> LOCATION: (7)..(7)
<223> OTHER INFORMATION: 2'-OMe is attached to u
```

```
<220> FEATURE:
<221> NAME/KEY: misc_feature
<222> LOCATION: (8)..(8)
<223> OTHER INFORMATION: 2'-OMe is attached to a
<220> FEATURE:
<221> NAME/KEY: misc_feature
<222> LOCATION: (9)..(9)
<223> OTHER INFORMATION: 2'-OMe is attached to c
<220> FEATURE:
<221> NAME/KEY: misc_feature
<222> LOCATION: (10)..(10)
<223> OTHER INFORMATION: 2'-OMe is attached to g
<220> FEATURE:
<221> NAME/KEY: misc_feature
<222> LOCATION: (11)..(11)
<223> OTHER INFORMATION: 2'-OMe is attached to a
<220> FEATURE:
<221> NAME/KEY: misc_feature
<222> LOCATION: (12)..(12)
<223> OTHER INFORMATION: 2'-OMe is attached to c
<220> FEATURE:
<221> NAME/KEY: misc_feature
<222> LOCATION: (13)..(13)
<223> OTHER INFORMATION: 2'-OMe is attached to u
<220> FEATURE:
<221> NAME/KEY: misc_feature
<222> LOCATION: (14)..(14)
<223> OTHER INFORMATION: 2'-OMe is attached to g
<220> FEATURE:
<221> NAME/KEY: misc_feature
<222> LOCATION: (15)..(15)
<223> OTHER INFORMATION: 2'-OMe is attached to g
<220> FEATURE:
<221> NAME/KEY: misc_feature
<222> LOCATION: (15)..(15)
<223> OTHER INFORMATION: 3' terminal -OH

<400> SEQUENCE: 11
uacguauacg acugg                                                          15

<210> SEQ ID NO 12
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal phosphate group
<220> FEATURE:
<221> NAME/KEY: misc_feature
<222> LOCATION: (1)..(1)
<223> OTHER INFORMATION: 2'-OMe is attached to g
<220> FEATURE:
<221> NAME/KEY: misc_feature
<222> LOCATION: (15)..(15)
<223> OTHER INFORMATION: 3' terminal 6-FAM

<400> SEQUENCE: 12
gtgcaggtag agtgc                                                          15

<210> SEQ ID NO 13
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal HO-
<220> FEATURE:
<221> NAME/KEY: misc_feature
<222> LOCATION: (1)..(1)
```

```
<223> OTHER INFORMATION: 2'-OMe is attached to u
<220> FEATURE:
<221> NAME/KEY: misc_feature
<222> LOCATION: (15)..(15)
<223> OTHER INFORMATION: 2'-OMe is attached to g
<220> FEATURE:
<221> NAME/KEY: misc_feature
<222> LOCATION: (15)..(15)
<223> OTHER INFORMATION: 3' terminal -OH

<400> SEQUENCE: 13
uacgtatacg actgg                                                         15

<210> SEQ ID NO 14
<211> LENGTH: 8
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal phosphate group
<220> FEATURE:
<221> NAME/KEY: misc_feature
<222> LOCATION: (1)..(1)
<223> OTHER INFORMATION: 2'-OMe is attached to g
<220> FEATURE:
<221> NAME/KEY: misc_feature
<222> LOCATION: (8)..(8)
<223> OTHER INFORMATION: 3' terminal 6-FAM

<400> SEQUENCE: 14 gtgagtgc                                                                  8

<210> SEQ ID NO 15
<211> LENGTH: 8
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal HO-
<220> FEATURE:
<221> NAME/KEY: misc_feature
<222> LOCATION: (8)..(8)
<223> OTHER INFORMATION: 2'-OMe is attached to g
<220> FEATURE:
<221> NAME/KEY: misc_feature
<222> LOCATION: (8)..(8)
<223> OTHER INFORMATION: 3' terminal -OH

<400> SEQUENCE: 15 cagactgg                                                                  8

<210> SEQ ID NO 16
<211> LENGTH: 5
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal phosphate group
<220> FEATURE:
<221> NAME/KEY: misc_feature
<222> LOCATION: (1)..(1)
<223> OTHER INFORMATION: 2'-OMe is attached to g
<220> FEATURE:
<221> NAME/KEY: misc_feature
```

<222> LOCATION: (5)..(5)
<223> OTHER INFORMATION: 3' terminal 6-FAM

<400> SEQUENCE: 16 gtgac                                                                       5

<210> SEQ ID NO 17
<211> LENGTH: 5
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal HO-
<220> FEATURE:
<221> NAME/KEY: misc_feature
<222> LOCATION: (1)..(1)
<223> OTHER INFORMATION: 2'-OMe is attached to a
<220> FEATURE:
<221> NAME/KEY: misc_feature
<222> LOCATION: (5)..(5)
<223> OTHER INFORMATION: 2'-OMe is attached to g
<220> FEATURE:
<221> NAME/KEY: misc_feature
<222> LOCATION: (5)..(5)
<223> OTHER INFORMATION: 3' terminal -OH

<400> SEQUENCE: 17 actgg                                                                       5

<210> SEQ ID NO 18
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (38)..(38)
<223> OTHER INFORMATION: g is propargylG

<400> SEQUENCE: 18
gcgtgaacat gcatctcccg tatgcgtaca gtccattg                                  38

<210> SEQ ID NO 19
<211> LENGTH: 37
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: t is azidoT

<400> SEQUENCE: 19
tatagcgcga tatacacact ggcgagcttg cgtactg                                   37

<210> SEQ ID NO 20
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (38)..(38)
<223> OTHER INFORMATION: 3' terminal includes spacer7-azide

<400> SEQUENCE: 20
gcgtgaacat gcatctcccg tatgcgtaca gtccattg                                    38

<210> SEQ ID NO 21
<211> LENGTH: 35
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal hexynyl

<400> SEQUENCE: 21
tagcgcgata tacacactgg cgagcttgcg tactg                                       35

<210> SEQ ID NO 22
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal Cy5

<400> SEQUENCE: 22
cagtacgcaa gctcg                                                             15

<210> SEQ ID NO 23
<211> LENGTH: 75
<212> TYPE: DNA
<213> ORGANISM: Artificial Sequence
<220> FEATURE:
<223> OTHER INFORMATION: Synthetic Construct

<400> SEQUENCE: 23
gcgtgaacat gcatctcccg tatgcgtaca gtccattgta tagcgcgata tacacactgg            60
cgagcttgcg tactg                                                             75

<210> SEQ ID NO 24
<211> LENGTH: 18
<212> TYPE: DNA
<213> ORGANISM: Artificial Sequence
<220> FEATURE:
<223> OTHER INFORMATION: Synthetic Construct

<400> SEQUENCE: 24
gcgtgaacat gcatctcc                                                          18

<210> SEQ ID NO 25
<211> LENGTH: 17
<212> TYPE: DNA
<213> ORGANISM: Artificial Sequence
<220> FEATURE:
<223> OTHER INFORMATION: Synthetic Construct

<400> SEQUENCE: 25
cagtacgcaa gctcgcc                                                           17

<210> SEQ ID NO 26
<211> LENGTH: 21
<212> TYPE: DNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal Cy5
<220> FEATURE:
<221> NAME/KEY: misc_feature
<222> LOCATION: (21)..(21)
<223> OTHER INFORMATION: 3' terminal thiophosphate

<400> SEQUENCE: 26
cgatatacac actggcgagc t                                              21

<210> SEQ ID NO 27
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: t is IododT
<220> FEATURE:
<221> NAME/KEY: misc_feature
<222> LOCATION: (12)..(12)
<223> OTHER INFORMATION: 3' terminal 6-FAM

<400> SEQUENCE: 27
tgcgtactga gc                                                        12

<210> SEQ ID NO 28
<211> LENGTH: 17
<212> TYPE: DNA
<213> ORGANISM: Artificial Sequence
<220> FEATURE:
<223> OTHER INFORMATION: Synthetic Construct

<400> SEQUENCE: 28
cagtacgcaa gctcgcc                                                   17

<210> SEQ ID NO 29
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal phosphate group
<220> FEATURE:
<221> NAME/KEY: misc_feature
<222> LOCATION: (1)..(1)
<223> OTHER INFORMATION: 2'-OMe is attached to c
<220> FEATURE:
<221> NAME/KEY: misc_feature
<222> LOCATION: (11)..(11)
<223> OTHER INFORMATION: 3' terminal aminohex

<400> SEQUENCE: 29
cgagtcacgt c                                                         11

<210> SEQ ID NO 30
<211> LENGTH: 8
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (1)..(1)
<223> OTHER INFORMATION: 2'-OMe is attached to c
<220> FEATURE:
<221> NAME/KEY: misc_feature
<222> LOCATION: (8)..(8)
<223> OTHER INFORMATION: 2'-OMe is attached to a

<400> SEQUENCE: 30 cagtgtca                                                                    8

<210> SEQ ID NO 31
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal phosphate group
<220> FEATURE:
<221> NAME/KEY: misc_feature
<222> LOCATION: (1)..(1)
<223> OTHER INFORMATION: 2'-OMe is attached to c
<220> FEATURE:
<221> NAME/KEY: misc_feature
<222> LOCATION: (2)..(2)
<223> OTHER INFORMATION: g is synthesized as a phosphorothioate linkage
<220> FEATURE:
<221> NAME/KEY: misc_feature
<222> LOCATION: (11)..(11)
<223> OTHER INFORMATION: 3' terminal aminohex

<400> SEQUENCE: 31
cgagtcacgt c                                                               11

<210> SEQ ID NO 32
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amidation
<220> FEATURE:
<221> NAME/KEY: misc_feature
<222> LOCATION: (18)..(18)
<223> OTHER INFORMATION: g is propargylG

<400> SEQUENCE: 32
tcgaatgact ccgatatg                                                        18

<210> SEQ ID NO 33
<211> LENGTH: 37
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: t is azido dT

<400> SEQUENCE: 33
tatagcgcga tatacacact ggcgagcttg cgtactg                                   37

<210> SEQ ID NO 34
<211> LENGTH: 25
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: t is azido dT

<400> SEQUENCE: 34
tacacactgg cgagcttgcg tactg                                            25

<210> SEQ ID NO 35
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: t is azido dT
<220> FEATURE:
<221> NAME/KEY: misc_feature
<222> LOCATION: (15)..(15)
<223> OTHER INFORMATION: u is propargyl U-TIPS

<400> SEQUENCE: 35
tatgcgtaca gtccu                                                       15

<210> SEQ ID NO 36
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal 6-FAM

<400> SEQUENCE: 36
cagtacgcaa gctcgcc                                                     17

<210> SEQ ID NO 37
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal Cy5

<400> SEQUENCE: 37
cagtacgcaa gctcgcc                                                     17

<210> SEQ ID NO 38
<211> LENGTH: 55
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal Biotin-TEG//ispC3//ispC3

<400> SEQUENCE: 38
```

```
tcgaatgact ccgatatgta tagcgcgata tacacactgg cgagcttgcg tactg        55

<210> SEQ ID NO 39
<211> LENGTH: 55
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' terminal Bio-TEG//ispC3//ispC3
<220> FEATURE:
<221> NAME/KEY: misc_feature
<222> LOCATION: (18)..(18)
<223> OTHER INFORMATION: g is riboG

<400> SEQUENCE: 39
tcgaatgact ccgatatgta tagcgcgata tacacactgg cgagcttgcg tactg        55
```

METHODS FOR TAGGING DNA-ENCODED LIBRARIES

CROSS-REFERENCE TO RELATED APPLICATIONS

This application is the U.S. National Stage of International Application No. PCT/US2012/054228, filed Sep. 7, 2012, which claims the benefit of U.S. Provisional Application Nos. 61/531,820, filed Sep. 7, 2011, and 61/536,929, filed Sep. 20, 2011, each of which is hereby incorporated by reference.

BACKGROUND OF THE INVENTION

In general, this invention relates to DNA-encoded libraries of compounds and methods of using and creating such libraries. The invention also relates to compositions for use in such libraries.

DNA-encoded combinatorial libraries afford many benefits for drug discovery. These libraries can provide a large number of diverse compounds that can be rapidly screened and interrogated. To further increase complexity, various steps of the discovery process can be programmed and automated. These steps include the use of multi-step, split-and-pool synthesis to add building blocks to atomic or polyatomic scaffolds and the use of enzymatic and/or chemical ligation to add DNA tags that encode both the synthetic steps and the building blocks.

Despite these benefits, numerous issues can arise when very large or complex libraries must be synthesized and deconvoluted. As the size of the library increases, improved methods may be needed to provide high yields of tag ligation. To create libraries under diverse reaction conditions, stable ligated nucleotide constructs would be beneficial, such as constructs that are stable under conditions of high pH and elevated temperature. To simplify deconvolution of tags, the sequence of the tags could be recognized by DNA- or RNA-dependent polymerases, such that tag population demographics can be determined by template-dependent polymerization and sequence determination. Difficulties may arise when creating a library having all of these beneficial attributes. Accordingly, there exists a need for improved, more robust methods of screening and identifying small compounds in DNA-encoded libraries.

SUMMARY OF THE INVENTION

The present invention features methods of creating libraries, where the method includes one or more conditions that improve single-stranded ligation of tags, and compositions for use in creating libraries. Exemplary conditions include the use of one or more 2'-substituted bases within the tags, such as 2'-O-methyl or 2'-fluoro; the use of tags of particular length; the use of one or more enzymes; optionally, the inclusion of error-recognition capabilities in the tag design; and/or the use of one or more agents during ligation.

Accordingly, the invention features a method of tagging a first library including an oligonucleotide-encoded chemical entity, the method including: (i) providing a headpiece having a first functional group and a second functional group, where the headpiece includes at least one 2'-substituted nucleotide; (ii) binding the first functional group of the headpiece to a first component of the chemical entity, where the headpiece is directly connected to the first component or the headpiece is indirectly connected to the first component by a bifunctional linker (e.g., a poly ethylene glycol linker or —$(CH_2CH_2O)_nCH_2CH_2$—, where n is an integer from 1 to 50); and (iii) binding the second functional group of the headpiece to a first building block tag to form a complex, where steps (ii) and (iii) can be performed in any order and where the first building block tag encodes for the binding reaction of step (ii), thereby providing a tagged library.

In some embodiments, the headpiece includes a 2'-substituted nucleotide at one or more of the 5'-terminus, the 3'-terminus, or the internal position of the headpiece. In particular embodiments, the headpiece includes the 2'-substituted nucleotide and the second functional group at the 5'-terminus or at the 3'-terminus.

In other embodiments, the first building block tag includes at least one (e.g., at least two, three, four, five, or more) 2'-substituted nucleotides. In particular embodiments, the first building block tag includes a 2'-substituted nucleotide at one or more of the 5'-terminus, the 3'-terminus, or the internal position of the first building block tag (e.g., a 2'-O-methyl nucleotide or a 2'-fluoro nucleotide at both of the 5'- and 3'-termini). In some embodiments, the first building block tag includes a protecting group at the 3'-terminus or at the 5'-terminus.

In any of the embodiments described herein, the 2'-substituted nucleotide is a 2'-O-methyl nucleotide (e.g., 2'-O-methyl guanine or 2'-O-methyl uracil) or a 2'-fluoro nucleotide (e.g., 2'-fluoro guanine, or 2'-fluoro uracil).

In any of the above embodiments, step (ii) may include joining, binding, or operatively associating the headpiece directly to the first component (e.g., a scaffold or a first building block). In yet other embodiments, step (ii) includes binding the headpiece indirectly to the first component (e.g., a scaffold or a first building block) via a bifunctional linker (e.g., the method includes binding the headpiece with the first functional group of the linker and binding the first component with the second functional group of the linker).

In any of the above embodiments, the method may further include (iv) binding a second building block tag to the 5'-terminus or 3'-terminus of the complex; and (v) binding a second component (e.g., a first building block or a second building block) of the chemical library to the first component, where steps (iv) and (v) can be performed in any order. In some embodiments, the second building block tag encodes for the binding reaction of step (v). In other embodiments, step (iv) may include binding the second building block tag to the 5'-terminus of the complex; the complex includes a phosphate group at the 5'-terminus; and the second building block tag includes a hydroxyl group at both of the 3'- and 5'-termini. In other embodiments, step (iv) may further include purifying the complex and reacting the complex with a polynucleotide kinase to form a phosphate group on the 5'-terminus prior to binding the second building block tag. In other embodiments, step (iv) may include binding the second building block tag to the 3'-terminus of the complex; the complex includes a protecting group at the 3'-terminus; and the second building block tag includes a phosphate group at the 5'-terminus and a protecting group at the 3'-terminus. In yet other embodiments, step (iv) may further include reacting the complex with a hydrolyzing agent to release the protecting group from the complex prior to binding the second building block tag to the complex.

In further embodiments, the second building block tag includes a 2'-substituted nucleotide (e.g., a 2'-O-methyl nucleotide or a 2'-fluoro nucleotide) at one or more of the 5'-terminus, the 3'-terminus, or the internal position of the second building block tag (e.g., a 2'-O-methyl nucleotide and/or a 2'-fluoro nucleotide at both of the 5'- and 3'-termini).

In some embodiments, step (iv) may include the use of an RNA ligase (e.g., T4 RNA ligase) and/or a DNA ligase (e.g., a ssDNA ligase) to bind the second building block tag to the complex (e.g., may include the use of both RNA ligase and the DNA ligase).

In other embodiments, step (iii) may include the use of an RNA ligase (e.g., T4 RNA ligase) and/or a DNA ligase (e.g., ssDNA ligase) to bind the headpiece to the first building block tag (e.g., may include the use of both RNA ligase and the DNA ligase).

In further embodiments, step (iii) and/or step (iv), if present, may include the use of poly ethylene glycol and/or one or more soluble multivalent cations (e.g., magnesium chloride, manganese (II) chloride, or hexamine cobalt (III) chloride). In some embodiments, the poly ethylene glycol is in an amount from about 25% (w/v) to about 35% (w/v) (e.g., from about 25% (w/v) to about 30% (w/v), from about 30% (w/v) to about 35% (w/v), or about 30% (w/v)). In other embodiments, the poly ethylene glycol has an average molecular weight from about 3,000 to about 5,500 Daltons (e.g., about 4,600 Daltons). In other embodiments, the one or more soluble multivalent cations are in an amount of from about 0.05 mM to about 10.5 mM (e.g., from 0.05 mM to 0.5 mM, from 0.05 mM to 0.75 mM, from 0.05 mM to 1.0 mM, from 0.05 mM to 1.5 mM, from 0.05 mM to 2.0 mM, from 0.05 mM to 3.0 mM, from 0.05 mM to 4.0 mM, from 0.05 mM to 5.0 mM, from 0.05 mM to 6.0 mM, from 0.05 mM to 7.0 mM, from 0.05 mM to 8.0 mM, from 0.05 mM to 9.0 mM, from 0.05 mM to 10.0 mM, from 0.1 mM to 0.5 mM, from 0.1 mM to 0.75 mM, from 0.1 mM to 1.0 mM, from 0.1 mM to 1.5 mM, from 0.1 mM to 2.0 mM, from 0.1 mM to 3.0 mM, from 0.1 mM to 4.0 mM, from 0.1 mM to 5.0 mM, from 0.1 mM to 6.0 mM, from 0.1 mM to 7.0 mM, from 0.1 mM to 8.0 mM, from 0.1 mM to 9.0 mM, from 0.1 mM to 10.0 mM, from 0.1 mM to 10.5 mM, from 0.5 mM to 0.75 mM, from 0.5 mM to 1.0 mM, from 0.5 mM to 1.5 mM, from 0.5 mM to 2.0 mM, from 0.5 mM to 3.0 mM, from 0.5 mM to 4.0 mM, from 0.5 mM to 5.0 mM, from 0.5 mM to 6.0 mM, from 0.5 mM to 7.0 mM, from 0.5 mM to 8.0 mM, from 0.5 mM to 9.0 mM, from 0.5 mM to 10.0 mM, from 0.5 mM to 10.5 mM, from 0.75 mM to 1.0 mM, from 0.75 mM to 1.5 mM, from 0.75 mM to 2.0 mM, from 0.75 mM to 3.0 mM, from 0.75 mM to 4.0 mM, from 0.75 mM to 5.0 mM, from 0.75 mM to 6.0 mM, from 0.75 mM to 7.0 mM, from 0.75 mM to 8.0 mM, from 0.75 mM to 9.0 mM, from 0.75 mM to 10.0 mM, from 0.75 mM to 10.5 mM, from 1.0 mM to 1.5 mM, from 1.0 mM to 2.0 mM, from 1.0 mM to 3.0 mM, from 1.0 mM to 4.0 mM, from 1.0 mM to 5.0 mM, from 1.0 mM to 6.0 mM, from 1.0 mM to 7.0 mM, from 1.0 mM to 8.0 mM, from 1.0 mM to 9.0 mM, from 1.0 mM to 10.0 mM, from 1.0 mM to 10.5 mM, from 1.5 mM to 2.0 mM, from 1.5 mM to 3.0 mM, from 1.5 mM to 4.0 mM, from 1.5 mM to 5.0 mM, from 1.5 mM to 6.0 mM, from 1.5 mM to 7.0 mM, from 1.5 mM to 8.0 mM, from 1.5 mM to 9.0 mM, from 1.5 mM to 10.0 mM, from 1.5 mM to 10.5 mM, from 2.0 mM to 3.0 mM, from 2.0 mM to 4.0 mM, from 2.0 mM to 5.0 mM, from 2.0 mM to 6.0 mM, from 2.0 mM to 7.0 mM, from 2.0 mM to 8.0 mM, from 2.0 mM to 9.0 mM, from 2.0 mM to 10.0 mM, and from 2.0 mM to 10.5 mM). In some embodiments, one or more multivalent cations are in an amount of about 1 mM (e.g., from 0.5 mM to 1.5 mM). In a particular embodiment, the multivalent cation is in the form of hexamine cobalt (III) chloride.

In other embodiments, the method further includes separating the complex from any unreacted tag or unreacted headpiece before any one of binding steps (ii)-(v). In other embodiments, the method further includes purifying the complex before any one of binding steps (ii)-(v). In other embodiments, the method further includes binding one or more additional components (e.g., a scaffold or a first building block) and one or more additional building block tags, in any order and after any one of binding step (ii)-(v).

The invention also features a method of tagging a first library including an oligonucleotide-encoded chemical entity, the method including: (i) providing a headpiece having a first functional group and a second functional group, where the headpiece includes a 2'-substituted nucleotide at the 5'-terminus, optionally one or more nucleotides at the internal position of the headpiece, and a protecting group at the 2'-position and/or the 3'-position at the 3'-terminus; (ii) binding the first functional group of the headpiece to a first component of the chemical entity, where the headpiece is directly connected to the first component or the headpiece is indirectly connected to the first component by a bifunctional linker; and (iii) binding the second functional group of the headpiece to a first building block tag, where the first building block tag includes a 2'-substituted nucleotide and a hydroxyl group at the 5'-terminus, optionally one or more nucleotides at the internal position of the tag, and a 2'-substituted nucleotide and a hydroxyl group at the 3'-terminus; where steps (ii) and (iii) can be performed in any order and where the first building block tag encodes for the binding reaction of step (ii), thereby providing a tagged library.

In some embodiments, the 2'-substituted nucleotide is a 2'-O-methyl nucleotide (e.g., 2'-O-methyl guanine) or a 2'-fluoro nucleotide (e.g., 2'-fluoro guanine). In other embodiments, one or more nucleotides at the internal position of the headpiece are 2'-deoxynucleotides. In yet other embodiments, the bifunctional linker is a poly ethylene glycol linker (e.g., —(CH$_2$CH$_2$O)$_n$CH$_2$CH$_2$—, where n is an integer from 1 to 50).

In other embodiments, one or more nucleotides (e.g., one or more 2'-deoxynucleotides) are present at the internal position of the headpiece or the tag.

In some embodiments, step (iii) may include the use of one or more soluble multivalent cations (e.g., magnesium chloride, manganese (II) chloride, or hexamine cobalt (III) chloride), poly ethylene glycol (e.g., having an average molecular weight of about 4,600 Daltons), and RNA ligase (e.g., T4 RNA ligase).

In another aspect, the invention features methods to identify and/or discover a chemical entity, the method including tagging a first library including an oligonucleotide-encoded chemical entity (e.g., including steps (i) to (iii) and optionally including steps (iv) to (v)) and selecting for a particular characteristic or function (e.g., selecting for binding to a protein target including exposing the oligonucleotide-encoded chemical entity or chemical entity to the protein target and selecting the one or more oligonucleotide-encoded chemical entities or chemical entities that bind to the protein target (e.g., by using size exclusion chromatography)). The invention also features a complex including a headpiece and a building block tag, where the tag includes from 5 to 20 nucleotides, a 2'-substituted nucleotide at the 5'-terminus, and a 2'-substituted nucleotide at the 3'-terminus. In some embodiments, the 2'-substituted nucleotide at the 5'-terminus and/or 3'-terminus is a 2'-O-methyl nucleotide (e.g., 2'-O-methyl guanine or 2'-O-methyl uracil) or a 2'-fluoro nucleotide (e.g., 2'-fluoro guanine or 2'-fluoro uracil). In particular embodiments, the headpiece includes a hairpin structure. In some embodiments, the headpiece includes a 2'-substituted nucleotide at one or more of the 5'-terminus, the 3'-terminus, or the internal position of the headpiece. In other embodiments, the headpiece further includes a preadenylated 5'-terminus. In yet other embodiments, the headpiece includes from 5 to 20 nucleotides.

In any of the above embodiments, the headpiece, the first building block tag, the second building block tag, or the one or more additional building block tags, if present, includes a preadenylated 5'-terminus.

In any of the above embodiments, the method further includes binding one or more (e.g., one, two, three, four, five, six, seven, eight, nine, or ten) additional building block tags to the complex and binding one or more (e.g., one, two, three, four, five, six, seven, eight, nine, or ten) additional components (e.g., scaffolds or building blocks) to the complex, where the one or more additional building block tag encodes for the one or more additional components or encodes for the binding reaction of one or more additional components, thereby providing a tagged library.

In any of the above embodiments, the 2'-substituted nucleotide is a 2'-O-methyl nucleotide, such as 2'-O-methyl guanine, 2'-O-methyl uracil, 2'-O-methyl adenosine, 2'-O-methyl thymidine, 2'-O-methyl inosine, 2'-O-methyl cytidine, or 2'-O-methyl diamino purine. Alternatively, in any of the above embodiments, the 2'-substituted nucleotide is a 2'-fluoro nucleotide, such as 2'-fluoro guanine, 2'-fluoro uracil, 2'-fluoro adenosine, 2'-fluoro thymidine, 2'-fluoro inosine, 2'-fluoro cytidine, or 2'-fluoro diamino purine.

In any of the above embodiments, the RNA ligase is T4 RNA ligase and/or the DNA ligase is a ssDNA ligase.

In any of the above embodiments, the method includes a plurality of headpieces. In some embodiments of this method, each headpiece of the plurality of headpieces includes an identical sequence region and a different encoding region. In particular embodiments, the identical sequence region is a primer binding region. In other embodiments, the different encoding region is an initial building block tag that encodes for the headpiece or for an addition of an initial component.

In any of the above embodiments, binding in at least one of steps (ii)-(iv), if present, includes enzyme ligation and/or chemical ligation. In some embodiments, enzymatic ligation includes use of an RNA ligase (e.g., T4 RNA ligase) or a DNA ligase (e.g., ssDNA ligase). In other embodiments, enzymatic ligation includes use of an RNA ligase (e.g., T4 RNA ligase) and a DNA ligase (e.g., ssDNA ligase). In some embodiments, chemical ligation includes use of one or more chemically co-reactive pairs (e.g., a pair including an optionally substituted alkynyl group with an optionally substituted azido group; a pair including an optionally substituted diene having a 4π electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) with an optionally substituted dienophile or an optionally substituted heterodienophile having a 2π electron system (e.g., an optionally substituted alkenyl group or an optionally substituted alkynyl group); a pair including a nucleophile (e.g., an optionally substituted amine or an optionally substituted thiol) with a strained heterocyclyl electrophile (e.g., optionally substituted epoxide, aziridine, aziridinium ion, or episulfonium ion); a pair including a phosphorothioate group with an iodo group (e.g., a phosphorothioate group at the 3'-terminus and an iodo group at the 5'-terminus); or a pair including an aldehyde group with an amino group (e.g., a primary amino or a secondary amino group, including a hydrazido group)). In particular embodiments, the chemically co-reactive pair produces a resultant spacer having a length from about 4 to about 24 atoms (e.g., from about 4 to about 10 atoms). In other embodiments, chemical ligation includes use of a phosphorothioate group (e.g., at the 3'-terminus) and an iodo group (e.g., at the 5'-terminus). In further embodiments, chemical ligation includes a splint oligonucleotide in the binding reaction. In some embodiments, the chemical ligation includes use of a phosphorothioate group (e.g., at the 3'-terminus of the headpiece, the first building block tag, the second building block tag, the one or more additional building block tags, the library-identifying tag, the use tag, and/or the origin tag, if present), an iodo group (e.g., at the 5'-terminus of the headpiece, the first building block tag, the second building block tag, the one or more additional building block tags, the library-identifying tag, the use tag, and/or the origin tag, if present), and a splint oligonucleotide in the binding reaction, where the use avoids use of one or more protecting groups. In other embodiments, chemical ligation of multiple tags comprises alternating use of orthogonal chemically co-reactive pairs (e.g., any two or more chemically co-reactive pairs described herein) for ligating successive tags.

In any of the above embodiments, the headpiece may include a single-stranded (e.g., hairpin) structure.

In any of the above embodiments, the headpiece, the first building block tag, the second building block tag, the one or more additional building block tags, the library-identifying tag, the use tag, and/or the origin tag, if present, includes a sequence that is substantially identical (e.g., at least 50%, 60%, 70%, 75%, 80%, 85%, 90%, 95%, 96%, 97%, 98%, 99%, or 100% identical) to any sequence described herein (e.g., the sequence in any one of SEQ ID NOs: 6-21, 26, 27, or 29-31), or a sequence that is complementary to a sequence that is substantially identical (e.g., at least 50%, 60%, 70%, 75%, 80%, 85%, 90%, 95%, 96%, 97%, 98%, 99%, or 100% identical) to any sequence described herein (e.g., the sequence in any one of SEQ ID NOs: 6-21, 26, 27, or 29-31). In particular embodiments, the first building block tag, the second building block tag, the one or more additional building block tags, the library-identifying tag, the use tag, and/or the origin tag, if present, further includes a sequence that is substantially identical (e.g., at least 50%, 60%, 70%, 75%, 80%, 85%, 90%, 95%, 96%, 97%, 98%, 99%, or 100% identical) to the sequence of SEQ ID NO: 1 or SEQ ID NO: 2.

In any of the above embodiments, the methods or complexes include only single-stranded molecules, where the headpiece, the first building block tag, the second building block tag, and/or the one or more additional building block tags are single-stranded. In some embodiments, one or more of the single-stranded molecules have a hairpin structure. In particular embodiments, the headpiece includes a hairpin structure and the one or more building block tags do not include a hairpin structure.

In any of the above embodiments, the method further comprises one or more optional steps to diversify the library or to interrogate the members of the library, as described herein. In some embodiments, the method further comprises identifying a small drug-like library member that binds or inactivates a protein of therapeutic interest. In other embodiments, the method further comprises contacting a member of the library with a biological target under conditions suitable for at least one member of the library to bind to the target, removing one or more library members that do not bind to the target, and analyzing the one or more oligonucleotide tags associated with them.

As described herein, the use of single-stranded molecules (e.g., including hairpin molecules) could have numerous benefits. Accordingly, in any of the embodiments described herein, the methods and complexes include a headpiece, one or more building block tags, a complex, a chemical entity, a molecule, or any member of a tagged library having decreased mass, increased solubility (e.g., in an organic solvent), decreased cost, increased reactivity, increased target accessibility, decreased hydrodynamic radius, and/or increased accuracy of analytical assessments, as compared to a method including one or more double-stranded molecules (e.g., a double-stranded headpiece or a double-stranded building block tag). In some embodiments, each of the building block tags (e.g., the first building block tag, the second building block tag, and/or one or more additional building block tags, if present) has about the same mass (e.g., each building block tag has a mass that is about +/−10% from the average mass between two or more building block tags). In particular embodiments, the building block tag has a decreased mass (e.g., less than about 15,000 Daltons, about 14,000 Daltons, about 13,000 Daltons, about 12,000 Daltons, about 11,000 Daltons, about 10,000 Daltons, about 9,000 Daltons, about 8,000 Daltons, about 7,500 Daltons, about 7,000 Daltons, about 6,000 Daltons, about 6,500 Daltons, about 5,000 Daltons, about 5,500 Daltons, about 4,000 Daltons, about 4,500 Daltons, or about 3,000 Daltons) compared to a double-stranded tag (e.g., a double-stranded tag having a mass of about 15,000 Daltons, about 14,000 Daltons, about 13,000 Daltons, or about 12,000 Daltons). In other embodiments, the building block tag has a reduced length compared to a double-stranded tag (e.g., a double-stranded tag having a length of less than about 20 nucleotides, less than about 19 nucleotides, less than about 18 nucleotides, less than about 17 nucleotides, less than about 16 nucleotides, less than about 15 nucleotides, less than about 14 nucleotides, less than about 13 nucleotides, less than about 12 nucleotides, less than about 11 nucleotides, less than about 10 nucleotides, less than about 9 nucleotides, less than about 8 nucleotides, or less than about 7 nucleotides). In some embodiments, one or more building block tags or members of the library lack a primer binding region and/or a constant region (e.g., during a selection step, such as selection using size exclusion chromatography). In some embodiments, one or more building block tags or members of the library have a reduced constant region (e.g., a length less than about 30 nucleotides, less than about 25 nucleotides, less than about 20 nucleotides, less than about 19 nucleotides, less than about 18 nucleotides, less than about 17 nucleotides, less than about 16 nucleotides, less than about 15 nucleotides, less than about 14 nucleotides, less than about 13 nucleotides, less than about 12 nucleotides, less than about 11 nucleotides, less than about 10 nucleotides, less than about 9 nucleotides, less than about 8 nucleotides, or less than about 7 nucleotides). In other embodiments, the methods include a headpiece that encodes for a molecule, a portion of a chemical entity, a binding reaction (e.g., chemical or enzymatic ligation) of a step, or the identity of a library, where the encoding headpiece eliminates the need of an additional building block tag to encode such information.

In any of the above embodiments, an oligonucleotide (e.g., the headpiece, the first building block tag, the second building block tag, and/or one or more additional building block tags, if present) encodes for the identity of the library. In some embodiments, the oligonucleotide (e.g., the headpiece, the first building block tag, the second building block tag, and/or one or more additional building block tags, if present) includes a first library-identifying sequence, where the sequence encodes for the identity of the first library. In particular embodiments, the oligonucleotide is a first library-identifying tag. In some embodiments, the method includes providing a first library-identifying tag, where the tag includes a sequence that encodes for a first library, and/or binding the first library-identifying tag to the complex. In some embodiments, the method includes providing a second library and combining the first library with a second library. In further embodiments, the method includes providing a second library-identifying tag, where the tag includes a sequence that encodes for a second library.

In any of the above embodiments, an oligonucleotide (e.g., a headpiece and/or one or more building blocks) encodes for the use of the member of the library (e.g., use in a selection step or a binding step, as described herein). In some embodiments, the oligonucleotide (e.g., the headpiece, the first building block tag, the second building block tag, and/or one or more additional building block tags, if present) includes a use sequence, where the sequence encodes for use of a subset of members in the library in one or more steps (e.g., a selection step and/or a binding step). In particular embodiments, the oligonucleotide is a use tag including a use sequence. In some embodiments, an oligonucleotide (e.g., a headpiece and/or one or more building blocks) encodes for the origin of the member of the library (e.g., in a particular part of the library). In some embodiments, the oligonucleotide (e.g., the headpiece, the first building block tag, the second building block tag, and/or one or more additional building block tags, if present) includes an origin sequence (e.g., a random degenerate sequence having a length of about 10, 9, 8, 7, or 6 nucleotides), where the sequence encodes for the origin of the member in the library. In particular embodiments, the oligonucleotide is an origin tag including an origin sequence. In some embodiments, the method further includes joining, binding, or operatively associating a use tag and/or an origin tag to the complex.

In any of the above embodiments, the methods, compositions, and complexes optionally include a tailpiece, where the tailpiece includes one or more of a library-identifying sequence, a use sequence, or an origin sequence, as described herein. In particular embodiments, the methods further include joining, binding, or operatively associating the tailpiece (e.g., including one or more of a library-identifying sequence, a use sequence, or an origin sequence) to the complex.

In any of the above embodiments, the methods, compositions, and complexes, or portions thereof (e.g., the headpiece, the first building block tag, the second building block tag, and/or the one or more additional building block tags, if present), includes a modified phosphate group (e.g., a phosphorothioate or a 5'-N-phosphoramidite linkage) between the terminal nucleotide at the 3'-terminus and the nucleotide adjacent to the terminal nucleotide. In particular embodiments, the modified phosphate group minimizes shuffling during enzymatic ligation between two oligonucleotides (e.g., minimizes inclusion of an additional nucleotide or excision of a nucleotide in the final product or complex, as compared to the sequences of two oligonucleotides to be ligated, such as between a headpiece to a building block tag or between a first building block tag and a second building block tag), as compared to ligation between two oligonucleotides (e.g., a headpiece and a building block tag or a first building block tag and a second building block tag) lacking the modified phosphate group. In some embodiments, the complex may include a phosphorothioate or a triazole group.

In any of the above embodiments, the methods, compositions, and complexes, or portions thereof (e.g., the headpiece, the first building block tag, the second building block tag, and/or the one or more additional building block tags, if present), includes a modification that supports solubility in semi-, reduced-, or non-aqueous (e.g., organic) conditions. In some embodiments, the bifunctional linker, headpiece, or one or more building block tags is modified to increase solubility of a member of said DNA-encoded chemical library in organic conditions In some embodiments, the modification is one or more of an alkyl chain, a polyethylene glycol unit, a branched species with positive charges, or a hydrophobic ring structure. In some embodiments, the modification includes one or more modified nucleotides having a hydrophobic moiety (e.g., modified at the C5 positions of T or C bases with aliphatic chains, such as in 5'-dimethoxytrityl-N4-diisobutylaminomethylidene-5-(1-propynyl)-2'-deoxycytidine, 3'-[(2-cyanoethyl)-(N,N-diisopropyl)]-phosphoramidite; 5'-dimethoxytrityl-5-(1-propynyl)-2'-deoxyuridine, 3'-[(2-cyanoethyl)-(N,N-diisopropyl)]-phosphoramidite; 5'-dimethoxytrityl-5-fluoro-2'-deoxyuridine, 3'-[(2-cyanoethyl)-(N,N-diisopropyl)]-phosphoramidite; and 5'-dimethoxytrityl-5-(pyren-1-yl-ethynyl)-2'-deoxyuridine, or 3'-[(2-cyanoethyl)-(N,N-diisopropyl)]-phosphoramidite) or an insertion having a hydrophobic moiety (e.g., an azobenzene). In some embodiments, the member of the library has an octanol:water coefficient from about 1.0 to about 2.5 (e.g., about 1.0 to about 1.5, about 1.0 to about 2.0, about 1.3 to about 1.5, about 1.3 to about 2.0, about 1.3 to about 2.5, about 1.5 to about 2.0, about 1.5 to about 2.5, or about 2.0 to about 2.5).

In any of the above embodiments, the headpiece, the tailpiece, the first building block tag, the second building block tag, the one or more additional building block tags, the library-identifying tag, the use tag, and/or the origin tag, if present, may include from 5 to 20 nucleotides (e.g., from 5 to 7 nucleotides, from 5 to 8 nucleotides, from 5 to 9 nucleotides, from 5 to 10 nucleotides, from 5 to 11 nucleotides, from 5 to 12 nucleotides, from 5 to 13 nucleotides, from 5 to 14 nucleotides, from 5 to 15 nucleotides, from 5 to 16 nucleotides, from 5 to 17 nucleotides, from 5 to 18 nucleotides, from 5 to 19 nucleotides, from 6 to 7 nucleotides, from 6 to 8 nucleotides, from 6 to 9 nucleotides, from 6 to 10 nucleotides, from 6 to 11 nucleotides, from 6 to 12 nucleotides, from 6 to 13 nucleotides, from 6 to 14 nucleotides, from 6 to 15 nucleotides, from 6 to 16 nucleotides, from 6 to 17 nucleotides, from 6 to 18 nucleotides, from 6 to 19 nucleotides, from 6 to 20 nucleotides, from 7 to 8 nucleotides, from 7 to 9 nucleotides, from 7 to 10 nucleotides, from 7 to 11 nucleotides, from 7 to 12 nucleotides, from 7 to 13 nucleotides, from 7 to 14 nucleotides, from 7 to 15 nucleotides, from 7 to 16 nucleotides, from 7 to 17 nucleotides, from 7 to 18 nucleotides, from 7 to 19 nucleotides, from 7 to 20 nucleotides, from 8 to 9 nucleotides, from 8 to 10 nucleotides, from 8 to 11 nucleotides, from 8 to 12 nucleotides, from 8 to 13 nucleotides, from 8 to 14 nucleotides, from 8 to 15 nucleotides, from 8 to 16 nucleotides, from 8 to 17 nucleotides, from 8 to 18 nucleotides, from 8 to 19 nucleotides, from 8 to 20 nucleotides, from 9 to 10 nucleotides, from 9 to 11 nucleotides, from 9 to 12 nucleotides, from 9 to 13 nucleotides, from 9 to 14 nucleotides, from 9 to 15 nucleotides, from 9 to 16 nucleotides, from 9 to 17 nucleotides, from 9 to 18 nucleotides, from 9 to 19 nucleotides, from 9 to 20 nucleotides, from 10 to 11 nucleotides, from 10 to 12 nucleotides, from 10 to 13 nucleotides, from 10 to 14 nucleotides, from 10 to 15 nucleotides, from 10 to 16 nucleotides, from 10 to 17 nucleotides, from 10 to 18 nucleotides, from 10 to 19 nucleotides, from 10 to 20 nucleotides, from 11 to 12 nucleotides, from 11 to 13 nucleotides, from 11 to 14 nucleotides, from 11 to 15 nucleotides, from 11 to 16 nucleotides, from 11 to 17 nucleotides, from 11 to 18 nucleotides, from 11 to 19 nucleotides, from 11 to 20 nucleotides, from 12 to 13 nucleotides, from 12 to 14 nucleotides, from 12 to 15 nucleotides, from 12 to 16 nucleotides, from 12 to 17 nucleotides, from 12 to 18 nucleotides, from 12 to 19 nucleotides, from 12 to 20 nucleotides, from 13 to 14 nucleotides, from 13 to 15 nucleotides, from 13 to 16 nucleotides, from 13 to 17 nucleotides, from 13 to 18 nucleotides, from 13 to 19 nucleotides, from 13 to 20 nucleotides, from 14 to 15 nucleotides, from 14 to 16 nucleotides, from 14 to 17 nucleotides, from 14 to 18 nucleotides, from 14 to 19 nucleotides, from 14 to 20 nucleotides, from 15 to 16 nucleotides, from 15 to 17 nucleotides, from 15 to 18 nucleotides, from 15 to 19 nucleotides, from 15 to 20 nucleotides, from 16 to 17 nucleotides, from 16 to 18 nucleotides, from 16 to 19 nucleotides, from 16 to 20 nucleotides, from 17 to 18 nucleotides, from 17 to 19 nucleotides, from 17 to 20 nucleotides, from 18 to 19 nucleotides, from 18 to 20 nucleotides, and from 19 to 20 nucleotides). In particular embodiments, the headpiece, the first building block tag, the second building block tag, the one or more additional building block tags, the library-identifying tag, the use tag, and/or the origin tag, if present, have a length of less than 20 nucleotides (e.g., less than 19 nucleotides, less than 18 nucleotides, less than 17 nucleotides, less than 16 nucleotides, less than 15 nucleotides, less than 14 nucleotides, less than 13 nucleotides, less than 12 nucleotides, less than 11 nucleotides, less than 10 nucleotides, less than 9 nucleotides, less than 8 nucleotides, or less than 7 nucleotides).

In particular embodiments, the first building block tag and the second building block tag include the same number of nucleotides. In other embodiments, either the first building block tag or the second building block tag includes more than 8 nucleotides (e.g., more than 9 nucleotides, more than 10 nucleotides, more than 11 nucleotides, more than 12 nucleotides, more than 13 nucleotides, more than 14 nucleotides, and more than 15 nucleotides). In some embodiments, the first building block tag is a donor tag (e.g., as defined herein) having from 8 to 20 nucleotides (e.g., from 8 to 9 nucleotides, from 8 to 10 nucleotides, from 8 to 11 nucleotides, from 8 to 12 nucleotides, from 8 to 13 nucleotides, from 8 to 14 nucleotides, from 8 to 15 nucleotides, from 8 to 16 nucleotides, from 8 to 17 nucleotides, from 8 to 18 nucleotides, from 8 to 19 nucleotides, from 8 to 20 nucleotides, from 9 to 10 nucleotides, from 9 to 11 nucleotides, from 9 to 12 nucleotides, from 9 to 13 nucleotides, from 9 to 14 nucleotides, from 9 to 15 nucleotides, from 9 to 16 nucleotides, from 9 to 17 nucleotides, from 9 to 18 nucleotides, from 9 to 19 nucleotides, from 9 to 20 nucleotides, from 10 to 11 nucleotides, from 10 to 12 nucleotides, from 10 to 13 nucleotides, from 10 to 14 nucleotides, from 10 to 15 nucleotides, from 10 to 16 nucleotides, from 10 to 17 nucleotides, from 10 to 18 nucleotides, from 10 to 19 nucleotides, from 10 to 20 nucleotides, from 11 to 12 nucleotides, from 11 to 13 nucleotides, from 11 to 14 nucleotides, from 11 to 15 nucleotides, from 11 to 16 nucleotides, from 11 to 17 nucleotides, from 11 to 18 nucleotides, from 11 to 19 nucleotides, from 11 to 20 nucleotides, from 12 to 13 nucleotides, from 12 to 14 nucleotides, from 12 to 15 nucleotides, from 12 to 16 nucleotides, from 12 to 17 nucleotides, from 12 to 18 nucleotides, from 12 to 19 nucleotides, from 12 to 20 nucleotides, from 13 to 14 nucleotides, from 13 to 15 nucleotides, from 13 to 16 nucleotides, from 13 to 17 nucleotides, from 13 to 18 nucleotides, from 13 to 19 nucleotides, from 13 to 20 nucleotides, from 14 to 15 nucleotides, from 14 to 16 nucleotides, from 14 to 17 nucleotides, from 14 to 18 nucleotides, from 14 to 19 nucleotides, from 14 to 20 nucleotides, from 15 to 16 nucleotides, from 15 to 17 nucleotides, from 15 to 18 nucleotides, from 15 to 19 nucleotides, from 15 to 20 nucleotides, from 16 to 17 nucleotides, from 16 to 18 nucleotides, from 16 to 19 nucleotides, from 16 to 20 nucleotides, from 17 to 18 nucleotides, from 17 to 19 nucleotides, from 17 to 20 nucleotides, from 18 to 19 nucleotides, from 18 to 20 nucleotides, and from 19 to 20 nucleotides).

Definitions

By "2'-substituted nucleotide" is meant a nucleotide base having a substitution at the 2'-position of ribose in the base.

By "about" is meant +/−10% of the recited value.

By "bifunctional" is meant having two reactive groups that allow for binding of two chemical moieties. For example, a bifunctional linker is a linker, as described herein, having two reactive groups that allow for binding of a headpiece and a chemical entity By "binding" is meant attaching by a covalent bond or a non-covalent bond. Non-covalent bonds include those formed by van der Waals forces, hydrogen bonds, ionic bonds, entrapment or physical encapsulation, absorption, adsorption, and/or other intermolecular forces. Binding can be effectuated by any useful means, such as by enzymatic binding (e.g., enzymatic ligation) or by chemical binding (e.g., chemical ligation).

By "building block" is meant a structural unit of a chemical entity, where the unit is directly linked to other chemical structural units or indirectly linked through the scaffold. When the chemical entity is polymeric or oligomeric, the building blocks are the monomeric units of the polymer or oligomer. Building blocks can have one or more diversity nodes that allow for the addition of one or more other building blocks or scaffolds. In most cases, each diversity node is a functional group capable of reacting with one or more building blocks or scaffolds to form a chemical entity. Generally, the building blocks have at least two diversity nodes (or reactive functional groups), but some building blocks may have one diversity node (or reactive functional group). Alternatively, the encoded chemical or binding steps may include several chemical components (e.g., multi-component condensation reactions or multi-step processes). Reactive groups on two different building blocks should be complementary, i.e., capable of reacting together to form a covalent or a non-covalent bond.

By "building block tag" is meant an oligonucleotide portion of the library that encodes the addition (e.g., by a binding reaction) of a component (i.e., a scaffold or a building block), the headpiece in the library, the identity of the library, the use of the library, and/or the origin of a library member. By "acceptor tag" is meant a building block tag having a reactive entity (e.g., a hydroxyl group at the 3'-terminus in the case of enzymatic ligation). By "donor tag" is meant a building block tag having an entity capable of reacting with the reactive entity on the acceptor tag (e.g., a phosphoryl group at the 5'-terminus in the case of enzymatic ligation).

By "chemical entity" is meant a compound comprising one or more building blocks and optionally a scaffold. The chemical entity can be any small molecule or peptide drug or drug candidate designed or built to have one or more desired characteristics, e.g., capacity to bind a biological target, solubility, availability of hydrogen bond donors and acceptors, rotational degrees of freedom of the bonds, positive charge, negative charge, and the like. In certain embodiments, the chemical entity can be reacted further as a bifunctional or trifunctional (or greater) entity.

By "chemically co-reactive pair" is meant a pair of reactive groups that participates in a modular reaction with high yield and a high thermodynamic gain, thus producing a spacer. Exemplary reactions and chemically co-reactive pairs include a Huisgen 1,3-dipolar cycloaddition reaction with a pair of an optionally substituted alkynyl group and an optionally substituted azido group; a Diels-Alder reaction with a pair of an optionally substituted diene having a $4\pi$ electron system and an optionally substituted dienophile or an optionally substituted heterodienophile having a $2\pi$ electron system; a ring opening reaction with a nucleophile and a strained heterocyclyl electrophile; a splint ligation reaction with a phosphorothioate group and an iodo group; and a reductive amination reaction with an aldehyde group and an amino group, as described herein.

By "complex" or "ligated complex" is meant a headpiece that is operatively associated with a chemical entity and/or one or more oligonucleotide tags by a covalent bond or a non-covalent bond. The complex can optionally include a bifunctional linker between the chemical entity and the headpiece.

By "component" of a chemical entity is meant either a scaffold or a building block.

By "diversity node" is meant a functional group at a position in the scaffold or the building block that allows for adding another building block.

By "headpiece" is meant a starting oligonucleotide for library synthesis that is operatively linked to a component of a chemical entity and to a building block tag. Optionally, a bifunctional linker connects the headpiece to the component.

By "library" is meant a collection of molecules or chemical entities. Optionally, the molecules or chemical entities are bound to one or more oligonucleotides that encodes for the molecules or portions of the chemical entity.

By "linker" is meant a chemical connecting entity that links the headpiece to a chemical entity.

By "multivalent cation" is meant a cation capable of forming more than one bond with more than one ligand or anion. The multivalent cation can form either an ionic complex or a coordination complex. Exemplary multivalent cations include those from the alkali earth metals (e.g., magnesium) and transition metals (e.g., manganese (II) or cobalt (III)), and those that are optionally bound to one or more anions and/or one or more univalent or polydentate ligands, such as chloride, amine, and/or ethylenediamine.

By "oligonucleotide" is meant a polymer of nucleotides having a 5'-terminus, a 3'-terminus, and one or more nucleotides at the internal position between the 5'- and 3'-termini. The oligonucleotide may include DNA, RNA, or any derivative thereof known in the art that can be synthesized and used for base-pair recognition. The oligonucleotide does not have to have contiguous bases but can be interspersed with linker moieties. The oligonucleotide polymer may include natural bases (e.g., adenosine, thymidine, guanosine, cytidine, uridine, deoxyadenosine, deoxythymidine, deoxyguanosine, deoxycytidine, inosine, or diamino purine), base analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), modified nucleotides (e.g., 2'-substituted nucleotides, such as 2'-O-methylated bases and 2'-fluoro bases), intercalated bases, modified sugars (e.g., 2'-fluororibose, ribose, 2'-deoxyribose, arabinose, and hexose), and/or modified phosphate groups (e.g., phosphorothioates and 5'-N-phosphoramidite linkages). Other modified bases are described herein.

By "acceptor oligonucleotide" is meant an oligonucleotide having a reactive entity (e.g., a hydroxyl group at the 3'-terminus in the case of enzymatic ligation or an optionally substituted azido group in the case of chemical ligation). By "donor oligonucleotide" is meant an oligonucleotide having an entity capable of reacting with the reactive entity on the acceptor oligonucleotide (e.g., a phosphoryl group at the 5'-terminus in the case of enzymatic ligation or an optionally substituted alkynyl group in the case of chemical ligation).

By "operatively linked" or "operatively associated" is meant that two or more chemical structures are directly or indirectly linked together in such a way as to remain linked through the various manipulations they are expected to undergo. Typically, the chemical entity and the headpiece are operatively linked in an indirect manner (e.g., covalently via an appropriate linker). For example, the linker may be a bifunctional moiety with a site of attachment for chemical entity and a site of attachment for the headpiece. In addition, the chemical entity and the oligonucleotide tag can be operatively linked directly or indirectly (e.g., covalently via an appropriate linker).

By "protecting group" is a meant a group intended to protect the 3'-terminus or 5'-terminus of an oligonucleotide against undesirable reactions during one or more binding steps of tagging a DNA-encoded library. Commonly used protecting groups are disclosed in Greene, "Protective Groups in Organic Synthesis," 4$^{th}$ Edition (John Wiley & Sons, New York, 2007), which is incorporated herein by reference. Exemplary protecting groups include irreversible protecting groups, such as dideoxynucleotides and dideoxynucleosides (ddNTP or ddN), and, more preferably, reversible protecting groups for hydroxyl groups, such as ester groups (e.g., O-(α-methoxyethyl)ester, O-isovaleryl ester, and O-levulinyl ester), trityl groups (e.g., dimethoxytrityl and monomethoxytrityl), xanthenyl groups (e.g., 9-phenylxanthen-9-yl and 9-(p-methoxyphenyl)xanthen-9-yl), acyl groups (e.g., phenoxyacetyl and acetyl), and silyl groups (e.g., t-butyldimethylsilyl).

By "purifying" is meant removing any unreacted product or any agent present in a reaction mixture that may reduce the activity of a chemical or biological agent to be used in a successive step. Purifying can include one or more of chromatographic separation, electrophoretic separation, and precipitation of the unreacted product or reagent to be removed.

By "scaffold" is meant a chemical moiety that displays one or more diversity nodes in a particular special geometry. Diversity nodes are typically attached to the scaffold during library synthesis, but in some cases one diversity node can be attached to the scaffold prior to library synthesis (e.g., addition of one or more building blocks and/or one or more tags). In some embodiments, the scaffold is derivatized such that it can be orthogonally deprotected during library synthesis and subsequently reacted with different diversity nodes.

By "small molecule" drug or "small molecule" drug candidate is meant a molecule that has a molecular weight below about 1,000 Daltons. Small molecules may be organic or inorganic, isolated (e.g., from compound libraries or natural sources), or obtained by derivatization of known compounds.

By "substantial identity" or "substantially identical" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, or 20 contiguous amino acids, more preferably at least 25, 50, 75, 90, 100, 150, 200, 250, 300, or 350 contiguous amino acids, and most preferably the full-length amino acid sequence. For nucleic acids, the length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

By "tailpiece" is meant an oligonucleotide portion of the library that is attached to the complex after the addition of all of the building block tags and encodes for the identity of the library, the use of the library, and/or the origin of a library member.

Other features and advantages of the invention will be apparent from the following Detailed Description and the claims.

BRIEF DESCRIPTION OF THE DRAWINGS

FIG. 2A shows an exemplary method for tagging libraries using single-stranded enzymatic ligation with a protected (re-installed) 5'-monophosphate (5'-P) oligonucleotide, where gray boxes refer to 2'-OMe nucleotides, "X" refers to a protecting group or a component of a chemical entity, and "PNK" refers to polynucleotide kinase. FIG. 2B shows an exemplary method for tagging libraries using single-stranded ligation with a protected 3'-OH oligonucleotide, where black boxes attached to —O— refer to a protecting group of the 3'-OH terminus and "LC" refers to liquid chromatographic separation of the protecting group.

FIGS. 4A-4B are schematics for complexes having a single-stranded linear oligonucleotide headpiece, where the linker and small molecule are connected to the 3'-terminus (FIG. 4A) or the 5'-terminus (FIG. 4B) of the headpiece. FIGS. 4C-4D are schematics for complexes having a single-stranded hairpin oligonucleotide headpiece, where the linker and small molecule are connected to the internal position (FIG. 4C) or the 3'-terminus (FIG. 4D) of the headpiece. FIG. 4E shows an exemplary method for tagging libraries having a hairpin oligonucleotide headpiece, where the star refers to a chemical moiety and "Y" at the 3'-terminus refers to a protecting group. Oligonucleotide tags are labeled 1-4, and the adapter sequence is the black line at the 5'-terminus.

FIG. 5A is a schematic of the enzymatic ligation reaction. The donor oligonucleotide is 5'-phosphorylated and carries a 3'-fluorescein label, imitating a headpiece with a chemical library at 3' end. The acceptor oligonucleotide is not phosphorylated. FIG. 5B shows gel electrophoresis analysis of a ligation reaction on an 8M urea/15% polyacrylamide gel (PAAG). "SM" refers to fluorescently labeled donor, "Product" refers to ligation product, and "Adenylated donor" refers to 5'App-Donor, as described above. FIG. 5C shows high yield ligation achieved for T4 RNA ligase at high enzyme and oligonucleotide concentrations.

FIG. 6A is graph quantifying the electrophoretic analysis of a ligation reaction with MNA/DNA 15mer donor and acceptor tags after incubation for 5 hours or 20 hours with 25% (w/v) PEG having a molecular weight from 300 to 20,000 (20K). FIG. 6B shows the effect of concentration on ligation after incubation for 18-20 hours in the presence of 5% to 45% (w/v) of PEG4600.

FIG. 7A depicts a graph quantifying the effect of the acceptor length on ligation yield in the CircLigase™ ligation reaction. FIG. 7B depicts a graph and a table quantifying the effect of nucleotide length of the acceptor and donor MNA/DNA tags on single-stranded ligation with T4 RNA ligase. These data represent an average of two independent experiments obtained by densitometry of fluorescent gels at 450 nm excitation.

FIG. 11A is a schematic of the RT reaction. LC-MS spectra of the RT were recorded at both 260 nm and 650 nm for the control 75mer DNA template (FIG. 11B), the 75mer DNA template containing a single 5-atom ("short") spacer (FIG. 11C), and the 75mer DNA template containing a single 24-atom ("long") spacer (FIG. 11D). FIG. 11E shows RT-PCR analysis of the control 75mer DNA template ("temp175"), a 75mer DNA template with a 5-atom spacer ("short click"), and a 75mer DNA template with a 24-atom spacer ("long click").

FIGS. 12A-12G show the results of a chemical ligation reaction between a 5'-iodo-modified DNA oligonucleotide and a 3'-phosphorothioate DNA oligonucleotide in the presence or absence of a complementary splint oligonucleotide. FIG. 12A shows an exemplary schematic of the reaction. The 5'-iodo oligonucleotide is labeled with 6-FAM at 3'-terminus, while the 3'-phosphorothioate oligonucleotide is labeled with Cy5 at the 5'-terminus. FIG. 12B shows a gel electrophoresis analysis of the ligation reactions in the presence (+sp1) or absence (−sp1) of a complementary splint. CCy5 and CFL indicate visible bands of Cy5 and fluorescein-labeled starting material, respectively. FIG. 12C shows a time course of the splinted ligation reaction under the above conditions, which was quantified using Cy5 (635 nm) and fluorescein (450 nm) detection. FIG. 12D shows LC-MS analysis of the ligation of CFL and CCy5 in the absence (top, at 260 nm, 495 nm, and 650 nm) and presence (bottom, at 260 nm, 495 nm, and 650 nm) of a splint, where ligation reactions were incubated for seven days. FIG. 12E shows LC-MS analysis of the ligation of CFL and CCy5 in the absence a splint (at 260 nm, 495 nm, and 650 nm), where ligation reactions were incubated for eight days. FIG. 12F shows MS analysis of reaction of CFL oligonucleotide with piperidine, where this reaction was intended to displace iodine. Reaction conditions included oligonucleotides at 100 µM, piperidine at 40 mM (400 equivalents) in 100 mM borate buffer, pH 9.5, for 20 hrs at room temperature (left); and oligonucleotides at 400 µM, piperidine at 2 M (4,000 equivalents) in 200 mM borate buffer, pH 9.5, for 2 hrs at 65° C. (right). FIG. 12G shows MS analysis of a splinted ligation reaction of CFL and CCy5 oligonucleotides at 50 µM performed in the presence of 400 equivalents of piperidine in 100 mM borate buffer, pH 9.5, for 20 hrs at room temperature.

FIG. 13A shows an LC-MS analysis of a single-stranded ligation reaction of a 5'-phosphorylated headpiece ssHP (3,636 Da) and a tag (tag 15; 2,469 Da) having 2'-O methyl nucleotides. The LC-MS analysis showed three peaks: peak 1 for the tag (2,469 Da); peak 2 for the adenylated headpiece (3,965 Da); and peak 3 having two (in some instances three) sub-peaks containing products with molecular weights of 6,089 Da (expected ligation product); 5,769 Da (expected 6,089 Da−320 Da); and 6,409 Da (expected 6,089 Da+320 Da). This mass difference of 320 Da corresponds exactly to either removal or addition of an extra 2'-O-Me C nucleotide. FIGS. 13B-1 to 13B-3 show a non-limiting, proposed mechanism of the nucleotide shuffling, where about 90% of the reaction provides the expected (normal) ligation product and about 10% of the reaction provides aberrant ligation products ("Product−1 nt" and "Product+1 nt"). FIG. 13C shows an LC-MS analysis of ligation of headpiece HP-PS with tag 15. The headpiece HP-PS has the sequence the headpiece ssHP but includes a phosphorothioate linkage at the 5'-terminus. LC analysis showed three peaks: peak 1 for the tag (2,469), peak 2 for the adenylated headpiece (3,984), and peak 3 for a single ligation product (6,107) with almost no nucleotide shuffling observed. Traces of +/−320 peaks likely correspond to the oxidative conversion of the phosphorothioate linkage into a native phosphodiester linkage or are due to incomplete sulfurization.

FIG. 17A provides an exemplary schematic. FIG. 17B and FIG. 17C show LC-MS analysis of Y55 and Y185, respectively.

FIG. 18A shows a schematic, where FAM-labeled primer is annealed to the biotinylated template and is incubated with the template-dependent polymerase, according to the manufacturer's recommended conditions. The complexes are subsequently incubated with streptavidin beads, washed, eluted with NaOH, and then neutralized. After neutralization the samples are analyzed by LC-MS. FIG. 18B and FIG. 18C show LC-MS data of the Klenow fragment copying of templates Y55 and Y185, respectively.

FIGS. 19A and 19B show exemplary schematics for this synthesis. FIGS. 19C and 19D show LC-MS analysis of the YDC and YTC templates respectively.

FIG. 20A is a schematic, where FAM-labeled primer is annealed to the biotinylated template and is incubated with Klenow fragment of *E. coli* DNA polymerase I according to the manufacturer's recommended reaction conditions. The complexes are incubated with streptavidin beads, washed, eluted with NaOH, and neutralized. After the neutralization, the samples are assayed by LC-MS. FIGS. 20B and 20C show LC-MS data of the Klenow fragment copying of the templates YDC and YTC, respectively.

FIGS. 22A-22C provide exemplary schematics of chemical ligation with orthogonal chemistry. FIG. 22A is a schematic of the chemical ligation strategy for DNA encoding tags that (i) utilizes two successive orthogonal chemistries for (ii) available read-through strategies. Each tag contains two orthogonal reactive groups, indicated by differing symbols for the 5'-terminus and the 3'-terminus of each tag. In each successive cycle of chemical ligation, an orthogonal chemistry is used. This strategy reduces the frequency of occurrence of mistagging events and may also be used without the protection of the reactive terminal groups. FIG. 22B is a schematic of the template-dependent polymerization "read-though" of a template generated by the orthogonal chemical ligation of orthogonal DNA tags to generate cDNA from which the sequence of the tags can be deduced. FIG. 22C is the same as FIG. 22B but includes a self-priming tailpiece, which may be rendered double-stranded by restriction digestion to facilitate strand-separation during PCR amplification.

FIG. 24A shows an exemplary schematic for using protecting groups (PG) for these tags. FIG. 24B shows an exemplary scheme for use of 3'-phosphorothioate/5'-iodo tags to chemically ligate succession of encoding DNA tags that encode a chemical library covalently installed upon the 5'-terminus.

FIG. 25A shows the scheme for protection of these groups. FIG. 25B shows the scheme for use of 3'-phosphorothioate/5'-azido and 3'-propargyl/5'-iodo tags to chemically ligate a succession of orthogonal encoding DNA tags that encode a chemical library covalently installed upon the 5'-terminus.

DETAILED DESCRIPTION

Figure 1:
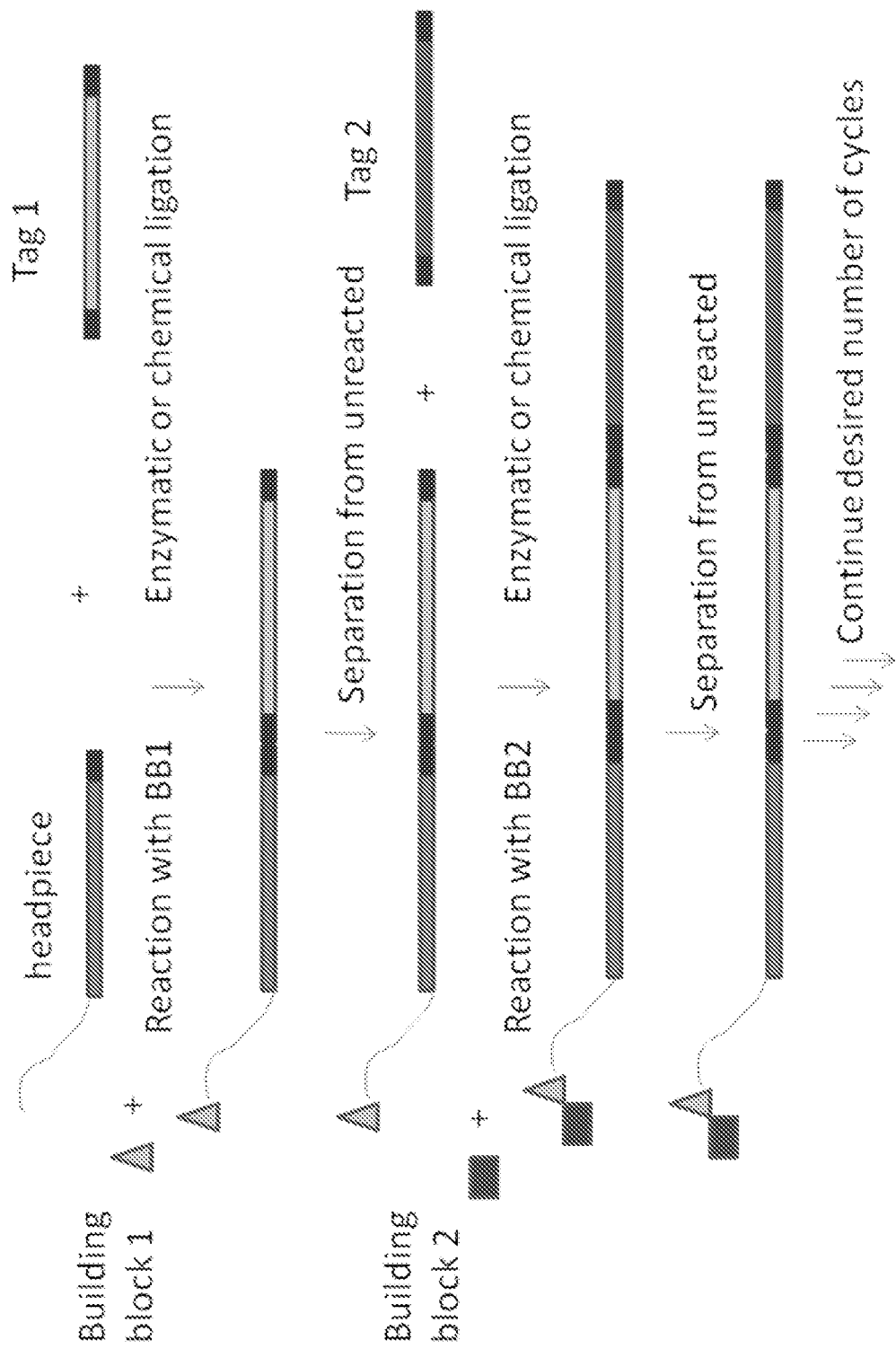
FIG. 1 shows an exemplary method for the general synthesis of chemical libraries using single-stranded DNA tags that are joined sequentially by means of enzymatic and/or chemical ligation. "BB" refers to building block.

The invention features methods of using single-stranded ligation to install oligonucleotide tags onto chemical entity-oligonucleotide complexes. This method can be used to create diverse libraries of selectable chemical entities by establishing an encoded relationship between particular tags and particular chemical reactions or building blocks. To identify one or more chemical entities, the oligonucleotide tags can be amplified, cloned, sequenced, and correlated by using the established relationship. In particular, reaction conditions that promote single-stranded ligation of tags were identified. These conditions include the use of one or more 2'-substituted nucleotides (e.g., 2'-O-methyl nucleotides or 2'-fluoro nucleotides) within the tags, the use of tags of particular length (e.g., between 5 and 15 nucleotides), the use of one or more enzymes (e.g., RNA ligase and/or DNA ligase), and/or the use of one or more agents during ligation (e.g., poly ethylene glycol and/or a soluble multivalent cation, such as $Co(NH_3)_6Cl_3$). These methods additionally include methods of chemically joining oligonucleotides, such that the sequence of the joined oligonucleotide product may be utilized as a template for a template-dependent polymerase reaction. Methods of creating and tagging libraries of these complexes are described in detail below.

Methods for Tagging Encoded Libraries

This invention features a method for operatively linking oligonucleotide tags with chemical entities, such that encoding relationships may be established between the sequence of the tag and the structural units (or building blocks) of the chemical entity. In particular, the identity and/or history of a chemical entity can be inferred from the sequence of bases in the oligonucleotide. Using this method, a library including diverse chemical entities or members (e.g., small molecules or peptides) can be addressed with a particular tag sequence.

Generally, these methods include the use of a headpiece, which has at least one functional group that may be elaborated chemically and at least one functional group to which a single-stranded oligonucleotide may be bound (or ligated). Binding can be effectuated by any useful means, such as by enzymatic binding (e.g., ligation with one or more of an RNA ligase and/or a DNA ligase) or by chemical binding (e.g., by a substitution reaction between two functional groups, such as a nucleophile and a leaving group).

To create numerous chemical entities within the library, a solution containing the headpiece can be divided into multiple aliquots and then placed into a multiplicity of physically separate compartments, such as the wells of a multi-well plate. Generally, this is the "split" step. Within each compartment or well, successive chemical reaction and ligation steps are performed with a single-stranded tag within each aliquot. The relationship between the chemical reaction conditions and the sequence of the single-stranded tag are recorded. The reaction and ligation steps may be performed in any order. Then, the reacted and ligated aliquots are combined or "pooled," and optionally purification may be performed at this point. These split and pool steps can be optionally repeated.

Next, the library can be tested and/or selected for a particular characteristic or function, as described herein. For example, the mixture of tagged chemical entities can be separated into at least two populations, where the first population binds to a particular biological target and the second population does not. The first population can then be selectively captured (e.g., by eluting on a column providing the target of interest or by incubating the aliquot with the target of interest) and, optionally, further analyzed or tested, such as with optional washing, purification, negative selection, positive selection, or separation steps.

Finally, the chemical histories of one or more members (or chemical entities) within the selected population can be determined by the sequence of the operatively linked oligonucleotide. Upon correlating the sequence with the particular building block, this method can identify the individual members of the library with the selected characteristic (e.g., an increased tendency to bind to the target protein and thereby elicit a therapeutic effect). For further testing and optimization, candidate therapeutic compounds may then be prepared by synthesizing the identified library members with or without their associated oligonucleotide tags.

Figure 3:
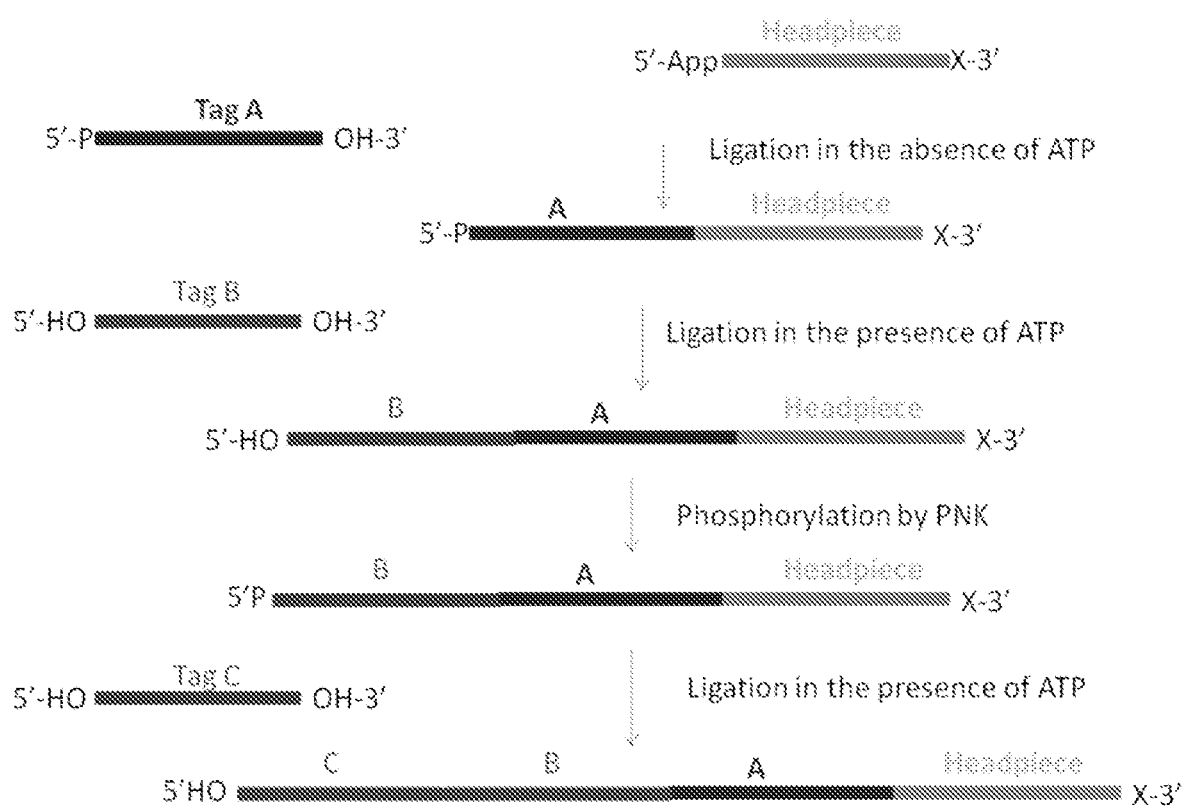
FIG. 3 shows an exemplary method for tagging libraries using single-stranded ligation with a 5'-preadenylated (labeled "5'-App") oligonucleotide (headpiece) with a 3'-terminus that is blocked, e.g., by a chemical entity (labeled "X-3'"). This method can be used to ligate a 5'-phosphorylated oligonucleotide tag (labeled "Tag A") to the headpiece and additional tags having a 3'-OH terminus (labeled "Tag B" and "Tag C") to the complex in the presence of ATP.
Figure 13A:
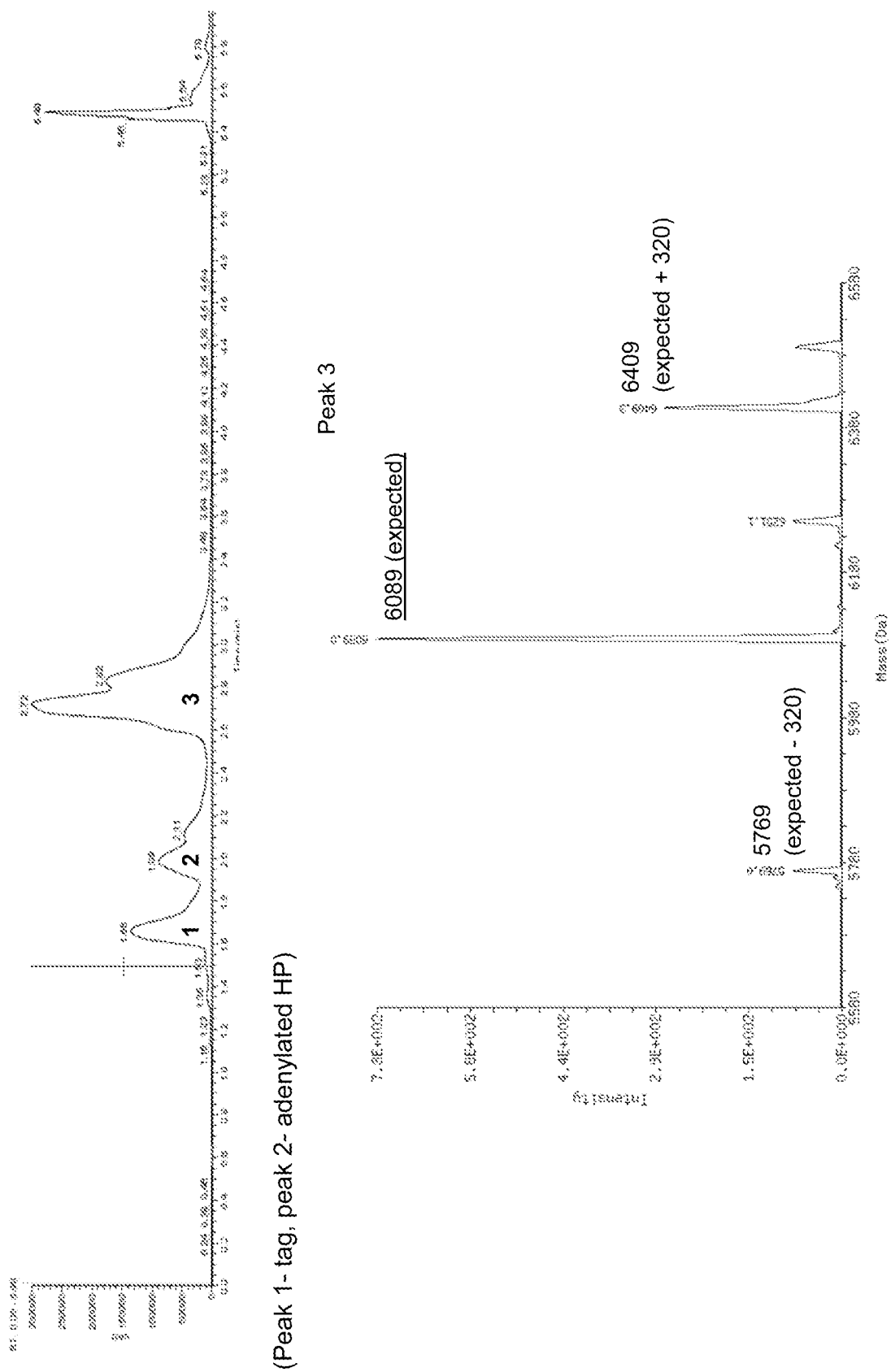
FIGS. 13A-13C shows the use of modified oligonucleotides to minimize shuffling.
Figures 1, 13B:
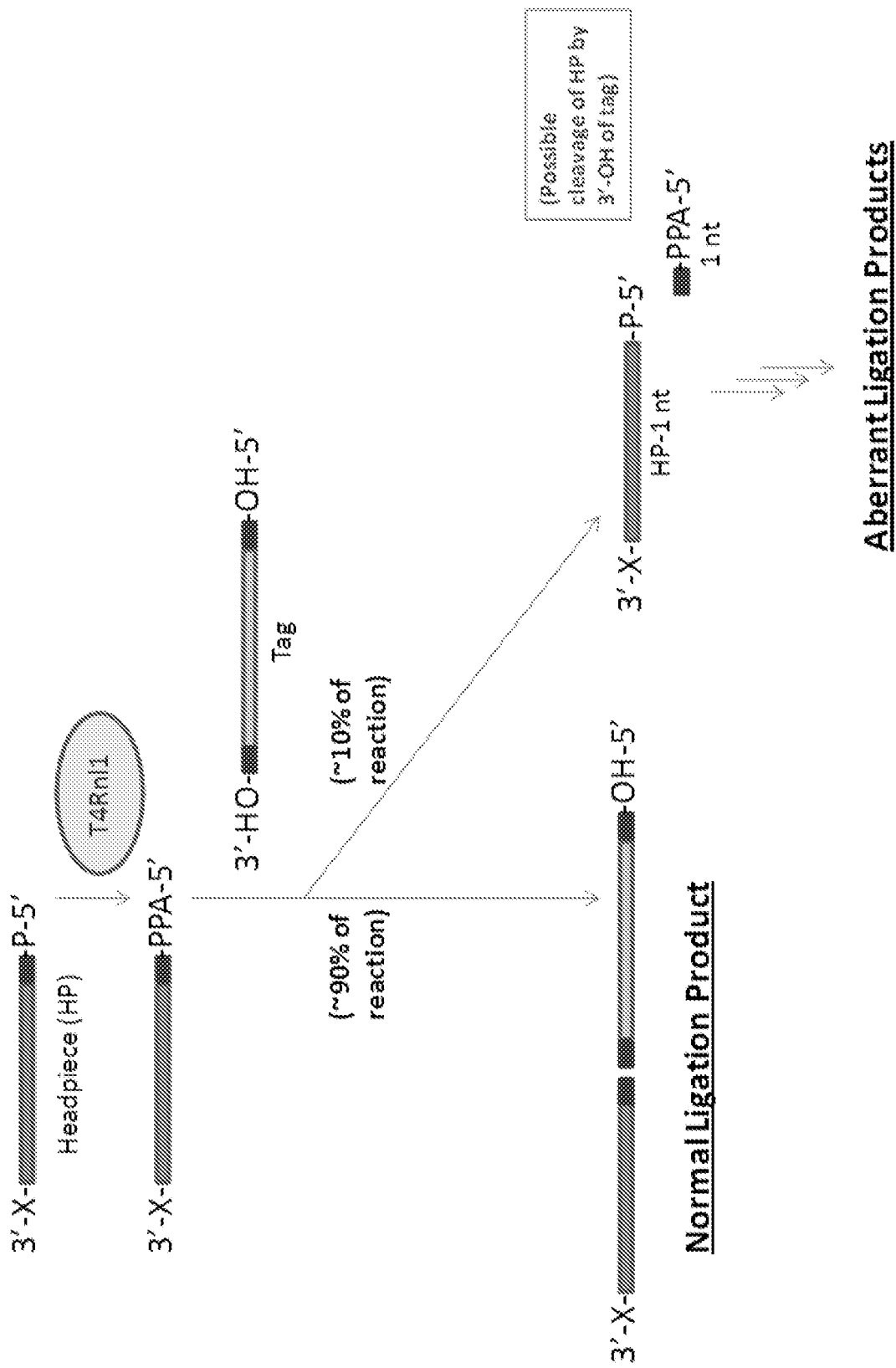
Figures 2, 13B:
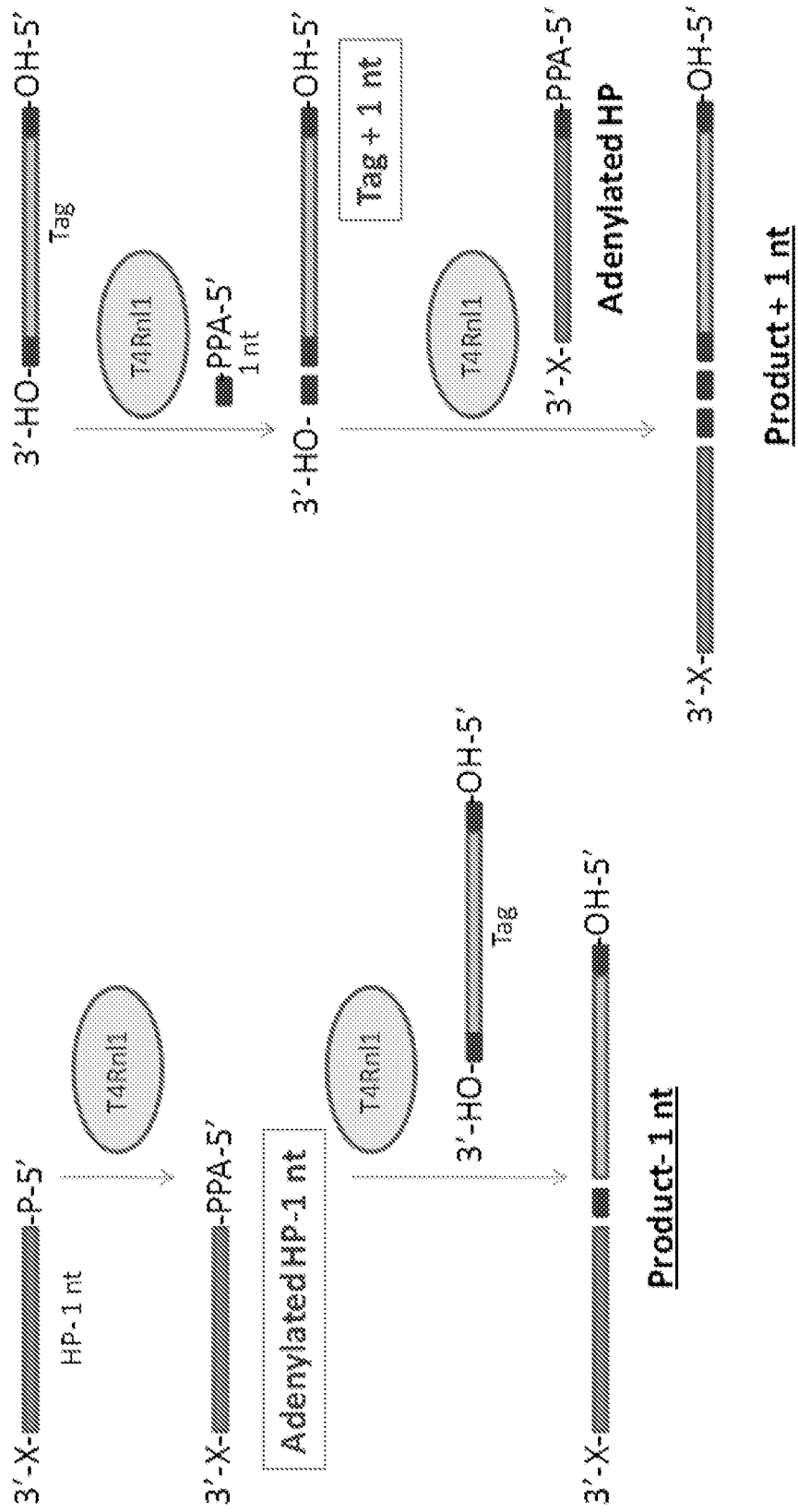
Figures 3, 13B:
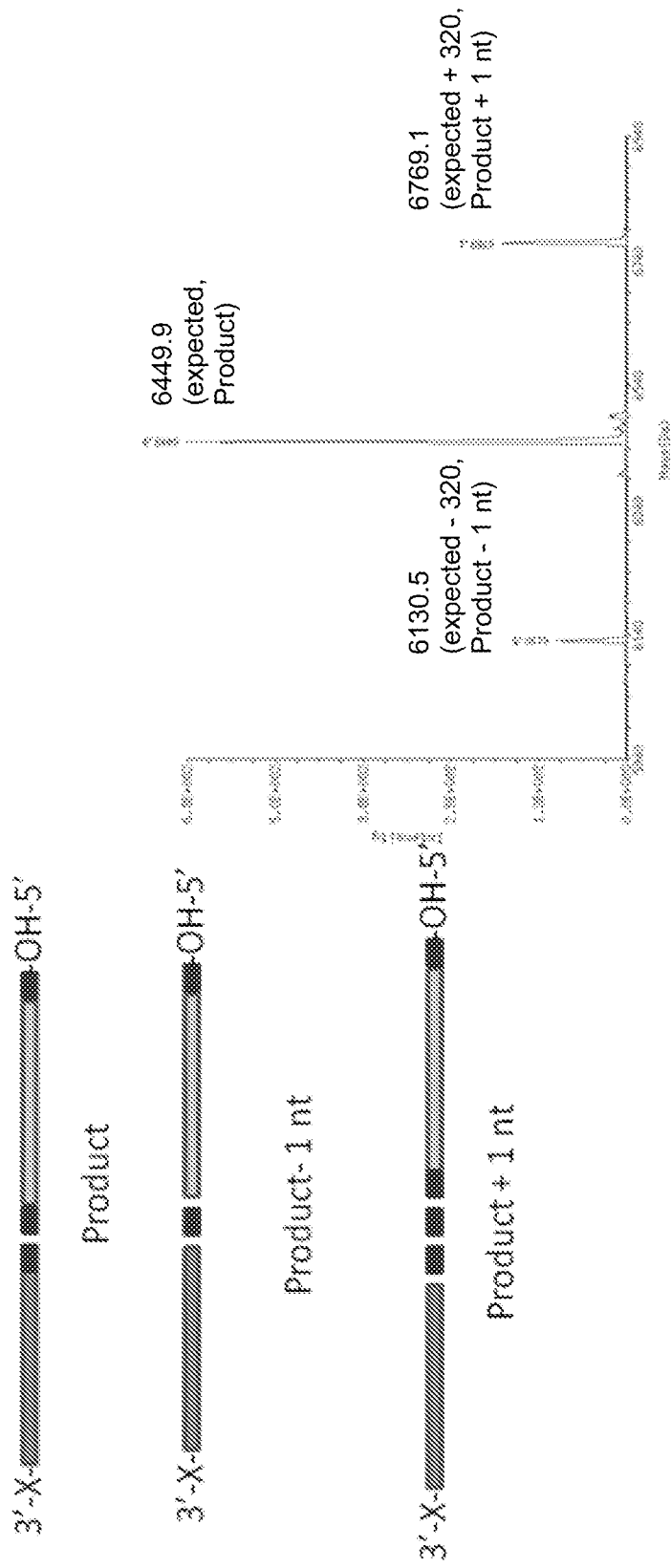

FIGS. 1-3 provide various exemplary methods for tagging libraries using single-stranded ligation with a headpiece, where tags can be ligated on the 5'-terminus or the 3'-terminus of the headpiece. To control the order in which the tags are ligated and to reduce side reactions, these methods ensure that only one reactive 5'-terminus and one reactive 3'-terminus are present during ligation. Furthermore, these exemplary methods use 2'-substituted nucleotides (e.g., mixed 2'-deoxy/2'-O-methyl nucleotides) in the tags, and these tags act as templates for a DNA- or RNA-dependent polymerase capable of polymerizing nucleotides in a template-dependent fashion. Without wishing to be limited by theory, the use of one or more 2'-substituted nucleotides (e.g., 2'-O-methyl nucleotides and/or 2'-fluoro nucleotides) within a tag could promote ligation by RNA ligase by more closely resembling RNA, while preserving both the physical and chemical robustness of the recording medium as well as the ability to extract sequence information using template-dependent polymerization.

FIG. 1 provides an exemplary method for reducing side reactions, where the ligated complex and tags are designed to avoid unwanted reactions between reactive 3'-OH and 5'-monophosphate ("5'-P") groups. In particular, this scheme depicts the phosphorylation-ligation cycle approach. During ligation, only one 3'-OH group (in the tag) and one 5'-P group (in the headpiece) are available, and, thus, only one ligation event is possible. Following the ligation and purification steps, a 5'-OH group is formed in the complex, and this group can be converted into a 5'-P for adding subsequent oligonucleotide tags. The 3'-terminus of the complex is blocked by X, which can be a protecting group or a component of a chemical entity (e.g., optionally including a linker that acts as a spacer between the chemical entity and the headpiece).

As shown in FIG. 1, the exemplary method includes ligation of building block tag 1 ("tag 1") to the 5'-terminus of the headpiece, thereby creating a complex, and performing successive ligations to the 5'-terminus of the complex.

The reactive 5'-terminus is a phosphate group on the complex, and the reactive 3'-terminus is a hydroxyl group on the tags. After the addition of each tag, the ligated complex is separated from the unreacted, unligated headpiece and tags and from other reagents (e.g., phosphate, cobalt, or other reagents present during the ligation step). Separation can be accomplished by any useful method (e.g., by chromatographic or electrophoretic separation of ligated and non-ligated products or by precipitation of a reagent). Then, the ligated complex is exposed to an agent (e.g., a polynucleotide kinase or a chemical phosphorylating agent) to form a phosphate group on the 5'-terminus of the complex. The separation and phosphorylation steps may be performed in either order. In particular, if a kinase is used in the phosphorylation step, the kinase should be inactivated or removed prior to the addition of the subsequent tags that may also contain a 5'-OH group, or any reagents that can inhibit the kinase should be removed from the reaction mixture prior to the phosphorylation step.

Figure 2A:
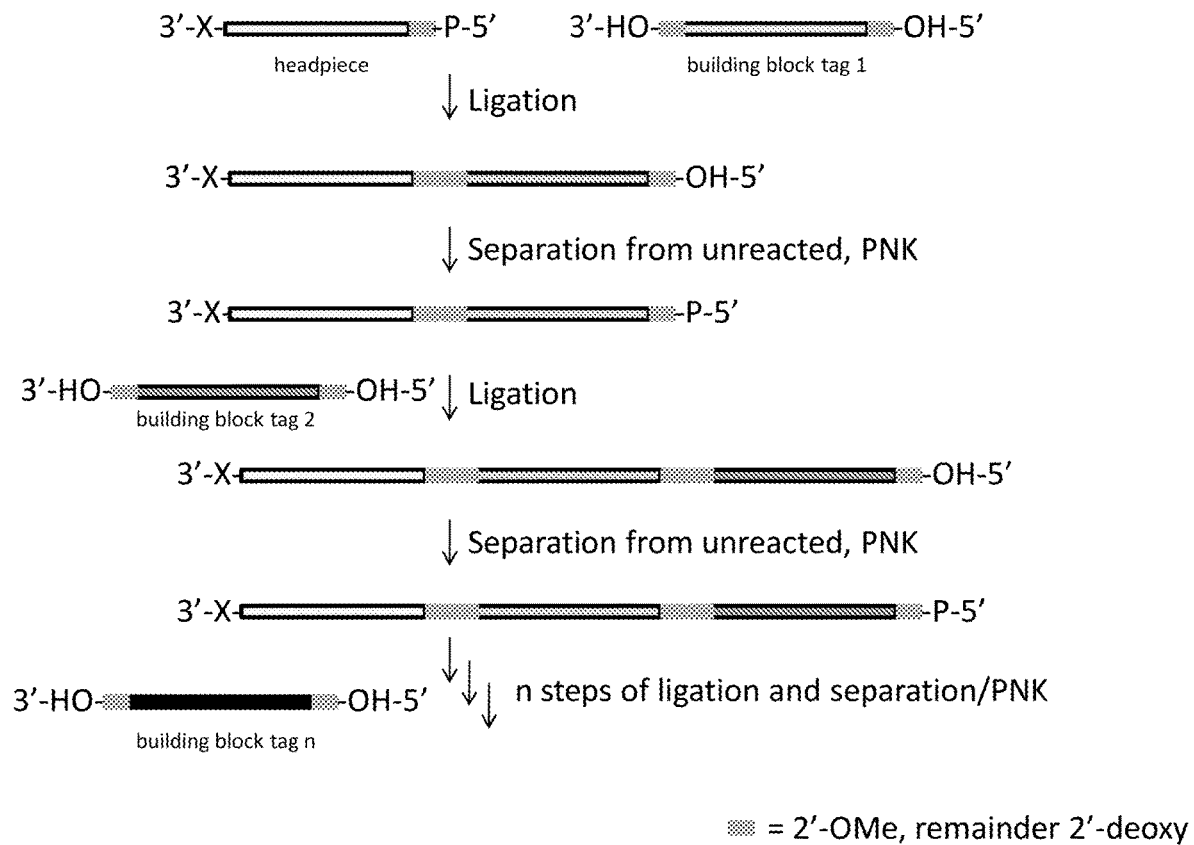
FIGS. 2A-2B show exemplary methods for single-stranded DNA tagging of libraries using enzymatic ligation.
Figure 2B:
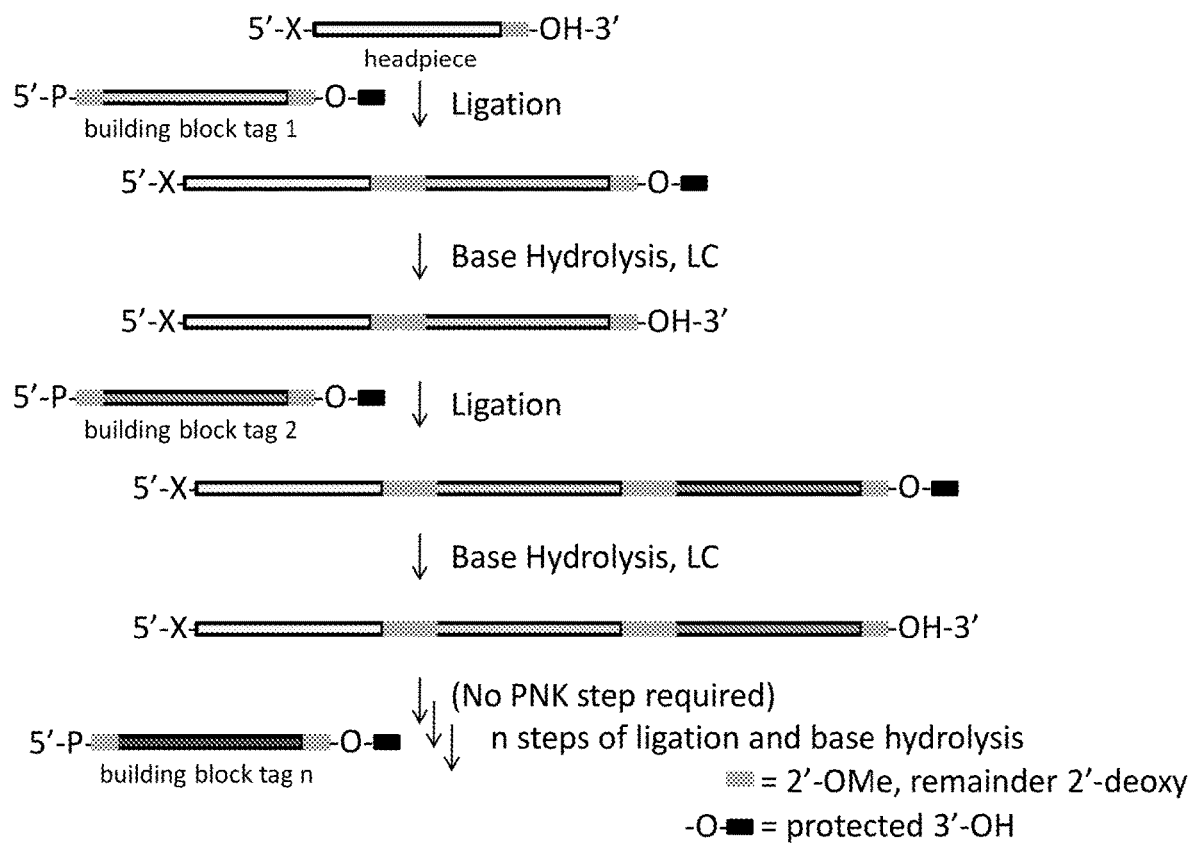

In another embodiment, the method includes binding successive tags from the 3'-terminus of the preceding ligated complex. In this method, the ligated complex lacks a reactive 3'-OH group immediately after the ligation step but contains a group that can be converted into a 3'-OH group (e.g., by release of a protecting group). FIG. 2A provides a schematic showing an exemplary method for tagging the 3'-terminus of a complex, and FIG. 2B provides an exemplary reaction scheme for a protected 3'-terminus that contains convertible 3'-OH group upon release of the 3'-linked protecting group. As shown in FIG. 2A, building block tag 1 ("tag 1") has a 3'-protected group. In the first step, the exemplary method includes ligation of the tag to the 3'-terminus of the headpiece, thereby creating a complex. Successive ligations are performed to the 3'-terminus of the complex. The reactive 5'-terminus is a phosphate group on the tag, and the reactive 3'-terminus is a hydroxyl group on the complex. After the addition of each tag, the ligated complex is deprotected (e.g., by the addition of a hydrolyzing agent) to release the 3'-protecting group.

In yet another embodiment, the method includes binding successive tags by using a 5'-preadenylated (5'-App) oligonucleotide and a ligase (e.g., T4 RNA ligase). In the presence of ATP, T4 RNA ligase will use the ATP cofactor to form an adenylated intermediate prior to ligation. In the absence of ATP, T4 RNA ligase will only ligate preadenylated oligonucleotides, and possible side reactions with 5'-P oligonucleotides will not occur. Thus, single-stranded ligation with reduced side reactions can be performed with a chemically synthesized 5'-App oligonucleotide in the presence of 5'-monophosphorylated tag, where the 5'-App oligonucleotide can be ligated to a headpiece prior to tagging or to a complex formed after multiple rounds of tagging.

FIG. 3 provides a schematic showing an exemplary method for tagging the 5'-terminus of a preadenylated headpiece. Adenylation of the donor nucleotide at the 5'-phosphate group is the first step in the ligation reaction, and this reaction generally requires one molecule of ATP. In the second step, the 3'-OH group of the acceptor oligonucleotide reacts with the adenylated donor and forms a diester bond between two oligonucleotides, thus releasing one AMP molecule. The chemically adenylated 5'-phosphate group of the donor oligonucleotide imitates a product of the first step of the ligation reaction and can be ligated to the second oligonucleotide in the absence of ATP. In the following scheme, a 5'-App headpiece is ligated to the 3'-OH group of a 5'-phosphorylated oligonucleotide tag (labeled "Tag A").

Due to the presence of the adenylated 5'-terminus of the oligonucleotide, ligation can occur in the absence of ATP. Under these conditions, the 5'-phosphate group of Tag A does not serve as a ligation donor. Building block Tag B can be ligated by providing a nucleotide having a 3'-OH terminus (labeled "Tag B") in the presence of ATP, and additional tags (labeled "Tag C") can be included.

In FIG. 3, the 3'-terminus of the headpiece can be blocked with any protecting group (e.g., an irreversible protecting group, such as ddN, or a reversible protecting group). In the first step, the method includes ligation of the tag to the 5'-terminus of the headpiece in the absence of ATP, thereby creating a complex. Successive ligations are performed to the 5'-terminus of the complex in the presence of ATP. This method can be modified in order to perform successive ligation to the 3'-terminus of a complex. For example, the method can include the use of a 5'-preadenylated tag and a headpiece having a reactive 3'-OH terminus. This method may further require blocking the 3'-terminus of the tag to avoid cross-reactions between tags, such as the method described above and in FIG. 2.

The general method provided in FIG. 3 can be modified by replacing the primer with a headpiece. In this case, the headpiece has to be adenylated chemically at the 5'-terminus, and Tag A is phosphorylated at 5'-terminus Ligation of this phosphorylated Tag A to the adenylated headpiece occurs in the same standard conditions, described herein, but omitting ATP. By using this ligation condition, the ligation of phosphorylated 5' terminus can be prevented. In the next step, ligation of Tag B requires that this tag have a free hydroxyl group at 5'-terminus (i.e., non-phosphorylated). Successive ligation reactions can be performed in the presence of ATP, followed by phosphorylation of the 5'-terminus of the resulting oligonucleotide if further extension of the tags (e.g., Tag C in FIG. 3) is desired.

The methods described herein can include any number of optional steps to diversify the library or to interrogate the members of the library. For any tagging method described herein (e.g., as in FIGS. 1-3), successive "n" number of tags can be added with additional "n" number of ligation, separation, and/or phosphorylation steps. Exemplary optional steps include restriction of library members using one or more restriction endonucleases; ligation of one or more adapter sequences to one or both of the library termini, e.g., such as one or more adapter sequences to provide a priming sequence for amplification and sequencing or to provide a label, such as biotin, for immobilization of the sequence; reverse-transcription or transcription, optionally followed by reverse-transcription, of the assembled tags in the complex using a reverse transcriptase, transcriptase, or another template-dependent polymerase; amplification of the assembled tags in the complex using, e.g., PCR; generation of clonal isolates of one or more populations of assembled tags in the complex, e.g., by use of bacterial transformation, emulsion formation, dilution, surface capture techniques, etc.; amplification of clonal isolates of one or more populations of assembled tag in the complex, e.g., by using clonal isolates as templates for template-dependent polymerization of nucleotides; and sequence determination of clonal isolates of one or more populations of assembled tags in the complex, e.g., by using clonal isolates as templates for template-dependent polymerization with fluorescently labeled nucleotides. Additional methods for amplifying and sequencing the oligonucleotide tags are described herein.

These methods can be used to identify and discover any number of chemical entities with a particular characteristic or function, e.g., in a selection step. The desired characteristic or function may be used as the basis for partitioning the library into at least two parts with the concomitant enrichment of at least one of the members or related members in the library with the desired function. In particular embodiments, the method comprises identifying a small drug-like library member that binds or inactivates a protein of therapeutic interest. In another embodiment, a sequence of chemical reactions is designed, and a set of building blocks is chosen so that the reaction of the chosen building blocks under the defined chemical conditions will generate a combinatorial plurality of molecules (or a library of molecules), where one or more molecules may have utility as a therapeutic agent for a particular protein. For example, the chemical reactions and building blocks are chosen to create a library having structural groups commonly present in kinase inhibitors. In any of these instances, the tags encode the chemical history of the library member and, in each case, a collection of chemical possibilities may be represented by any particular tag combination.

In one embodiment, the library of chemical entities, or a portion thereof, is contacted with a biological target under conditions suitable for at least one member of the library to bind to the target, followed by removal of library members that do not bind to the target, and analyzing the one or more oligonucleotide tags associated with them. This method can optionally include amplifying the tags by methods known in the art. Exemplary biological targets include enzymes (e.g., kinases, phosphatases, methylases, demethylases, proteases, and DNA repair enzymes), proteins involved in protein: protein interactions (e.g., ligands for receptors), receptor targets (e.g., GPCRs and RTKs), ion channels, bacteria, viruses, parasites, DNA, RNA, prions, and carbohydrates.

In another embodiment, the chemical entities that bind to a target are not subjected to amplification but are analyzed directly. Exemplary methods of analysis include microarray analysis, including evanescent resonance photonic crystal analysis; bead-based methods for deconvoluting tags (e.g., by using his-tags); label-free photonic crystal biosensor analysis (e.g., a BIND® Reader from SRU Biosystems, Inc., Woburn, Mass.); or hybridization-based approaches (e.g. by using arrays of immobilized oligonucleotides complementary to sequences present in the library of tags).

In addition, chemically co-reactive pairs (or functional groups) can be readily included in solid-phase oligonucleotide synthesis schemes and will support the efficient chemical ligation of oligonucleotides. In addition, the resultant ligated oligonucleotides can act as templates for template-dependent polymerization with one or more polymerases. Accordingly, any of the binding steps described herein for tagging encoded libraries can be modified to include one or more of enzymatic ligation and/or chemical ligation techniques. Exemplary ligation techniques include enzyme ligation, such as use of one of more RNA ligases and/or DNA ligases; and chemical ligation, such as use of chemically co-reactive pairs (e.g., a pair including optionally substituted alkynyl and azido functional groups).

Furthermore, one or more libraries can be combined in a split-and-mix step. In order to permit mixing of two or more libraries, the library member may contain one or more library-identifying sequences, such as in a library-identifying tag, in a ligated building block tag, or as part of the headpiece sequence, as described herein.

Methods Having Reduced Mass

Much of the motivation for single-stranded encoding strategies arises from the reduced mass of a single-stranded tag when compared to a double-stranded tag. Reduced mass potentially confers several benefits including increased solubility, decreased cost, increased reactivity, increased target accessibility, decreased hydrodynamic radius, increased accuracy of analytical assessments, etc. In addition to using a single-stranded tagging methodology, further reductions in mass can be achieved by including the use of one or more of the following: one or more tags having a reduced length, constant mass tag sets, an encoding headpiece, one or more members of a library lacking a primer binding region and/or a constant region, one or more members of a library having a reduced constant region, or any other methodologies described herein.

To minimize the mass of the members in the library, the length of one or more building block tags can be reduced, such as to a length that is as short as possible to encode each split size. In particular, the tags can be less than 20 nucleotides (e.g., less than 19 nucleotides, less than 18 nucleotides, less than 17 nucleotides, less than 16 nucleotides, less than 15 nucleotides, less than 14 nucleotides, less than 13 nucleotides, less than 12 nucleotides, less than 11 nucleotides, less than 10 nucleotides, less than 9 nucleotides, less than 8 nucleotides, or less than 7 nucleotides). As described below in the Examples, shorter tags (e.g., about 10 nucleotides or shorter) can be used for tag ligation.

Constant mass strategies can also be used, which could aid in analysis during library synthesis. In addition, constant mass tag sets could permit the recognition of all single error occurences (e.g., errors arising from misreading a sequence or from chemical or enzymatic ligation of a tag) and most multiple error occurrences. The relationship between the length of a constant mass single-stranded tag set and encoding ability (e.g., minimum lengths to support specific building block split sizes or library identities, etc.) is outlined below in Table 1. Accordingly, use of constant mass tag sets could be used to provide beneficial encoding ability, while maintaining error recognition during library formation.

TABLE 1

| Length | Base #1 | Base #2 | Base #3 | Base #4 | Combinations |
|--------|---------|---------|---------|---------|--------------|
| 1      | 1       | 0       | 0       | 0       | 1            |
| 2      | 1       | 1       | 0       | 0       | 2            |
| 3      | 1       | 1       | 1       | 0       | 6            |
| 4      | 1       | 1       | 1       | 1       | 24           |
| 5      | 2       | 1       | 1       | 1       | 60           |
| 6      | 2       | 2       | 1       | 1       | 180          |
| 7      | 2       | 2       | 2       | 1       | 630          |
| 8      | 2       | 2       | 2       | 2       | 2,520        |
| 9      | 3       | 2       | 2       | 2       | 7,560        |
| 10     | 3       | 3       | 2       | 2       | 25,200       |
| 11     | 3       | 3       | 3       | 2       | 92,400       |
| 12     | 3       | 3       | 3       | 3       | 369,600      |
| 13     | 4       | 3       | 3       | 3       | 1,201,200    |
| 14     | 4       | 4       | 3       | 3       | 4,204,200    |
| 15     | 4       | 4       | 4       | 3       | 15,765,750   |
| 16     | 4       | 4       | 4       | 4       | 63,063,000   |
| 17     | 5       | 4       | 4       | 4       | 214,414,200  |
| 18     | 5       | 5       | 4       | 4       | 771,891,120  |
| 19     | 5       | 5       | 5       | 4       | 2,933,186,256 |
| 20     | 5       | 5       | 5       | 5       | 11,732,745,024 |

To minimize mass in the library, the headpiece can be used not only to link the chemical moiety and a tag but to also encode for the identity of a particular library or for a particular step. For example, the headpiece can encode information, e.g., a plurality of headpieces that encode the first split(s) or the identity of the library, such as by using a particular sequence related to a specific library.

In addition, primer binding (e.g., constant) regions from the library of DNA-encoded chemical entities can be excluded during the selection step(s). Then, these regions can be added after selection by, e.g., single-stranded ligation. One exemplary strategy would include providing a chemical entity at the 5'-terminus of a encoding oligonucleotide, selecting a particular chemical entity based on any useful particular characteristic or function, and ligating a tailpiece oligonucleotide to the 3'-terminus of the encoding oligonucleotide that includes a primer binding sequence and may optionally contain one or more tags, e.g. a "use" tag, an "origin" tag, etc., as described herein. This primer binding sequence could then be used to initiate template-dependent polymerization to generate cDNA (or cRNA) that is complementary to the selected library member. The cDNA or cRNA would then be ligated at its 3'-terminus to an oligonucleotide that contains a primer binding sequence and, now that the encoding information is flanked on both sides by primer binding sequences, the oligonucleotide may be sequenced and/or amplified using established approaches, such as any described herein.

Mass may further be minimized by omitting or reducing the size of one or more constant sequences that separate encoding tags. Single-stranded ligation requires no complementary relationship between the ends to be ligated or between these ends and a splint. Therefore, no fixed sequence is required to support enzymatic ligation. Short fixed regions between tags may be useful for informatic parsing of tags or other in silico deconvolution processes.

Oligonucleotide Tags

The oligonucleotide tags described herein (e.g., a building block tag or a portion of a headpiece) can be used to encode any useful information, such as a molecule, a portion of a chemical entity, the addition of a component (e.g., a scaffold or a building block), a headpiece in the library, the identity of the library, the use of one or more library members (e.g., use of the members in an aliquot of a library), and/or the origin of a library member (e.g., by use of an origin sequence).

Any sequence in an oligonucleotide can be used to encode any information. Thus, one oligonucleotide sequence can serve more than one purpose, such as to encode two or more types of information or to provide a starting oligonucleotide that also encodes for one or more types of information. For example, the first building block tag can encode for the addition of a first building block, as well as for the identification of the library. In another example, a headpiece can be used to provide a starting oligonucleotide that operatively links a chemical entity to a building block tag, where the headpiece additionally includes a sequence that encodes for the identity of the library (i.e., the library-identifying sequence). Accordingly, any of the information described herein can be encoded in separate oligonucleotide tags or can be combined and encoded in the same oligonucleotide sequence (e.g., an oligonucleotide tag, such as a building block tag, or a headpiece).

A building block sequence encodes for the identity of a building block and/or the type of binding reaction conducted with a building block. This building block sequence is included in a building block tag, where the tag can optionally include one or more types of sequence described below (e.g., a library-identifying sequence, a use sequence, and/or an origin sequence).

A library-identifying sequence encodes for the identity of a particular library. In order to permit mixing of two or more libraries, a library member may contain one or more library-identifying sequences, such as in a library-identifying tag (i.e., an oligonucleotide including a library-identifying sequence), in a ligated building block tag, in a part of the headpiece sequence, or in a tailpiece sequence. These library-identifying sequences can be used to deduce encoding relationships, where the sequence of the tag is translated and correlated with chemical (synthesis) history information. Accordingly, these library-identifying sequences permit the mixing of two or more libraries together for selection, amplification, purification, sequencing, etc.

A use sequence encodes the history (i.e., use) of one or more library members in an individual aliquot of a library. For example, separate aliquots may be treated with different reaction conditions, building blocks, and/or selection steps. In particular, this sequence may be used to identify such aliquots and deduce their history (use) and thereby permit the mixing together of aliquots of the same library with different histories (uses) (e.g., distinct selection experiments) for the purposes of the mixing together of samples together for selection, amplification, purification, sequencing, etc. These use sequences can be included in a headpiece, a tailpiece, a building block tag, a use tag (i.e., an oligonucleotide including a use sequence), or any other tag described herein (e.g., a library-identifying tag or an origin tag).

An origin sequence is a degenerate (random) oligonucleotide sequence of any useful length (e.g., about six oligonucleotides) that encodes for the origin of the library member. This sequence serves to stochastically subdivide library members that are otherwise identical in all respects into entities distinguishable by sequence information, such that observations of amplification products derived from unique progenitor templates (e.g., selected library members) can be distinguished from observations of multiple amplification products derived from the same progenitor template (e.g., a selected library member). For example, after library formation and prior to the selection step, each library member can include a different origin sequence, such as in an origin tag. After selection, selected library members can be amplified to produce amplification products, and the portion of the library member expected to include the origin sequence (e.g., in the origin tag) can be observed and compared with the origin sequence in each of the other library members. As the origin sequences are degenerate, each amplification product of each library member should have a different origin sequence. However, an observation of the same origin sequence in the amplification product could indicate a source of error, such as an amplification error or a cyclization error in the sequence that produces repeated sequences, and the starting point or source of these errors can be traced by observing the origin sequence at each step (e.g., at each selection step or amplification step) of using the library. These origin sequences can be included in a headpiece, a tailpiece, a building block tag, an origin tag (i.e., an oligonucleotide including an origin sequence), or any other tag described herein (e.g., a library-identifying tag or a use tag).

Any of the types of sequences described herein can be included in the headpiece. For example, the headpiece can include one or more of a building block sequence, a library-identifying sequence, a use sequence, or an origin sequence.

Any of these sequences described herein can be included in a tailpiece. For example, the tailpiece can include one or more of a library-identifying sequence, a use sequence, or an origin sequence.

These sequences can include any modification described herein for oligonucleotides, such as one or more modifications that promote solubility in organic solvents (e.g., any described herein, such as for the headpiece), that provide an analog of the natural phosphodiester linkage (e.g., a phosphorothioate analog), or that provide one or more non-natural oligonucleotides (e.g., 2'-substituted nucleotides, such as 2'-O-methylated nucleotides and 2'-fluoro nucleotides, or any described herein).

These sequences can include any characteristics described herein for oligonucleotides. For example, these sequences can be included in tag that is less than 20 nucleotides (e.g., as described herein). In other examples, the tags including one or more of these sequences have about the same mass (e.g., each tag has a mass that is about +/−10% from the average mass between two or more tags); lack a primer binding (e.g., constant) region; lack a constant region; or have a constant region of reduced length (e.g., a length less than 30 nucleotides, less than 25 nucleotides, less than 20 nucleotides, less than 19 nucleotides, less than 18 nucleotides, less than 17 nucleotides, less than 16 nucleotides, less than 15 nucleotides, less than 14 nucleotides, less than 13 nucleotides, less than 12 nucleotides, less than 11 nucleotides, less than 10 nucleotides, less than 9 nucleotides, less than 8 nucleotides, or less than 7 nucleotides).

Sequencing strategies for libraries and oligonucleotides of this length may optionally include concatenation or catenation strategies to increase read fidelity or sequencing depth, respectively. In particular, the selection of encoded libraries that lack primer binding regions has been described in the literature for SELEX, such as described in Jarosch et al., *Nucleic Acids Res.* 34: e86 (2006), which is incorporated herein by reference. For example, a library member can be modified (e.g., after a selection step) to include a first adapter sequence on the 5'-terminus of the complex and a second adapter sequence on the 3'-terminus of the complex, where the first sequence is substantially complementary to the second sequence and result in forming a duplex. To further improve yield, two fixed dangling nucleotides (e.g., CC) are added to the 5'-terminus. In particular embodiments, the first adapter sequence is 5'-GTGCTGC-3' (SEQ ID NO: 1), and the second adapter sequence is 5'-GCAGCACCC-3' (SEQ ID NO: 2).

Headpiece

In the library, the headpiece operatively links each chemical entity to its encoding oligonucleotide tag. Generally, the headpiece is a starting oligonucleotide having two functional groups that can be further derivatized, where the first functional group operatively links the chemical entity (or a component thereof) to the headpiece and the second functional group operatively links one or more tags to the headpiece. A linker can optionally be used as a spacer between the headpiece and the chemical entity.

The functional groups of the headpiece can be used to form a covalent bond with a component of the chemical entity and another covalent bond with a tag. The component can be any part of the small molecule, such as a scaffold having diversity nodes or a building block. Alternatively, the headpiece can be derivatized to provide a linker (i.e., a spacer separating the headpiece from the small molecule to be formed in the library) terminating in a functional group (e.g., a hydroxyl, amine, carboxyl, sulfhydryl, alkynyl, azido, or phosphate group), which is used to form the covalent linkage with a component of the chemical entity. The linker can be attached to the 5'-terminus, at one of the internal positions, or to the 3'-terminus of the headpiece. When the linker is attached to one of the internal positions, the linker can be operatively linked to a derivatized base (e.g., the C5 position of uridine) or placed internally within the oligonucleotide using standard techniques known in the art. Exemplary linkers are described herein.

Figure 4A:
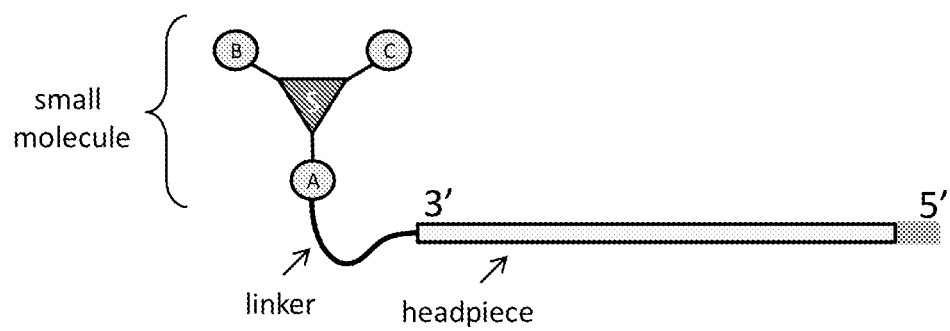
FIGS. 4A-4E show exemplary complexes, each having a headpiece, a linker, and a small molecule including a scaffold ("S") and diversity nodes A, B, and C. The dark gray boxes refer to 2'-OMe nucleotides, and the dotted lines refer to the presence of one or more complementary bases.
Figure 4B:
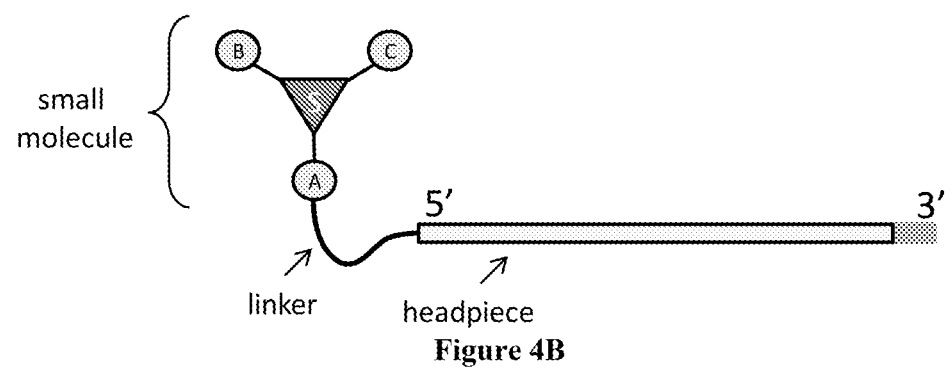
Figure 4C:
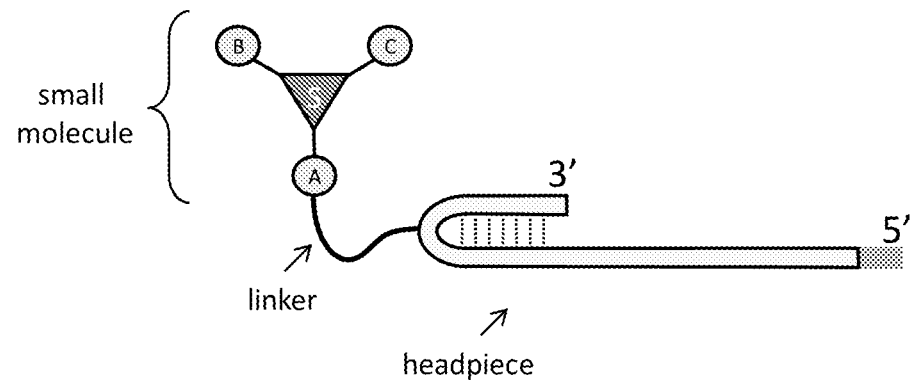
Figure 4D:
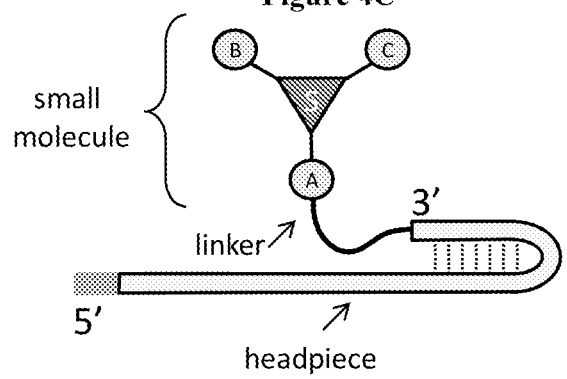

The headpiece can have any useful structure. The headpiece can be, e.g., 1 to 100 nucleotides in length, preferably 5 to 20 nucleotides in length, and most preferably 5 to 15 nucleotides in length. The headpiece can be single-stranded or double-stranded and can consist of natural or modified nucleotides, as described herein. Particular exemplary embodiments of the headpiece are described in FIGS. 4A-4D. For example, the chemical moiety can be operatively linked to the 3'-terminus (FIG. 4A) or 5'-terminus (FIG. 4B) of the headpiece. In particular embodiments, the headpiece includes a hairpin structure formed by complementary bases within the sequence. For example, the chemical moiety can be operatively linked to the internal position (FIG. 4C), the 3'-terminus (FIG. 4D), or the 5'-terminus of the headpiece.

Figure 4E:
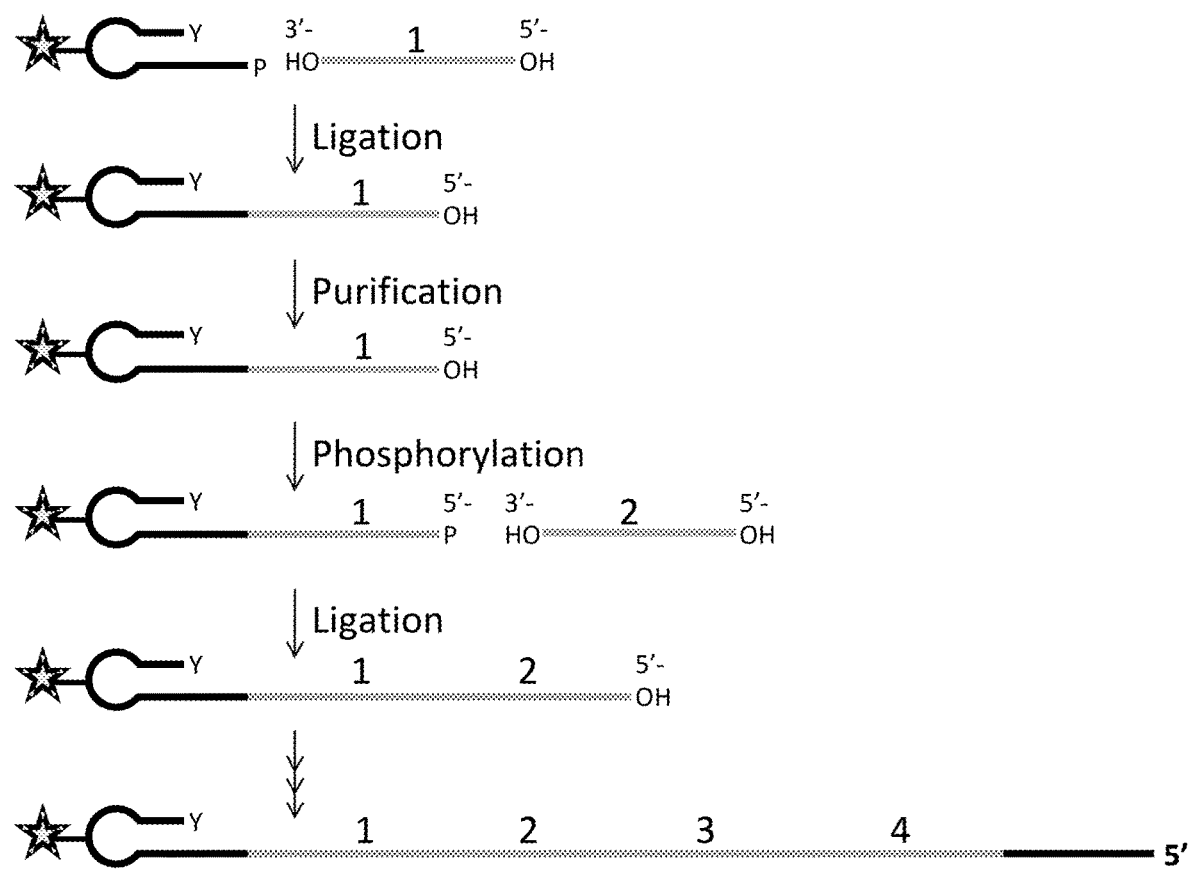

Generally, the headpiece includes a non-complementary sequence on the 5'- or 3'-terminus that allows for binding an oligonucleotide tag by polymerization, enzymatic ligation, or chemical reaction. In FIG. 4E, the exemplary headpiece allows for ligation of oligonucleotide tags (labeled 1-4), and the method includes purification and phosphorylation steps. After the addition of tag 4, an additional adapter sequence can be added to the 5'-terminus of tag 4. Exemplary adapter sequences include a primer binding sequence or a sequence having a label (e.g., biotin). In cases where many building blocks and corresponding tags are used (e.g., 100 tags), a mix-and-split strategy may be employed during the oligonucleotide synthesis step to create the necessary number of tags. Such mix-and-split strategies for DNA synthesis are known in the art. The resultant library members can be amplified by PCR following selection for binding entities versus a target(s) of interest.

The headpiece or the complex can optionally include one or more primer binding sequences. For example, the headpiece has a sequence in the loop region of the hairpin that serves as a primer binding region for amplification, where the primer binding region has a higher melting temperature for its complementary primer (e.g., which can include flanking identifier regions) than for a sequence in the headpiece. In other embodiments, the complex includes two primer binding sequences (e.g., to enable a PCR reaction) on either side of one or more tags that encode one or more building blocks. Alternatively, the headpiece may contain one primer binding sequence on the 5'- or 3'-terminus. In other embodiments, the headpiece is a hairpin, and the loop region forms a primer binding site or the primer binding site is introduced through hybridization of an oligonucleotide to the headpiece on the 3' side of the loop. A primer oligonucleotide, containing a region homologous to the 3'-terminus of the headpiece and carrying a primer binding region on its 5'-terminus (e.g., to enable a PCR reaction) may be hybridized to the headpiece and may contain a tag that encodes a building block or the addition of a building block. The primer oligonucleotide may contain additional information, such as a region of randomized nucleotides, e.g., 2 to 16 nucleotides in length, which is included for bioinformatics analysis.

The headpiece can optionally include a hairpin structure, where this structure can be achieved by any useful method. For example, the headpiece can include complementary bases that form intermolecular base pairing partners, such as by Watson-Crick DNA base pairing (e.g., adenine-thymine and guanine-cytosine) and/or by wobble base pairing (e.g., guanine-uracil, inosine-uracil, inosine-adenine, and inosine-cytosine). In another example, the headpiece can include modified or substituted nucleotides that can form higher affinity duplex formations compared to unmodified nucleotides, such modified or substituted nucleotides being known in the art. In yet another example, the headpiece includes one or more crosslinked bases to form the hairpin structure. For example, bases within a single strand or bases in different double strands can be crosslinked, e.g., by using psoralen.

The headpiece or complex can optionally include one or more labels that allow for detection. For example, the headpiece, one or more oligonucleotide tags, and/or one or more primer sequences can include an isotope, a radioimaging agent, a marker, a tracer, a fluorescent label (e.g., rhodamine or fluorescein), a chemiluminescent label, a quantum dot, and a reporter molecule (e.g., biotin or a his-tag).

In other embodiments, the headpiece or tag may be modified to support solubility in semi-, reduced-, or non-aqueous (e.g., organic) conditions. Nucleotide bases of the headpiece or tag can be rendered more hydrophobic by modifying, for example, the C5 positions of T or C bases with aliphatic chains without significantly disrupting their ability to hydrogen bond to their complementary bases. Exemplary modified or substituted nucleotides are 5'-dimethoxytrityl-N4-diisobutylaminomethylidene-5-(1-propynyl)-2'-deoxycytidine, 3'-[(2-cyanoethyl)-(N,N-diisopropyl)]-phosphoramidite; 5'-dimethoxytrityl-5-(1-propynyl)-2'-deoxyuridine, 3'-[(2-cyanoethyl)-(N,N-diisopropyl)]-phosphoramidite; 5'-dimethoxytrityl-5-fluoro-2'-deoxyuridine, 3'-[(2-cyanoethyl)-(N,N-diisopropyl)]-phosphoramidite; and 5'-dimethoxytrityl-5-(pyren-1-yl-ethynyl)-2'-deoxyuridine, or 3'-[(2-cyanoethyl)-(N,N-diisopropyl)]-phosphoramidite.

In addition, the headpiece oligonucleotide can be interspersed with modifications that promote solubility in organic solvents. For example, azobenzene phosphoramidite can introduce a hydrophobic moiety into the headpiece design. Such insertions of hydrophobic amidites into the headpiece can occur anywhere in the molecule. However, the insertion cannot interfere with subsequent tagging using additional DNA tags during the library synthesis or ensuing PCR once a selection is complete or microarray analysis, if used for tag deconvolution. Such additions to the headpiece design described herein would render the headpiece soluble in, for example, 15%, 25%, 30%, 50%, 75%, 90%, 95%, 98%, 99%, or 100% organic solvent. Thus, addition of hydrophobic residues into the headpiece design allows for improved solubility in semi- or non-aqueous (e.g., organic) conditions, while rendering the headpiece competent for oligonucleotide tagging. Furthermore, DNA tags that are subsequently introduced into the library can also be modified at the C5 position of T or C bases such that they also render the library more hydrophobic and soluble in organic solvents for subsequent steps of library synthesis.

In particular embodiments, the headpiece and the first building block tag can be the same entity, i.e., a plurality of headpiece-tag entities can be constructed that all share common parts (e.g., a primer binding region) and all differ in another part (e.g., encoding region). These may be utilized in the "split" step and pooled after the event they are encoding has occurred.

In particular embodiments, the headpiece can encode information, e.g., by including a sequence that encodes the first split(s) step or a sequence that encodes the identity of the library, such as by using a particular sequence related to a specific library.

Enzymatic Ligation and Chemical Ligation Techniques

Various ligation techniques can be used to add scaffolds, building blocks, linkers, building block tags, and/or the headpiece to produce a complex. Accordingly, any of the binding steps described herein can include any useful ligation techniques, such as enzyme ligation and/or chemical ligation. These binding steps can include the addition of one or more building block tags to the headpiece or complex; the addition of a linker to the headpiece; and the addition of one or more scaffolds or building blocks to the headpiece or complex. In particular embodiments, the ligation techniques used for any oligonucleotide provide a resultant product that can be transcribed and/or reverse transcribed to allow for decoding of the library or for template-dependent polymerization with one or more DNA or RNA polymerases.

Generally, enzyme ligation produces an oligonucleotide having a native phosphodiester bond that can be transcribed and/or reverse transcribed. Exemplary methods of enzyme ligation are provided herein and include the use of one or more RNA or DNA ligases, such as T4 RNA ligase, T4 DNA ligase, CircLigase™ ssDNA ligase, CircLigase™ II ssDNA ligase, and ThermoPhage™ ssDNA ligase (Prokazyme Ltd., Reykjavik, Iceland).

Chemical ligation can also be used to produce oligonucleotides capable of being transcribed or reverse transcribed. One benefit of chemical ligation is that solid phase synthesis of such oligonucleotides can be optimized to support efficient ligation yield. However, the efficacy of a chemical ligation technique to provide oligonucleotides capable of being transcribed or reverse transcribed may need to be tested. This efficacy can be tested by any useful method, such as liquid chromatography-mass spectrometry, RT-PCR analysis, and/or PCR analysis. Examples of these methods are provided in Example 5.

In particular embodiments, chemical ligation includes the use of one or more chemically co-reactive pairs to provide a spacer that can be transcribed or reverse transcribed. In particular, reactions suitable for chemically co-reactive pairs are preferred candidates for the cyclization process (Kolb et al., $Angew.$ $Chem.$ $Int.$ $Ed.$, 40:2004-2021 (2001); Van der Eycken et al., $QSAR$ $Comb.$ $Sci.$, 26:1115-1326 (2007)). Exemplary chemically co-reactive pairs are a pair including an optionally substituted alkynyl group and an optionally substituted azido group to form a triazole spacer via a Huisgen 1,3-dipolar cycloaddition reaction; an optionally substituted diene having a $4\pi$ electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and an optionally substituted dienophile or an optionally substituted heterodienophile having a $2\pi$ electron system (e.g., an optionally substituted alkenyl group or an optionally substituted alkynyl group) to form a cycloalkenyl spacer via a Diels-Alder reaction; a nucleophile (e.g., an optionally substituted amine or an optionally substituted thiol) with a strained heterocyclyl electrophile (e.g., optionally substituted epoxide, aziridine, aziridinium ion, or episulfonium ion) to form a heteroalkyl spacer via a ring opening reaction; a phosphorothioate group with an iodo group, such as in a splinted ligation of an oligonucleotide containing 5'-iodo dT with a 3'-phosphorothioate oligonucleotide; and an aldehyde group and an amino group, such as a reaction of a 3'-aldehyde-modified oligonucleotide, which can optionally be obtained by oxidizing a commercially available 3'-glyceryl-modified oligonucleotide, with 5'-amino oligonucleotide (i.e., in a reductive amination reaction) or a 5'-hydrazido oligonucleotide.

In other embodiments, chemical ligation includes introducing an analog of the phosphodiester bond, e.g., for post-selection PCR analysis and sequencing. Exemplary analogs of a phosphodiester include a phosphorothioate linkage (e.g., as introduced by use of a phosphorothioate group and a leaving group, such as an iodo group), a phosphoramide linkage, or a phosphorodithioate linkage (e.g., as introduced by use of a phosphorodithioate group and a leaving group, such as an iodo group).

Reaction Conditions to Promote Enzymatic Ligation or Chemical Ligation

The invention also features one or more reaction conditions that promote enzymatic or chemical ligation between the headpiece and a tag or between two tags. These reaction conditions include using modified nucleotides within the tag, as described herein; using donor tags and acceptor tags having different lengths and varying the concentration of the tags; using different types of ligases, as well as combinations thereof (e.g., CircLigase™ DNA ligase and/or T4 RNA ligase), and varying their concentration; using poly ethylene glycols (PEGs) having different molecular weights and varying their concentration; use of non-PEG crowding agents (e.g., betaine or bovine serum albumin); varying the temperature and duration for ligation; varying the concentration of various agents, including ATP, $Co(NH_3)_6Cl_3$, and yeast inorganic pyrophosphate; using enzymatically or chemically phosphorylated oligonucleotide tags; using 3'-protected tags; and using preadenylated tags. These reaction conditions also include chemical ligations.

The headpiece and/or tags can include one or more modified or substituted nucleotides. In preferred embodiments, the headpiece and/or tags include one or more modified or substituted nucleotides that promote enzymatic ligation, such as 2'-O-methyl nucleotides (e.g., 2'-O-methyl guanine or 2'-O-methyl uracil), 2'-fluoro nucleotides, or any other modified nucleotides that are utilized as a substrate for ligation. Alternatively, the headpiece and/or tags are modified to include one or more chemically reactive groups to support chemical ligation (e.g. an optionally substituted alkynyl group and an optionally substituted azido group). Optionally, the tag oligonucleotides are functionalized at both termini with chemically reactive groups, and, optionally, one of these termini is protected, such that the groups may be addressed independently and side-reactions may be reduced (e.g., reduced polymerization side-reactions).

Enzymatic ligation can include one or more ligases. Exemplary ligases include CircLigase™ ssDNA ligase (EPI-CENTRE Biotechnologies, Madison, Wis.), CircLigase™ II ssDNA ligase (also from EPICENTRE Biotechnologies), ThermoPhage™ ssDNA ligase (Prokazyme Ltd., Reykjavik, Iceland), T4 RNA ligase, and T4 DNA ligase. In preferred embodiments, ligation includes the use of an RNA ligase or a combination of an RNA ligase and a DNA ligase. Ligation can further include one or more soluble multivalent cations, such as $Co(NH_3)_6Cl_3$, in combination with one or more ligases.

Before or after the ligation step, the complex can be purified for three reasons. First, the complex can be purified to remove unreacted headpiece or tags that may result in cross-reactions and introduce "noise" into the encoding process. Second, the complex can be purified to remove any reagents or unreacted starting material that can inhibit or lower the ligation activity of a ligase. For example, phosphate may result in lowered ligation activity. Third, entities that are introduced into a chemical or ligation step may need to be removed to enable the subsequent chemical or ligation step. Methods of purifying the complex are described herein.

Enzymatic and chemical ligation can include poly ethylene glycol having an average molecular weight of more than 300 Daltons (e.g., more than 600 Daltons, 3,000 Daltons, 4,000 Daltons, or 4,500 Daltons). In particular embodiments, the poly ethylene glycol has an average molecular weight from about 3,000 Daltons to 9,000 Daltons (e.g., from 3,000 Daltons to 8,000 Daltons, from 3,000 Daltons to 7,000 Daltons, from 3,000 Daltons to 6,000 Daltons, and from 3,000 Daltons to 5,000 Daltons). In preferred embodiments, the poly ethylene glycol has an average molecular weight from about 3,000 Daltons to about 6,000 Daltons (e.g., from 3,300 Daltons to 4,500 Daltons, from 3,300 Daltons to 5,000 Daltons, from 3,300 Daltons to 5,500 Daltons, from 3,300 Daltons to 6,000 Daltons, from 3,500 Daltons to 4,500 Daltons, from 3,500 Daltons to 5,000 Daltons, from 3,500 Daltons to 5,500 Daltons, and from 3,500 Daltons to 6,000 Daltons, such as 4,600 Daltons). Poly ethylene glycol can be present in any useful amount, such as from about 25% (w/v) to about 35% (w/v), such as 30% (w/v).

In a preferred embodiment of this invention, the building block tags are installed by ligation of a single-stranded oligonucleotide to a single-stranded oligonucleotide using the ligation protocol outlined below:

Headpiece: 25 µM (5' terminus: 5'-monophospho/2'-OMe G, intervening nucleotides: 2'-deoxy, and 3' terminus: 2'-blocked/3'-blocked)
Building Block Tag: 25 µM (5'-terminus: 2'-OMe/5'-OH G, intervening nucleotides: 2'-deoxy, and 3'-terminus: 3'-OH/2'-OMe)
$Co(NH_3)_6Cl_3$: 1 mM
PEG 4600: 30% (w/v)
T4 RNA Ligase (Promega): 1.5 units/µl
Yeast Inorganic Pyrophosphatase: 0.0025 units/µl
Tris: 50 mM
$MgCl_2$: 10 mM
ATP: 1 mM
pH: 7.5
Water: Balance In further embodiments, the protocol includes incubation at 37° C. for 20 hours. For the purposes of actual library construction, higher concentration of headpiece, tags, and/or ligase may be used, and such modifications to these concentrations would be apparent to those skilled in the art.

Methods for Encoding Chemical Entities within a Library

The methods of the invention can be used to synthesize a library having a diverse number of chemical entities that are encoded by oligonucleotide tags. Examples of building blocks and encoding DNA tags are found in U.S. Patent Application Publication No. 2007/0224607, hereby incorporated by reference.

Each chemical entity is formed from one or more building blocks and optionally a scaffold. The scaffold serves to provide one or more diversity nodes in a particular geometry (e.g., a triazine to provide three nodes spatially arranged around a heteroaryl ring or a linear geometry).

The building blocks and their encoding tags can be added directly or indirectly (e.g., via a linker) to the headpiece to form a complex. When the headpiece includes a linker, the building block or scaffold is added to the end of the linker. When the linker is absent, the building block can be added directly to the headpiece or the building block itself can include a linker that reacts with a functional group of the headpiece. Exemplary linkers and headpieces are described herein.

The scaffold can be added in any useful way. For example, the scaffold can be added to the end of the linker or the headpiece, and successive building blocks can be added to the available diversity nodes of the scaffold. In another example, building block $A_n$ is first added to the linker or the headpiece, and then the diversity node of scaffold S is reacted with a functional group in building block $A_n$. Oligonucleotide tags encoding a particular scaffold can optionally be added to the headpiece or the complex. For example, $S_n$ is added to the complex in n reaction vessels, where n is an integer more than one, and tag $S_n$ (i.e., tag $S_1, S_2, \ldots S_{n-1}, S_n$) is bound to the functional group of the complex.

Building blocks can be added in multiple, synthetic steps. For example, an aliquot of the headpiece, optionally having an attached linker, is separated into n reaction vessels, where n is an integer of two or greater. In the first step, building block $A_n$ is added to each n reaction vessel (i.e., building block $A_1, A_2, \ldots A_{n-1}, A_n$ is added to reaction vessel 1, 2, \ldots n-1, n), where n is an integer and each building block $A_n$ is unique. In the second step, scaffold S is added to each reaction vessel to form an $A_n$-S complex. Optionally, scaffold $S_n$ can be added to each reaction vessel to from an $A_n$-$S_n$ complex, where n is an integer of more than two, and each scaffold $S_n$ can be unique. In the third step, building block $B_n$ is to each n reaction vessel containing the $A_n$-S complex (i.e., building block $B_1, B_2, \ldots B_{n-1}, B_n$ is added to reaction vessel 1, 2, \ldots n-1, n containing the $A_1$-S, $A_2$-S, \ldots $A_{n-1}$-S, $A_n$-S complex), where each building block $B_n$ is unique. In further steps, building block $C_n$ can be added to each n reaction vessel containing the $B_n$-$A_n$-S complex (i.e., building block $C_1, C_2, \ldots C_{n-1}, C_n$ is added to reaction vessel 1, 2, \ldots n-1, n containing the $B_1$-$A_1$-S \ldots $B_n$-$A_n$-S complex), where each building block $C_n$ is unique. The resulting library will have $n^3$ number of complexes having $n^3$ tags. In this manner, additional synthetic steps can be used to bind additional building blocks to further diversify the library.

After forming the library, the resultant complexes can optionally be purified and subjected to a polymerization or ligation reaction using one or more primers. This general strategy can be expanded to include additional diversity nodes and building blocks (e.g., D, E, F, etc.). For example, the first diversity node is reacted with building blocks and/or S and encoded by an oligonucleotide tag. Then, additional building blocks are reacted with the resultant complex, and the subsequent diversity node is derivatized by additional building blocks, which is encoded by the primer used for the polymerization or ligation reaction To form an encoded library, oligonucleotide tags are added to the complex after or before each synthetic step. For example, before or after the addition of building block $A_n$ to each reaction vessel, tag $A_n$ is bound to the functional group of the headpiece (i.e., tag $A_1, A_2, \ldots A_{n-1}, A_n$ is added to reaction vessel 1, 2, \ldots n-1, n containing the headpiece). Each tag $A_n$ has a distinct sequence that correlates with each unique building block $A_n$, and determining the sequence of tag $A_n$ provides the chemical structure of building block $A_n$. In this manner, additional tags are used to encode for additional building blocks or additional scaffolds.

Furthermore, the last tag added to the complex can either include a primer sequence or provide a functional group to allow for binding (e.g., by ligation) of a primer sequence. The primer sequence can be used for amplifying and/or sequencing the oligonucleotides tags of the complex. Exemplary methods for amplifying and for sequencing include polymerase chain reaction (PCR), linear chain amplification (LCR), rolling circle amplification (RCA), or any other method known in the art to amplify or determine nucleic acid sequences.

Using these methods, large libraries can be formed having a large number of encoded chemical entities. For example, a headpiece is reacted with a linker and building block $A_n$, which includes 1,000 different variants (i.e., n=1,000). For each building block $A_n$, a DNA tag $A_n$ is ligated or primer extended to the headpiece. These reactions may be performed in a 1,000-well plate or 10×100 well plates. All reactions may be pooled, optionally purified, and split into a second set of plates. Next, the same procedure may be performed with building block $B_n$, which also include 1,000 different variants. A DNA tag $B_n$ may be ligated to the $A_n$ complex, and all reactions may be pooled. The resultant library includes 1,000×1,000 combinations of $A_n$×$B_n$ (i.e., 1,000,000 compounds) tagged by 1,000,000 different combinations of tags. The same approach may be extended to add building blocks $C_n, D_n, E_n$, etc. The generated library may then be used to identify compounds that bind to the target. The structure of the chemical entities that bind to the library can optionally be assessed by PCR and sequencing of the DNA tags to identify the compounds that were enriched.

This method can be modified to avoid tagging after the addition of each building block or to avoid pooling (or mixing). For example, the method can be modified by adding building block $A_n$ to n reaction vessels, where n is an integer of more than one, and adding the identical building block $B_1$ to each reaction well. Here, $B_1$ is identical for each chemical entity, and, therefore, an oligonucleotide tag encoding this building block is not needed. After adding a building block, the complexes may be pooled or not pooled. For example, the library is not pooled following the final step of building block addition, and the pools are screened individually to identify compound(s) that bind to a target. To avoid pooling all of the reactions after synthesis, a BIND® Reader (from SRU Biosystems, Inc.), for example, may be used to monitor binding on a sensor surface in high throughput format (e.g., 384 well plates and 1,536 well plates). For example, building block $A_n$ may be encoded with DNA tag $A_n$, and building block $B_n$ may be encoded by its position within the well plate. Candidate compounds can then be identified by using a binding assay (e.g., using a BIND® Biosensor, also available by SRU Biosystems, Inc., or using an ELISA assay) and by analyzing the $A_n$ tags by sequencing, microarray analysis and/or restriction digest analysis. This analysis allows for the identification of combinations of building blocks $A_n$ and $B_n$ that produce the desired molecules.

The method of amplifying can optionally include forming a water-in-oil emulsion to create a plurality of aqueous microreactors. The reaction conditions (e.g., concentration of complex and size of microreactors) can be adjusted to provide, on average, a microreactor having at least one member of a library of compounds. Each microreactor can also contain the target, a single bead capable of binding to a complex or a portion of the complex (e.g., one or more tags) and/or binding the target, and an amplification reaction solution having one or more necessary reagents to perform nucleic acid amplification. After amplifying the tag in the microreactors, the amplified copies of the tag will bind to the beads in the microreactors, and the coated beads can be identified by any useful method.

Once the building blocks from the first library that bind to the target of interest have been identified, a second library may be prepared in an iterative fashion. For example, one or two additional nodes of diversity can be added, and the second library is created and sampled, as described herein. This process can be repeated as many times as necessary to create molecules with desired molecular and pharmaceutical properties.

Various ligation techniques can be used to add the scaffold, building blocks, linkers, and building block tags. Accordingly, any of the binding steps described herein can include any useful ligation technique or techniques. Exemplary ligation techniques include enzymatic ligation, such as use of one of more RNA ligases and/or DNA ligases, as described herein; and chemical ligation, such as use of chemically co-reactive pairs, as described herein.

Scaffold and Building Blocks

The scaffold S can be a single atom or a molecular scaffold. Exemplary single atom scaffolds include a carbon atom, a boron atom, a nitrogen atom, or a phosphorus atom, etc. Exemplary polyatomic scaffolds include a cycloalkyl group, a cycloalkenyl group, a heterocycloalkyl group, a heterocycloalkenyl group, an aryl group, or a heteroaryl group. Particular embodiments of a heteroaryl scaffold include a triazine, such as 1,3,5-triazine, 1,2,3-triazine, or 1,2,4-triazine; a pyrimidine; a pyrazine; a pyridazine; a furan; a pyrrole; a pyrrolline; a pyrrolidine; an oxazole; a pyrazole; an isoxazole; a pyran; a pyridine; an indole; an indazole; or a purine.

The scaffold S can be operatively linked to the tag by any useful method. In one example, S is a triazine that is linked directly to the headpiece. To obtain this exemplary scaffold, trichlorotriazine (i.e., a chlorinated precursor of triazine having three chlorines) is reacted with a nucleophilic group of the headpiece. Using this method, S has three positions having chlorine that are available for substitution, where two positions are available diversity nodes and one position is attached to the headpiece. Next, building block $A_n$ is added to a diversity node of the scaffold, and tag $A_n$ encoding for building block $A_n$ ("tag $A_n$") is ligated to the headpiece, where these two steps can be performed in any order. Then, building block $B_n$ is added to the remaining diversity node, and tag $B_n$ encoding for building block $B_n$ is ligated to the end of tag $A_n$. In another example, S is a triazine that is operatively linked to the linker of a tag, where trichlorotriazine is reacted with a nucleophilic group (e.g., an amino group) of a PEG, aliphatic, or aromatic linker of a tag. Building blocks and associated tags can be added, as described above.

In yet another example, S is a triazine that is operatively linked to building block $A_n$. To obtain this scaffold, building block $A_n$ having two diversity nodes (e.g., an electrophilic group and a nucleophilic group, such as an Fmoc-amino acid) is reacted with the nucleophilic group of a linker (e.g., the terminal group of a PEG, aliphatic, or aromatic linker, which is attached to a headpiece). Then, trichlorotriazine is reacted with a nucleophilic group of building block $A_n$. Using this method, all three chlorine positions of S are used as diversity nodes for building blocks. As described herein, additional building blocks and tags can be added, and additional scaffolds $S_n$ can be added.

Exemplary building block $A_n$'s include, e.g., amino acids (e.g., alpha-, beta-, gamma-, delta-, and epsilon-amino acids, as well as derivatives of natural and unnatural amino acids), chemically co-reactive reactants (e.g., azide or alkyne chains) with an amine, or a thiol reactant, or combinations thereof. The choice of building block $A_n$ depends on, for example, the nature of the reactive group used in the linker, the nature of a scaffold moiety, and the solvent used for the chemical synthesis.

Exemplary building block $B_n$'s and $C_n$'s include any useful structural unit of a chemical entity, such as optionally substituted aromatic groups (e.g., optionally substituted phenyl or benzyl), optionally substituted heterocyclyl groups (e.g., optionally substituted quinolinyl, isoquinolinyl, indolyl, isoindolyl, azaindolyl, benzimidazolyl, azabenzimidazolyl, benzisoxazolyl, pyridinyl, piperidyl, or pyrrolidinyl), optionally substituted alkyl groups (e.g., optionally substituted linear or branched $C_{1-6}$ alkyl groups or optionally substituted $C_{1-6}$ aminoalkyl groups), or optionally substituted carbocyclyl groups (e.g., optionally substituted cyclopropyl, cyclohexyl, or cyclohexenyl). Particularly useful building block $B_n$'s and $C_n$'s include those with one or more reactive groups, such as an optionally substituted group (e.g., any described herein) having one or optional substituents that are reactive groups or can be chemically modified to form reactive groups. Exemplary reactive groups include one or more of amine (—$NR_2$, where each R is, independently, H or an optionally substituted $C_{1-6}$ alkyl), hydroxy, alkoxy (—OR, where R is an optionally substituted $C_{1-6}$ alkyl, such as methoxy), carboxy (—COOH), amide, or chemically co-reactive substituents. A restriction site may be introduced, for example, in tag $B_n$ or $C_n$, where a complex can be identified by performing PCR and restriction digest with one of the corresponding restriction enzymes.

Linkers

The bifunctional linker between the headpiece and the chemical entity can be varied to provide an appropriate spacer and/or to increase the solubility of the headpiece in organic solvent. A wide variety of linkers are commercially available that can couple the headpiece with the small molecule library. The linker typically consists of linear or branched chains and may include a $C_{1-10}$ alkyl, a heteroalkyl of 1 to 10 atoms, a $C_{2-10}$ alkenyl, a $C_{2-10}$ alkynyl, $C_{5-10}$ aryl, a cyclic or polycyclic system of 3 to 20 atoms, a phosphodiester, a peptide, an oligosaccharide, an oligonucleotide, an oligomer, a polymer, or a poly alkyl glycol (e.g., a poly ethylene glycol, such as —$(CH_2CH_2O)_nCH_2CH_2$—, where n is an integer from 1 to 50), or combinations thereof.

The bifunctional linker may provide an appropriate spacer between the headpiece and a chemical entity of the library. In certain embodiments, the bifunctional linker includes three parts. Part 1 may be a reactive group, which forms a covalent bond with DNA, such as, e.g., a carboxylic acid, preferably activated by a N-hydroxy succinimide (NHS) ester to react with an amino group on the DNA (e.g., amino-modified dT), an amidite to modify the 5' or 3'-terminus of a single-stranded headpiece (achieved by means of standard oligonucleotide chemistry), chemically co-reactive pairs (e.g., azido-alkyne cycloaddition in the presence of Cu(I) catalyst, or any described herein), or thiol reactive groups. Part 2 may also be a reactive group, which forms a covalent bond with the chemical entity, either building block $A_n$ or a scaffold. Such a reactive group could be, e.g., an amine, a thiol, an azide, or an alkyne. Part 3 may be a chemically inert spacer of variable length, introduced between Part 1 and 2. Such a spacer can be a chain of ethylene glycol units (e.g., PEGs of different lengths), an alkane, an alkene, a polyene chain, or a peptide chain. The linker can contain branches or inserts with hydrophobic moieties (such as, e.g., benzene rings) to improve solubility of the headpiece in organic solvents, as well as fluorescent moieties (e.g. fluorescein or Cy-3) used for library detection purposes. Hydrophobic residues in the headpiece design may be varied with the linker design to facilitate library synthesis in organic solvents. For example, the headpiece and linker combination is designed to have appropriate residues wherein the octanol:water coefficient ($P_{oct}$) is from, e.g., 1.0 to 2.5.

Linkers can be empirically selected for a given small molecule library design, such that the library can be synthesized in organic solvent, for example, in 15%, 25%, 30%, 50%, 75%, 90%, 95%, 98%, 99%, or 100% organic solvent. The linker can be varied using model reactions prior to library synthesis to select the appropriate chain length that solubilizes the headpiece in an organic solvent. Exemplary linkers include those having increased alkyl chain length, increased poly ethylene glycol units, branched species with positive charges (to neutralize the negative phosphate charges on the headpiece), or increased amounts of hydrophobicity (for example, addition of benzene ring structures).

Examples of commercially available linkers include amino-carboxylic linkers, such as those being peptides (e.g., Z-Gly-Gly-Gly-Osu (N-alpha-benzyloxycarbonyl-(Glycine)$_3$-N-succinimidyl ester) or Z-Gly-Gly-Gly-Gly-Gly-Gly-Osu (N-alpha-benzyloxycarbonyl-(Glycine)$_6$-N-succinimidyl ester, SEQ ID NO: 3)), PEG (e.g., Fmoc-aminoPEG2000-NHS or amino-PEG (12-24)-NHS), or alkane acid chains (e.g., Boc-ε-aminocaproic acid-Osu); chemically co-reactive pair linkers, such as those chemically co-reactive pairs described herein in combination with a peptide moiety (e.g., azidohomoalanine-Gly-Gly-Gly-OSu (SEQ ID NO: 4) or propargylglycine-Gly-Gly-Gly-OSu (SEQ ID NO: 5)), PEG (e.g., azido-PEG-NHS), or an alkane acid chain moiety (e.g., 5-azidopentanoic acid, (S)-2-(azidomethyl)-1-Boc-pyrrolidine, 4-azidoaniline, or 4-azidobutan-1-oic acid N-hydroxysuccinimide ester); thiol-reactive linkers, such as those being PEG (e.g., SM(PEG)n NHS-PEG-maleimide), alkane chains (e.g., 3-(pyridin-2-yldisulfanyl)-propionic acid-Osu or sulfosuccinimidyl 6-(3'-[2-pyridyldithio]-propionamido)hexanoate)); and amidites for oligonucleotide synthesis, such as amino modifiers (e.g., 6-(trifluoroacetylamino)-hexyl-(2-cyanoethyl)-(N,N-diisopropyl)-phosphoramidite), thiol modifiers (e.g., 5-trityl-6-mercaptohexyl-1-[(2-cyanoethyl)-(N,N-diisopropyl)]-phosphoramidite, or chemically co-reactive pair modifiers (e.g., 6-hexyn-1-yl-(2-cyanoethyl)-(N,N-diisopropyl)-phosphoramidite, 3-dimethoxytrityloxy-2-(3-(3-propargyloxypropanamido)propanamido)propyl-1-O-succinoyl, long chain alkylamino CPG, or 4-azido-butan-1-oic acid N-hydroxysuccinimide ester)). Additional linkers are known in the art, and those that can be used during library synthesis include, but are not limited to, 5'-O-dimethoxytrityl-1',2'-dideoxyribose-3'-[(2-cyanoethyl)-(N,N-diisopropyl)]-phosphoramidite; 9-O-dimethoxytrityl-triethylene glycol, 1[(2-cyanoethyl)-(N,N-diisopropyl)]-phosphoramidite; 3-(4,4'-dimethoxytrityloxy)propyl-1-[(2-cyanoethyl)-(N,N-diisopropyl)]-phosphoramidite; and 18-O-dimethoxytrityl hexaethyleneglycol, 1-[(2-cyanoethyl)-(N,N-diisopropyl)]-phosphoramidite. Any of the linkers herein can be added in tandem to one another in different combinations to generate linkers of different desired lengths.

Linkers may also be branched, where branched linkers are well known in the art and examples can consist of symmetric or asymmetric doublers or a symmetric trebler. See, for example, Newcome et al., Dendritic Molecules: Concepts, Synthesis, Perspectives, VCH Publishers (1996); Boussif et al., *Proc. Natl. Acad. Sci. USA* 92:7297-7301 (1995); and Jansen et al., *Science* 266:1226 (1994).

Example 1

General Strategy to Improve Single-Stranded Ligation of DNA Tags

Various reaction conditions were explored to improve single-stranded ligation of tags to form an encoded library. These reaction conditions included using modified nucleotides within the tag (e.g., use of one or more nucleotides having a 2'-OMe group to form a MNA/DNA tag, where "MNA" refers to an oligonucleotide having at least one 2'-O-methyl nucleotide); using donor tags and acceptor tags having different lengths and varying the concentration of the tags; using different types of ligases, as well as combinations thereof (e.g., CircLigase™ ssDNA ligase and/or T4 RNA ligase), and varying their concentration; purifying the complex by removing unreacted starting materials; using poly ethylene glycols (PEGs) having different molecular weights and varying their concentration; varying the temperature and duration for reaction, such as ligation; varying the concentration of various agents, including ATP, Co(NH$_3$)$_6$Cl$_3$, and yeast inorganic pyrophosphate; using enzymatically or chemically phosphorylated oligonucleotide tags; using 3'-protected tags; and using 5'-chemically adenylated tags.

Figure 5A:
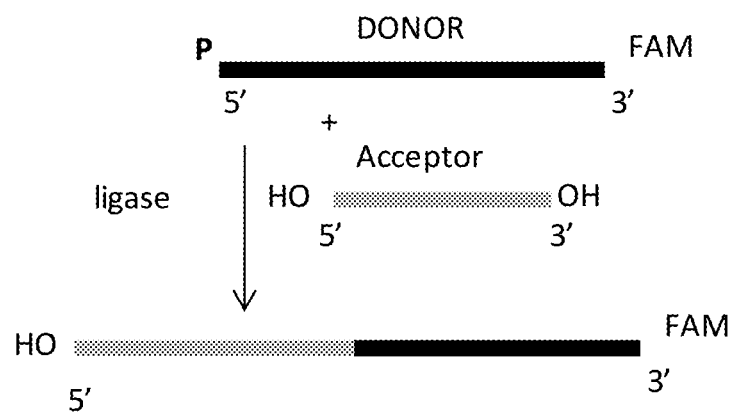
FIGS. 5A-5C show oligonucleotide ligation by T4 RNA ligase or CircLigase™ ssDNA ligase.
Figure 5B:
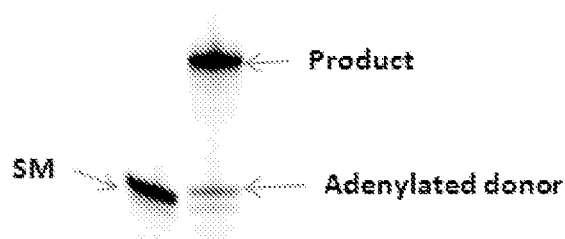

After a thorough analysis of different conditions, optimal combinations of parameters that provided up to 90% ligation efficiency (e.g., FIG. 5C), as determined by the fraction of ligated final product to un-ligated starting reactant ("fraction ligated"), were found. A scheme of the ligation reaction using ligase is shown in FIG. 5A, and a typical denaturing polyacrylamide gel electrophoresis is shown in FIG. 5B. The donor oligonucleotide was labeled at the 3'-terminus and could be detected on a gel by scanning at 450 nm excitation on a Storm™ 800 PhosphorImager. The gel depicts an unligated donor (or starting material) and the ligated product. In particular, the adenylated donor can be resolved and distinguished from the starting material on this gel.

Table 2 provides ligation efficiencies measured as a function of the composition of the oligonucleotide (i.e., oligonucleotides with all DNA nucleotides versus oligonucleotides with at least one 2'-O-methyl nucleotide, labeled "MNA") and the type of ligase (i.e., RNA ligase versus ssDNA ligase). These ligation experiments included the following tags: an all-DNA donor having the sequence of 5'-P-GCT GTG CAG GTA GAG TGC-6-FAM-3' (SEQ ID NO: 6); a 5'-MNA-DNA donor having the sequence of 5'-P-mGCT GTG CAG GTA GAG TGC-6-FAM-3' (SEQ ID NO: 7); an all-MNA donor having the sequence of 5'-P-mGmUmG mCmAmG mGmUmA mGmAmG mUmGmC-6-FAM-3' (SEQ ID NO: 8); a DNA-3'MNA acceptor having the sequence of 5'-HO-TAC GTA TAC GAC TGmG-OH-3' (SEQ ID NO: 9); an all-DNA acceptor having the sequence of 5'-HO-GCA GAC TAC GTA TAC GAC TGG-OH-3' (SEQ ID NO: 10); and an all-MNA acceptor having the sequence of 5'-HO-mUmAmC mGmUmA mUmAmC mGmAmC mUmGmG-OH-3' (SEQ ID NO: 11), where "m" indicates a 2'-OMe base, "P" indicates a phosphorylated nucleotide, and "FAM" indicates fluorescein.

Ligation efficiencies were calculated from gel densitometry data as the ratio between the intensity from the ligation product and the sum of the intensity from the ligation product and the unligated starting material. The reaction conditions for T4 RNA ligase included the following: 5 µM each of donor and acceptor oligonucleotides (15-18 nucleotides (nts) long) in a buffer solution containing 50 mM Tris HCl, 10 mM MgCl$_2$, 1 mM hexamine cobalt chloride, 1 mM ATP, 25% PEG4600, and 5 units of T4 RNA ligase (NEB—new units) at pH 7.5. The reactions were incubated at 37° C. for 16 hours. The reaction conditions for CircLigase™ included the following: 5 µM each of donor and acceptor oligonucleotides (length 15 or 18 nts) incubated in a buffer containing 50 mM MOPS (pH 7.5), 10 mM KCl, 5 mM MgCl$_2$, 1 mM DTT, 0.05 mM ATP, 2.5 mM MnCl$_2$, and 25% (w/v) PEG 8000 with 20 units of CircLigase™ (Epicentre) at 50° C. for 16 hours. The reactions were resolved on 8M urea/15% PAAG, followed by densitometry using excitation at 450 nm.

TABLE 2

| Donor | Acceptor | T4 RNA ligase | CircLigase ™ |
|---|---|---|---|
| All-DNA | All-DNA | 9% | 89% |
| All-DNA | All-MNA | 14% | 68% |
| All-DNA | DNA-3'MNA | 46% | 85% |
| All-MNA | All-DNA | 11% | 84% |
| All-MNA | All-MNA | 20% | 29% |
| All-MNA | DNA-3'MNA | 32% | 73% |
| 5'-MNA-DNA | All-DNA | 29% | 90% |
| 5'-MNA-DNA | All-MNA | 16% | 46% |
| 5'-MNA-DNA | DNA-3'MNA | 69% | 81% |

Generally, CircLigase ™ produced higher ligation yields than T4 RNA ligase (Table 2). When both donor and acceptor were DNA/MNA hybrid oligonucleotides, efficient ligation was achieved with T4 RNA ligase.

Figure 5C:
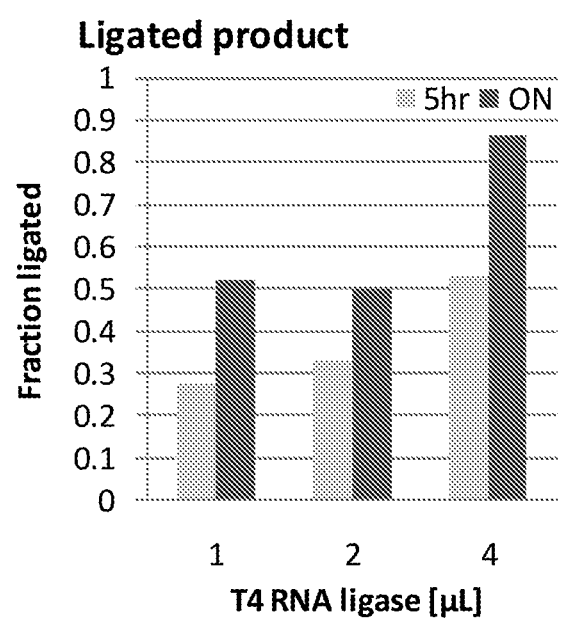

FIG. 5C shows high yield ligation achieved for T4 RNA ligase at high enzyme and oligonucleotide concentrations. The reaction conditions included following: 250 µM each of donor and acceptor oligonucleotides in a buffer containing 50 mM Tris HCl, 10 mM $MgCl_2$, 1 mM hexamine cobalt chloride, 2.5 mM ATP, 30% (w/v) PEG4600, pH 7.5, different amounts of T4 RNA ligase at 40 units/µL (NEB—new units), and 0.1 unit of yeast inorganic pyrophosphatase. The reactions were incubated at 37° C. for 5 and 20 hours and resolved on 8M urea/15% PAAG, followed by densitometry using excitation at 450 nm.

Overall, these data suggest that enzymatic ligation can be optimized by including one or more modified 2'-nucleotides and/or by using an RNA or DNA ligase. Further details for several other tested conditions, such as PEG or tag length, that can contribute to ligation efficiency are discussed below.

Example 2

Effect of PEG on Single-Stranded Ligation

Figure 6A:
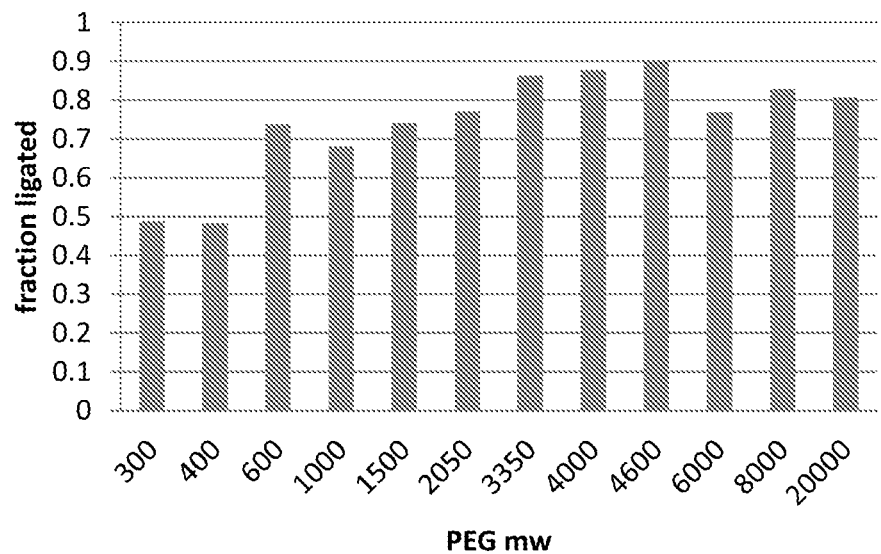
FIGS. 6A-6B represent optimization of PEG molecular weight (FIG. 6A) and concentration (FIG. 6B) to achieve maximal ligation yield by T4 RNA ligase. Reaction conditions are as described above for FIGS. 5A-5C.

To determine the effect of PEG molecular weight (MW) on ligation, single-stranded tags were ligated with 25% (w/v) of PEG having a MW from 300 to 20,000 Daltons. As shown in FIG. 6A, 80% or greater ligation was observed for PEG having a MW of 3,350, 4,000, 6,000, 8,000, and 20,000. These ligation experiments included the following tags: a 15mer donor having the sequence of 5'-P-mGTG CAG GTA GAG TGC-6-FAM-3' (SEQ ID NO: 12) and a 15mer acceptor having the sequence of 5'-HO-mUAC GTA TAC GAC TGmG-OH-3' (SEQ ID NO: 13). These oligonucleotide tags were DNA sequences with one or two terminal 2'O-methyl (2'-OMe) RNA bases (e.g., 2'-OMe-U (mU) or 2'-OMe-G (mG)).

Figure 6B:
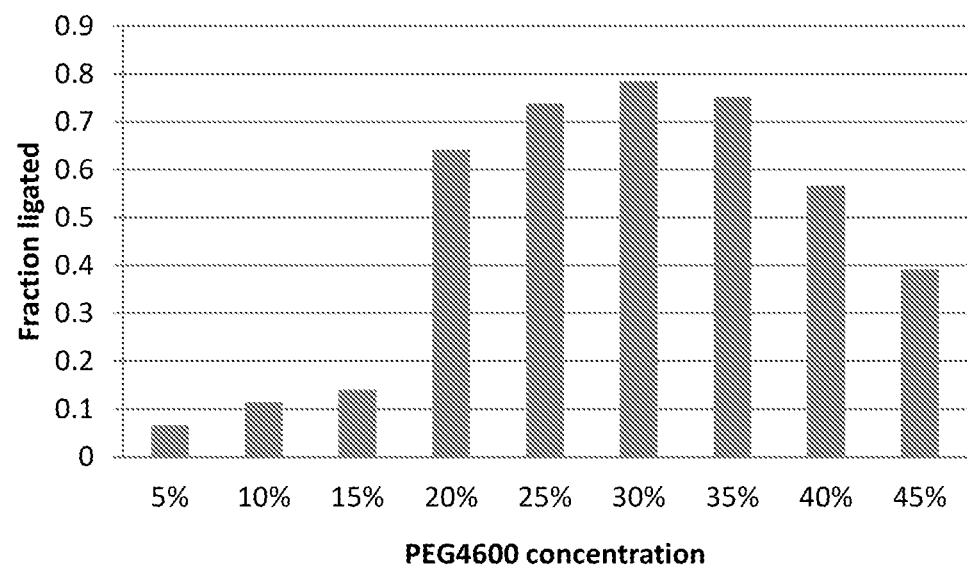

Experiments were also conducted to determine the effect of PEG concentration. Single-stranded tags were ligated with various concentration of PEG having a MW of 4,600 Daltons (PEG4600). As shown in FIG. 6B, 70% or greater ligation, on average, was observed for 25% (w/v) to 35% (w/v) PEG4600.

Example 3

Effect of Tag Length on Single-Stranded Ligation

To determine the effect of tag length on ligation, acceptor and donor tags of various lengths were constructed. For CircLigase™ experiments, a 15mer donor having the sequence 5'-P-mGTG CAG GTA GAG TGC-6-FAM-3' (SEQ ID NO: 12) was used and paired with 10, 12, 14, 16, and 18mer DNA acceptor oligonucleotides. For T4 RNA ligase experiments, the tags included one or more 2'-OMe-bases (designated as being MNA/DNA tags). Table 3 provides the sequence for the three donor tags (15mer, 8mer, and 5mer) and the three acceptor tags (15mer, 8mer, and 5mer).

TABLE 3

| Oligonucleotide tag | Sequence* |
|---|---|
| 15mer donor | 5'-P-mGTG CAG GTA GAG TGC-6-FAM-3' (SEQ ID NO: 12) |
| 15mer acceptor | 5'-HO-mUAC GTA TAC GAC TGmG-OH-3' (SEQ ID NO: 13) |
| 8mer donor | 5'-P-mGT GAG TGC-6-FAM-3' (SEQ ID NO: 14) |
| 8mer acceptor | 5'-HO-C A GAC TGmG-OH-3' (SEQ ID NO: 15) |
| 5mer donor | 5'-P-mGT GAC-6-FAM-3' (SEQ ID NO: 16) |
| 5mer acceptor | 5'-HO-mAC TGmG-OH-3' (SEQ ID NO: 17) |

*"m" indicates a 2'-OMe base, "P" indicates a phosphorylated nucleotide, and "FAM" indicates fluorescein.

Figure 7A:
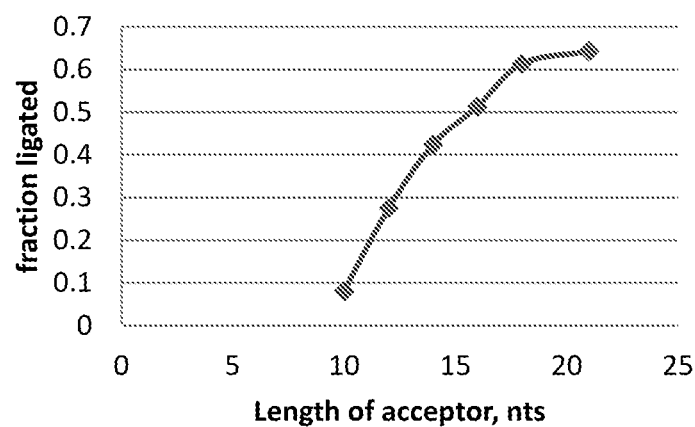
FIGS. 7A-7B show a correlation between ligation efficiency by CircLigase™ (FIG. 7A) and T4 RNA ligase (FIG. 7B) and length of the donor or acceptor oligonucleotides.
Figure 7B:
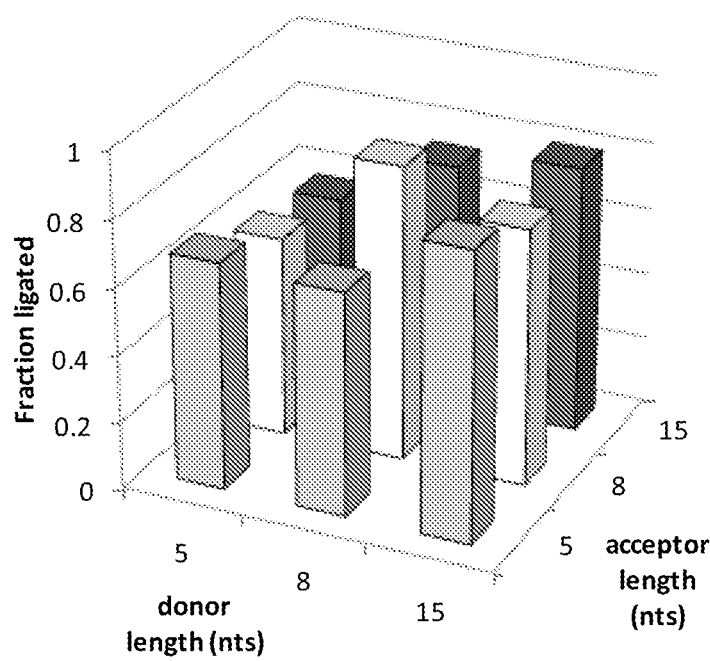

The extent of ligation was analyzed by densitometry of electrophoretic gels (FIGS. 7A-7B). The results of the CircLigase™ reactions indicate a strong dependence of ligation yield on the length of the acceptor oligonucleotide (FIG. 7A). The highest ligation yield was observed with an 18mer acceptor (62%), while ligation yield with a 10mer acceptor was lower than 10%. The results of the T4 RNA ligase reactions indicate that the combination of an 8mer acceptor with an 8mer donor provided the highest yield and that combinations having a 15mer donor with any of the tested acceptors provided yields greater than 75% (FIG. 7B). If a library includes shorter tags (i.e., about 10mer or shorter), then T4 RNA ligase may be preferred for tag ligation. In other cases, ligation can be further optimized by using CircLigase™ or a combination of T4 RNA ligase and CircLigase™.

Example 4

Effect of Purification on Single-Stranded Ligation

Figure 9:
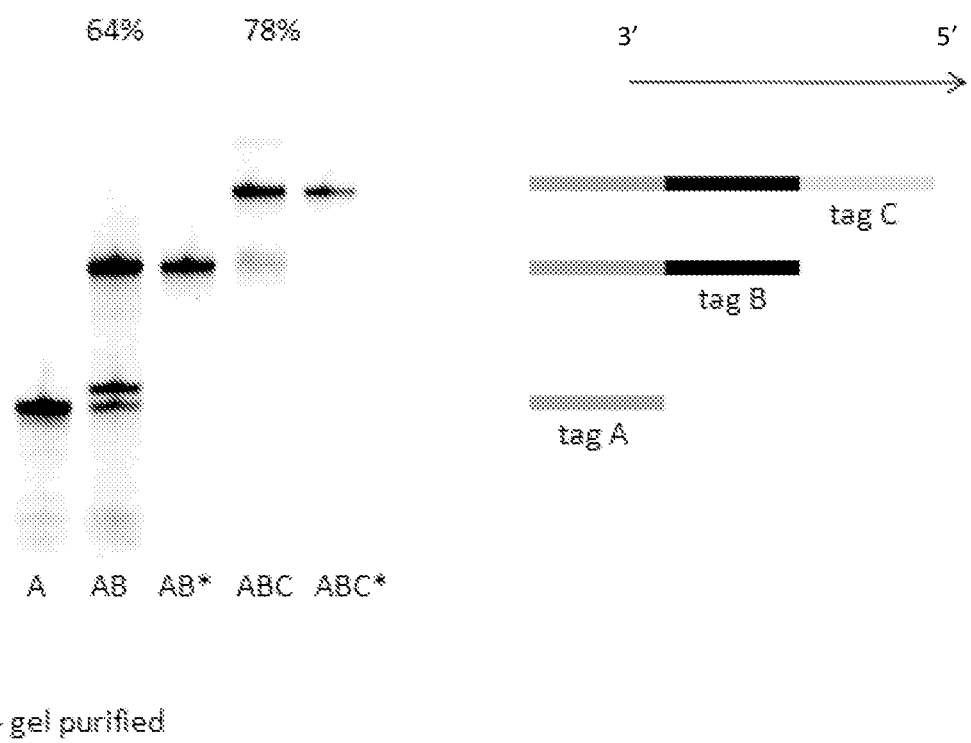
FIG. 9 shows an electrophoretic gel for sequential single-stranded ligation of tags A-C. The 3'-terminus included fluorescein to represent a library compound (or chemical entity), and the asterisk (*) indicates purification of the ligated product (or complex) prior to phosphorylation.

To determine the effect of purification on ligation, single-stranded tags were ligated to imitate the library synthetic process. For these experiments, the tags included 15mer donor and 15mer acceptor tags, as provided above in Table 3. The chemical entity was bound to the 3'-terminus of the library, where the chemical entity was fluorescein in this example to aid in visualization. As shown in FIG. 9 (right), successive tags were ligated to the 5'-OH group of the complex after phosphorylation by T4 PNK.

Figure 8A:
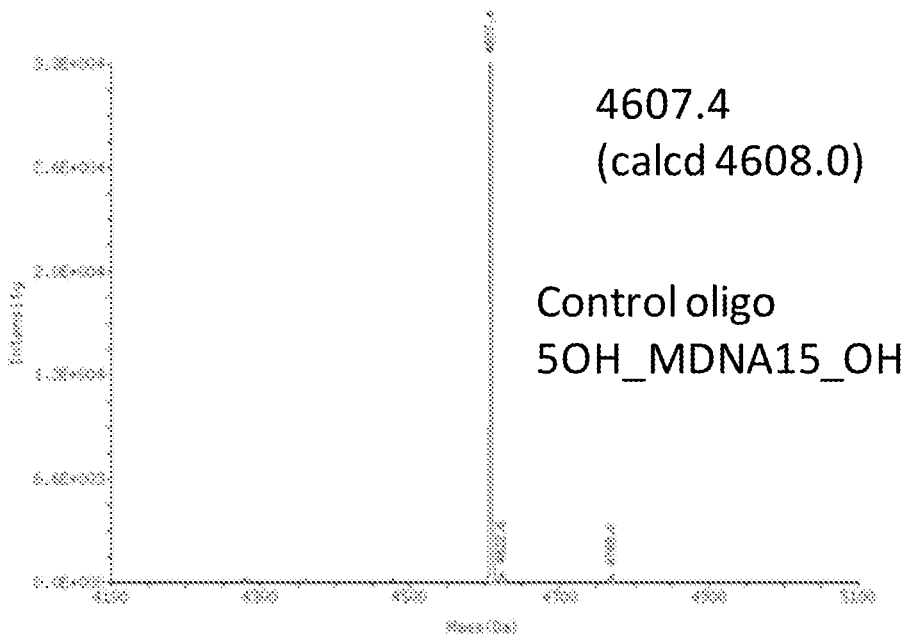
FIGS. 8A-8B are LC-MS spectra for a MNA/DNA tag before and after phosphorylation. Data are shown for 15mer tag 5'-HO-mUAC GTA TAC GAC TGmG-OH-3' (SEQ ID NO: 13) (at 250 µM) before (FIG. 8A) and after (FIG. 8B) reaction with T4 polynucleotide kinase (50 units per 5 nmole of tag).
Figure 8B:
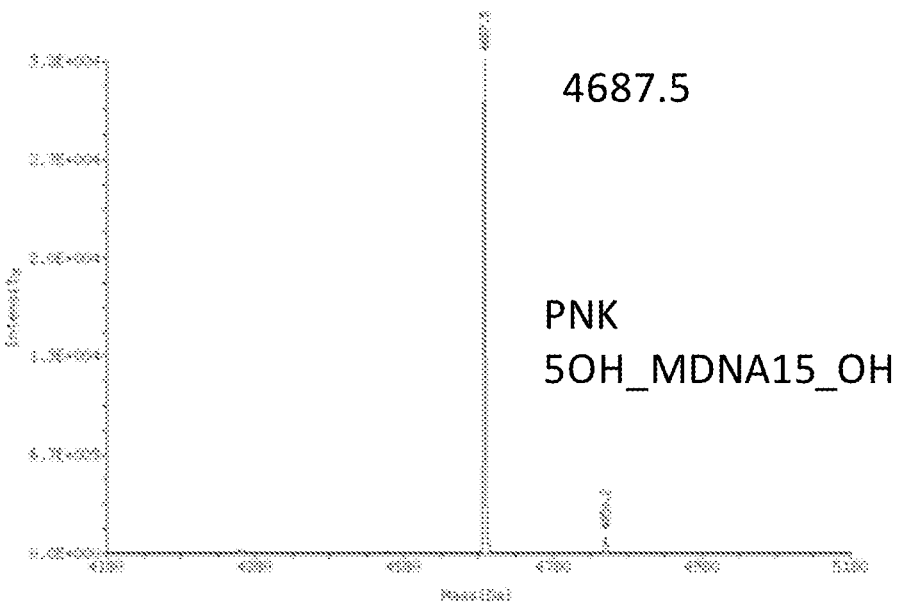

Experiments were also conducted by purifying the ligated product (i.e., the complex) prior to the PNK reaction, where particular agents useful in the ligation reaction (e.g., phosphate, cobalt, and/or unreacted tags) can inhibit the phosphorylation reaction with PNK or reduce ligation yield. As shown in FIG. 9 (left), purifying the complex (i.e., minimal precipitation) prior to the PNK reaction increased ligation (see data marked with *, indicating purification). FIGS. 8A-8B show LC-MS spectra for a 15mer MNA/DNA tag before and after phosphorylation. The presence or absence of DTT had no effect on phosphorylation.

Example 5

Chemically Co-Reactive Pair Ligation and Reverse Transcription of Junctions The methods described herein can further include chemically co-reactive pair ligation techniques, as well as enzyme ligation techniques. Accordingly, as an example of chemical ligation, an exemplary chemically co-reactive pair (i.e., an alkyne and an azido pair in a cycloaddition reaction) in two variants: a short chemically co-reactive pair and a long chemically co-reactive pair, was used.

Materials

Figure 10A:
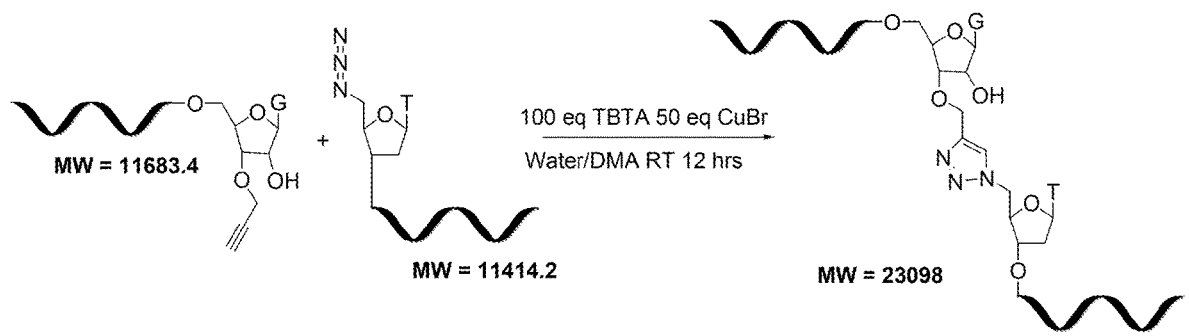
FIGS. 10A-10B show schematics of a "chemically co-reactive pair" reaction between donor and acceptor oligonucleotides resulting in a 5-atom "short" spacer (FIG. 10A) and a 24-atom "long" spacer (FIG. 10B).

In a first variant, a short chemically co-reactive pair (FIG. 10A) was used. The pair included (i) an oligonucleotide having the sequence 5'-GCG TGA ACA TGC ATC TCC CGT ATG CGT ACA GTC CAT T/propargylG/-3' ("5end3propargyl," SEQ ID NO: 18) and (ii) an oligonucleotide having the sequence 5'-/azidoT/ATA GCG CGA TAT ACA CAC TGG CGA GCT TGC GTA CTG-3' ("3end5azido," SEQ ID NO: 19). This pair of oligonucleotides was prepared by TriLink BioTechnologies, Inc. (San Diego, Calif.). These oligonucleotides were designed to produce a short spacer between two oligonucleotides upon ligation, where the linker would be 5 atoms long (counting from the C3'-position of the 5end3propargyl oligonucleotide to the C5'-position of the 3end5azido oligonucleotide). In addition, the 5'-azido oligonucleotide (3end5azido) was prepared by converting the iodo group in the corresponding 5'-iodo oligonucleotide into an azido group.

Figure 10B:
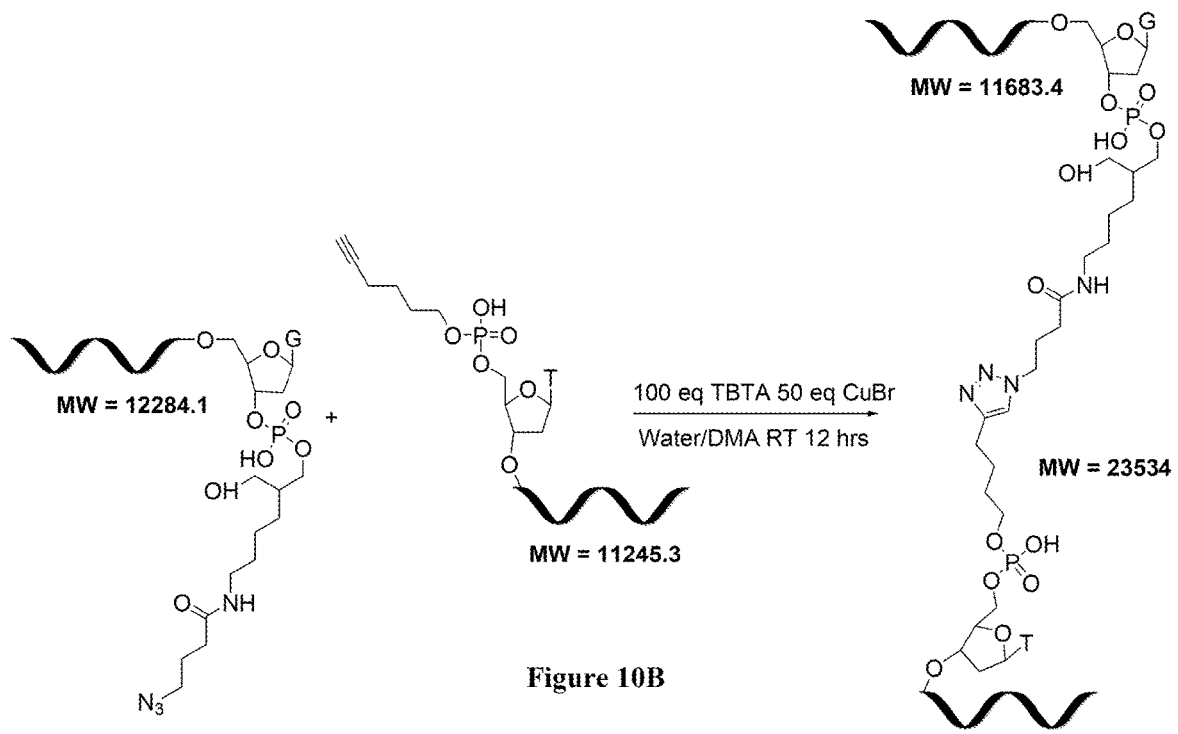

In a second variant, a long chemically co-reactive pair (FIG. 10B) was used. The pair included (i) an oligonucleotide having the sequence 5'-GCG TGA ACA TGC ATC TCC CGT ATG CGT ACA GTC CAT TG/spacer7-azide/-3' ("5end3azide," SEQ ID NO: 20) and (ii) an oligonucleotide having the sequence 5'-/hexynyl/TA GCG CGA TAT ACA CAC TGG CGA GCT TGC GTA CTG-3' ("3end5hexynyl," SEQ ID NO: 21). This pair of oligonucleotides was prepared by Integrated DNA Technologies, Inc. (IDT DNA, San Diego, Calif., and Coralville, Iowa). The 5end3azide oligonucleotide was prepared by reacting an azidobutyrate N-hydroxysuccinimide ester with a 3'-amino-modifier C7 (2-dimethoxytrityl oxymethyl-6-fluorenylmethoxycarbonylamino-hexane-1-succinoyl-long chain alkylamino), which was introduced during oligonucleotide column synthesis. This pair was designed to produce a 24 atom long spacer between the oligonucleotides (counting from the C3'-position of the 5end3azide oligonucleotide to the C5'-position of the 3end5hexynyl oligonucleotide).

Figure 11A:
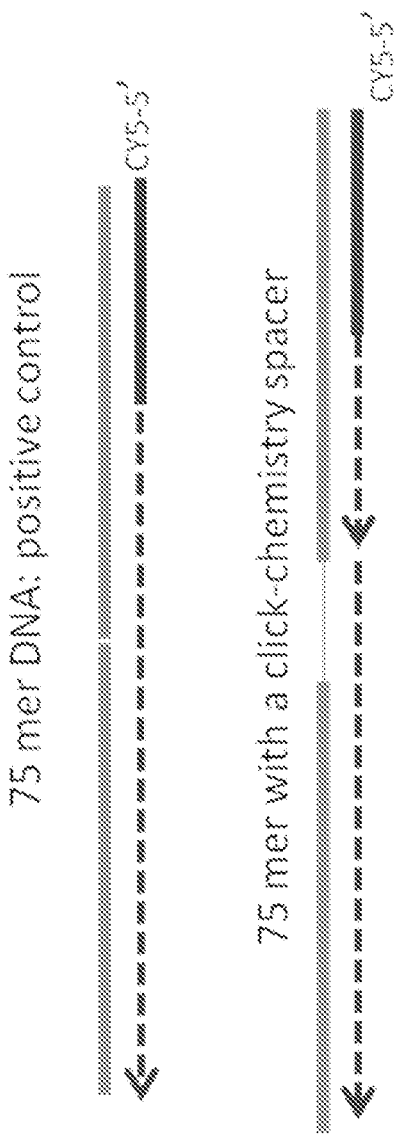
FIGS. 11A-11E show results of reverse transcription (RT) and PCR analysis of 75mer DNA templates containing a short or a long single spacer, as depicted in FIGS. 10A-10B.

For reverse transcription (as shown by the schematic in FIG. 11A), the primers and templates included the following: a reverse transcription primer having the sequence of 5'-/Cy5/CAG TAC GCA AGC TCG-3' ("Cy5s_primer15," SEQ ID NO: 22); a control template having the sequence of 5'-GCG TGA ACA TGC ATC TCC CGT ATG CGT ACA GTC CAT TGT ATA GCG CGA TAT ACA CAC TGG CGA GCT TGC GTA CTG-3' ("temp175," SEQ ID NO: 23); a 5'-PCR primer having the sequence of 5'-GCG TGA ACA TGC ATC TCC-3' (SEQ ID NO: 24); and a 3'-PCR primer having the sequence of 5'-CAG TAC GCA AGC TCG CC-3' (SEQ ID NO: 25), where these sequences were obtained from IDT DNA. A Cy5-labeled DNA primer was used for the experiments to enable separate detection of the reverse transcription products by LC.

Experimental Conditions

For the chemically co-reactive pair ligations, 1 mM solutions of chemically co-reactive pairs, such as 5end3propargyl+3end5azido (short) or 5end3azide+3end5hexynyl (long), were incubated for 12 hours in the presence of 100 equivalents of TBTA ligand (tris-[(1-benzyl-1H-1,2,3-triazol-4-yl)methyl]amine) and 50 equivalents of CuBr in a water/dimethyl acetate mixture. Following the reaction, an excess of EDTA was added, and the reaction mixtures were desalted using Zeba Spin Desalting Columns (Invitrogen Corp., Carlsbad, Calif.) and then ethanol precipitated. For the reverse transcription reactions, the templates were purified on a 15% polyacrylamide gel containing 8M urea.

Liquid chromatography-mass spectrometry (LC-MS) was performed on a Thermo Scientific LCQ Fleet using an ACE 3 C18-300 (50×2.1 mm) column and a 5 minute gradient of 5-35% of buffer B using buffer A (1% hexafluoroisopropanol (HFIP), 0.1% di-isopropylethyl amine (DIEA), 10 µM EDTA in water) and buffer B (0.075% HFIP, 0.0375% DIEA, 10 µM EDTA, 65% acetonitrile/35% water). LC was monitored at 260 nm and 650 nm. MS was detected in the negative mode, and mass peak deconvolution was performed using ProMass software.

Reverse transcription reactions were performed using ThermoScript™ RT (Invitrogen Corp.), according to the manufacturer's protocol, at 50° C. for 1-2 hours. The results were analyzed by LC-MS and by PCR. PCR was performed using Platinum® SuperMix and resolved on 4% agarose E-Gels (both from Invitrogen Corp.). Eleven and eighteen cycles of PCR were performed with or without a preceding RT reaction. The 75mer template was not reverse transcribed and used directly for the PCR amplification.

Results and Discussion

In both the ligations forming a short spacer and a long spacer, reaction yields were high, close to quantitative, as analyzed by LC-MS. Accordingly, chemical ligation provides a high yield technique to bind or operatively associate a headpiece to one or more building block tags.

For a viable chemical ligation strategy to produce DNA-encoded libraries, the resultant complex should be capable of undergoing PCR or RT-PCR for further sequencing applications. While PCR and RT-PCR may not be an issue with enzymatically ligated tags, such as described above, unnatural chemical linkers may be difficult to process by RNA or DNA polymerases. The data provided in FIGS. 11B-11E suggest that oligonucleotides having a spacer of particular lengths can be transcribed and/or reverse transcribed.

Figure 11B:
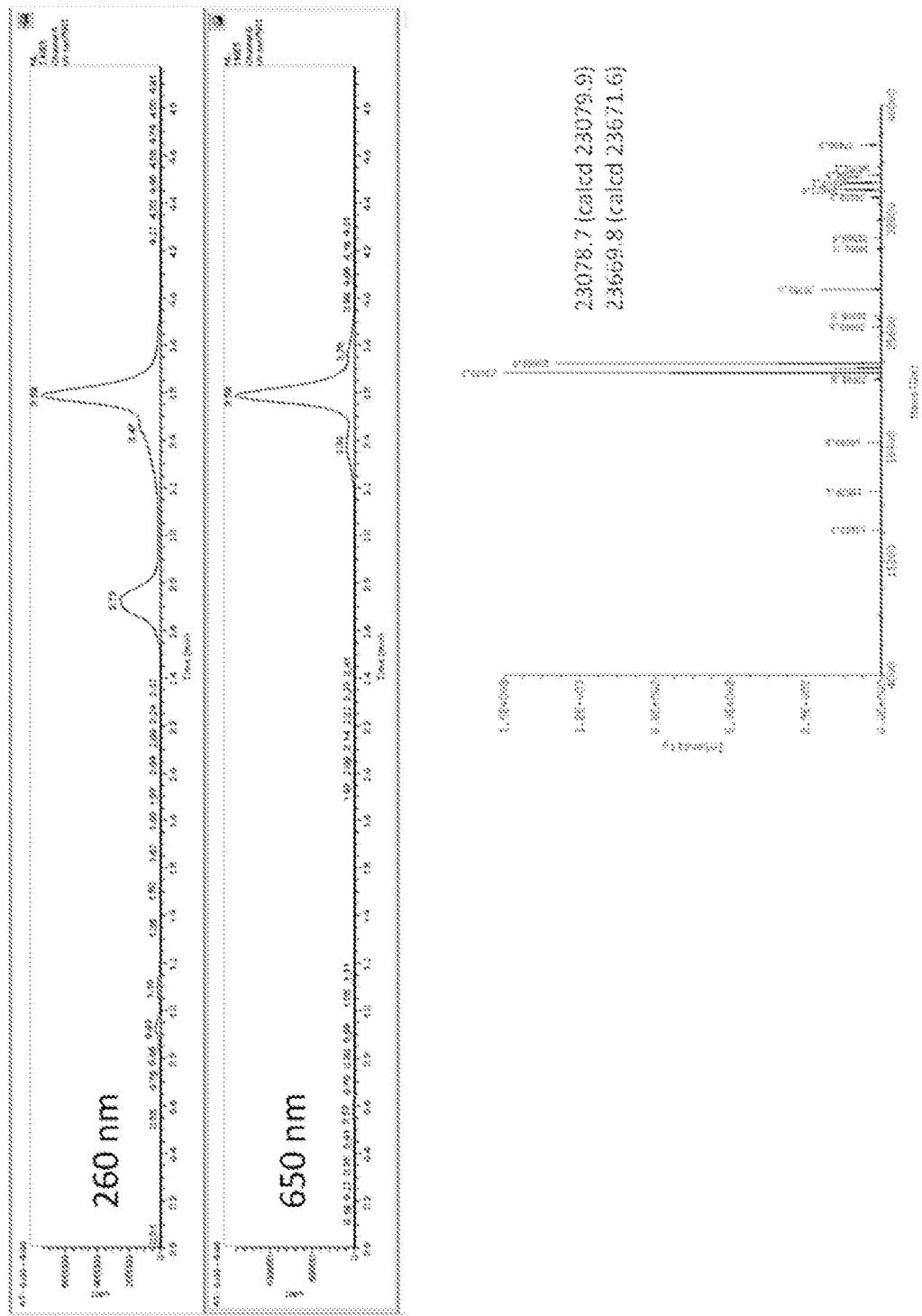
Figure 11C:
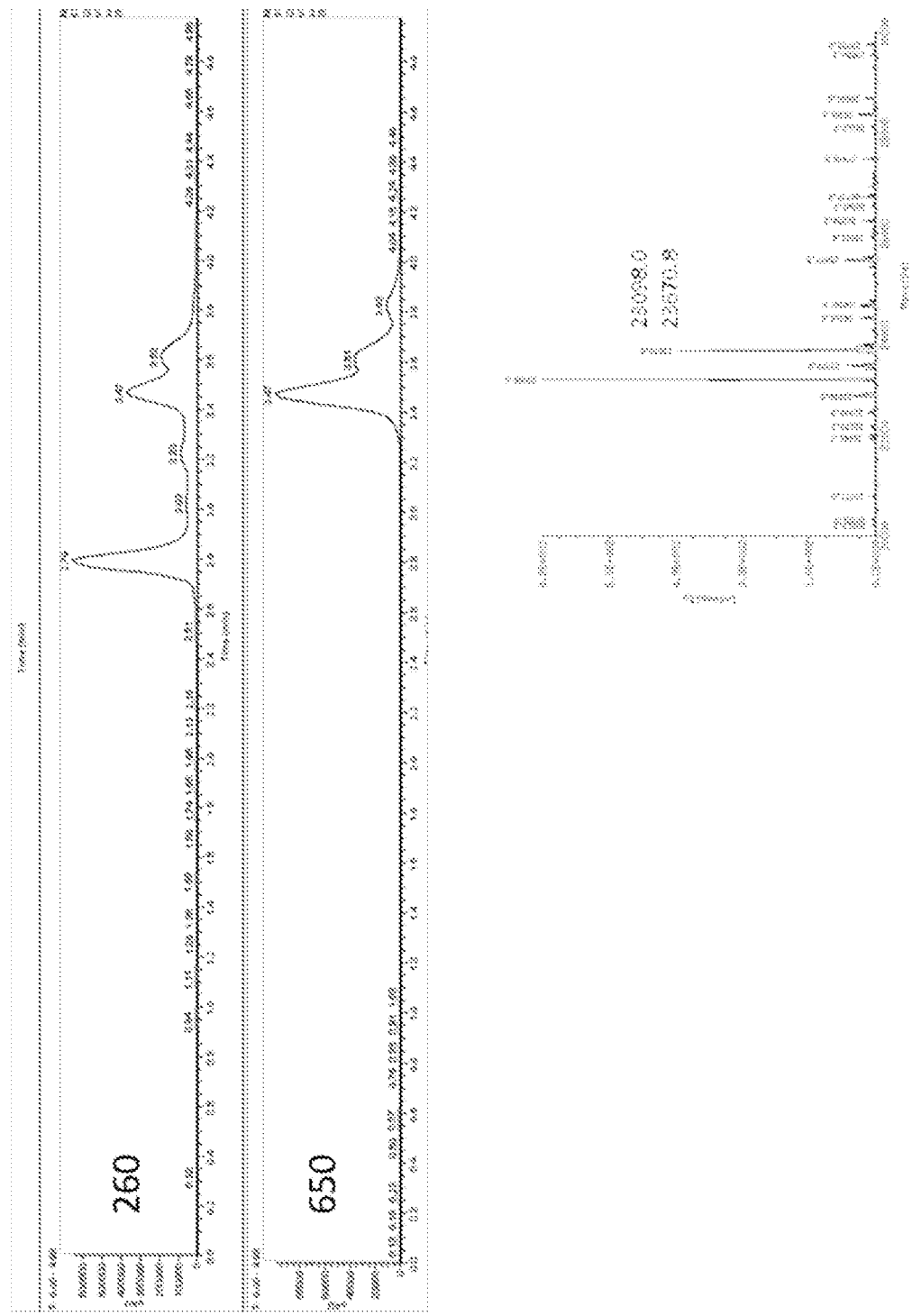

In the case of a chemically co-reactive pair linker resulting in a triazole-linked oligonucleotide, a dependence on the length of the linker was observed. For the short chemically co-reactive pair, the resultant template was reverse transcribed and analyzed by LC-MS. LC analysis revealed three major absorption peaks at 2.79 min., 3.47 min, and 3.62 min. for 260 nm, where the peaks at 3.47 min and 3.62 min. also provided absorption peaks at 650 nm. MS analysis of the peak at 3.47 min showed only the presence of the template 23097.3 (calc'd 23098.8), and the peak at 3.62 min. contained a template (23098.0) and a fully extended primer (23670.8, calc'd: 23671.6) at an approximately 1.7:1 ratio, suggesting a 50-60% yield for this RT reaction (FIG. 11C). For comparison, reverse transcription (RT) of the control having an all-DNA template produced the extended primer (peak 23068.9) in an amount roughly equivalent to the template (23078.7), suggesting close to a 100% yield (FIG. 11B).

Figure 11D:
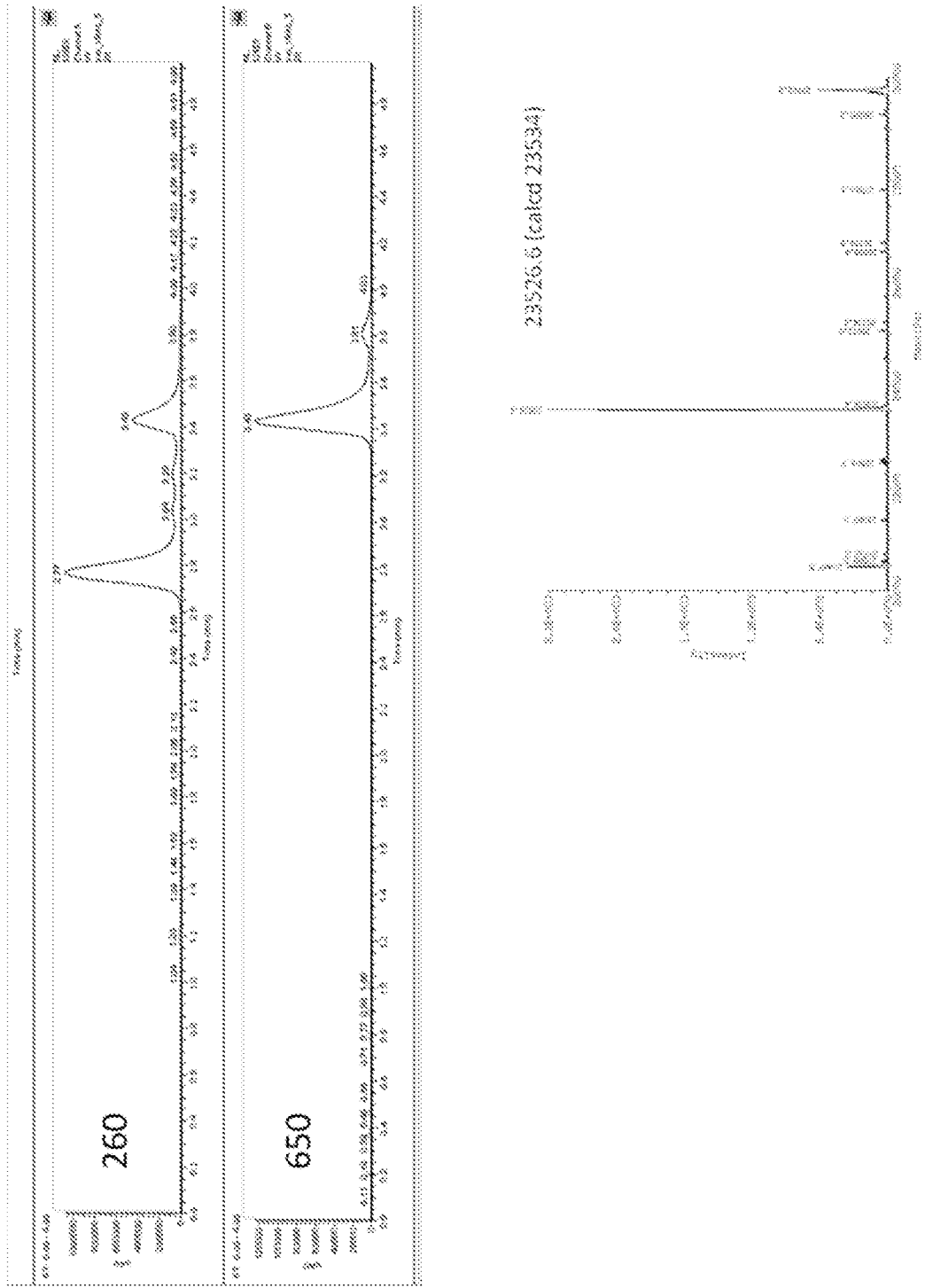

For the long chemically co-reactive pair, LC of the RT reaction showed two absorption peaks at 2.77 min and 3.43 min for 260 nm, where the peak at 3.43 min also provided absorption peaks at 650 nm, i.e., contained a Cy5 labeled material, which is the expected RT product. MS analysis of the peak at 3.43 min. revealed the template (observed 23526.6, calc'd: 23534.1), as well as the Cy5 primer extended to the linker (11569.1). No full length product was observed by LC-MS, indicating that the RT reaction did not occur in a measurable amount (FIG. 11D).

Figure 11E:
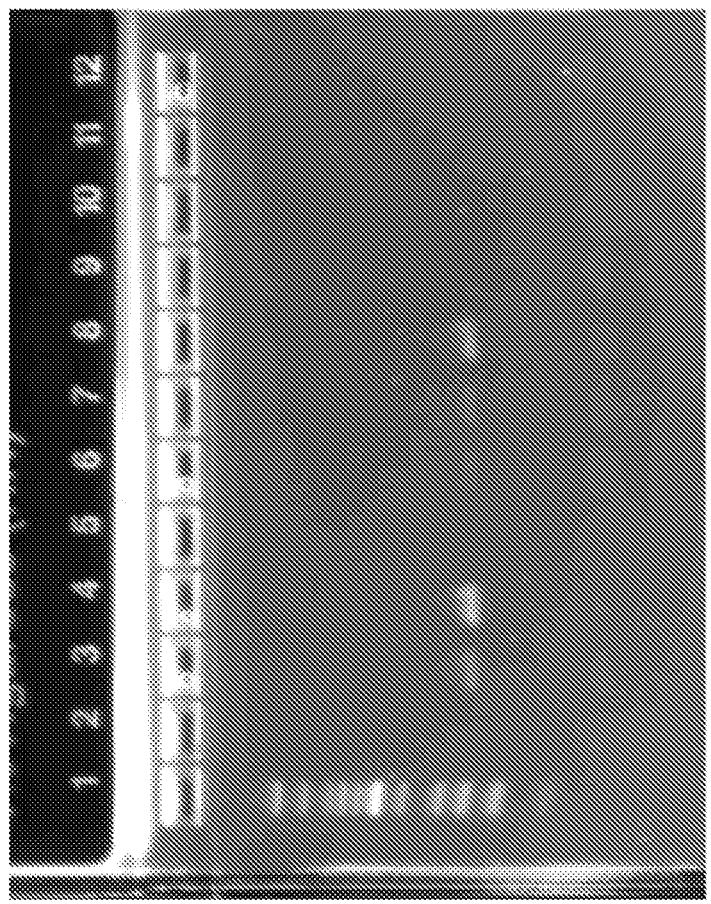

RT-PCR was performed with the templates described above and revealed that only the short linker yielded reverse transcription product, albeit at 5-10 lower efficiency (FIG. 11E). Efficiency of the RT was estimated to be about 2-fold lower than the template (temp175). For example, the PCR product of the short ligated template around 2-fold lower after RT and around 5-10 times lower without RT, as compared to the PCR product of the all-DNA template 75 (temp175). Accordingly, these data provide support for the use of chemical ligation to produce a complex that can be reverse transcribed and/or transcribed, and chemically ligated headpieces and/or tags can be used in any of the binding steps described herein to produce encoded libraries.

Example 6

Ligation of 3'-phosphorothioate Oligonucleotides with 5'-iodo Oligonucleotides

To determine the flexibility of the methods described herein, the ligation efficiency of oligonucleotides having other modifications were determined. In particular, analogs of the natural phosphodiester linkage (e.g., a phosphorothioate analog) could provide an alternative moiety for post-selection PCR analysis and sequencing.

The following oligonucleotides were synthesized by Tri-Link BioTechnologies, Inc. (San Diego, Calif.): (i) 5'-/Cy5/ CGA TAT ACA CAC TGG CGA GCT/thiophosphate/-3' ("CCy5," SEQ ID NO: 26), (ii) 5'-/IododT/GC GTA CTG AGC/6-FAM/-3' ("CFL," SEQ ID NO: 27), as shown in FIG. 12A, and (iii) a splint oligonucleotide having the sequence of CAG TAC GCA AGC TCG CC ("sp1," SEQ ID NO: 28). Ligation reactions were performed with 100 µM of each reactant oligonucleotide in a buffer containing 50 mM Tris HCl (pH 7.0), 100 mM NaCl, and 10 mM $MgCl_2$ ("ligation buffer") at room temperature. The ligation reactions were supplemented by either of the following: 100 µM of the splint oligonucleotide, 10 mM $Co(NH_3)_6Cl_3$, 40% (w/v) of PEG4000, or 80% (w/v) of PEG300. The reaction was allowed to progress for up to 48 hours. Ligation products were analyzed by LC-MS using detection at 260 nm, 495 nm, and 650 nm, as well as by an 8M urea/15% polyacrylamide gel (PAAG) that was further scanned at 450 and 635 nm excitation on a Storm™ 800 PhosphorImager.

In the absence of the splint oligonucleotide, no ligation was observed (FIG. 12B, lanes labeled "−sp1"). In the presence of the splint oligonucleotide, ligation occurred and reached around 60% of fraction ligated after 48 hours (FIGS. 12B-12C). LC-MS revealed several peaks in the chromatogram, with a peak at 3.00 min absorbing at 260 nm, 495 nm, and 650 nm. MS of this peak showed mostly the product of ligation at 11539.6 Da (calc'd 11540) with less than 10% of CCy5 oligonucleotide at 7329.8 Da (calc'd 7329.1). Low levels of ligation were detected in the presence of PEGs and hexamine cobalt, where hexamine cobalt caused precipitation of the Cy5-labeled oligonucleotide. These data suggest that headpieces and/or tags having modified phosphate groups (e.g., modified phosphodiester linkages, such as phosphorothioate linkages) can be used in any of the binding steps described herein to produce encoded libraries.

In order to further study the iodo-phosphorothioate ligation reaction, the ligation of 5'-I dT-oligo-3'-FAM (CFL) and 5'-Cy5-oligo-3'-PS (CCy5) was performed in the absence and presence of a splint under different reaction conditions.

Figure 12D:
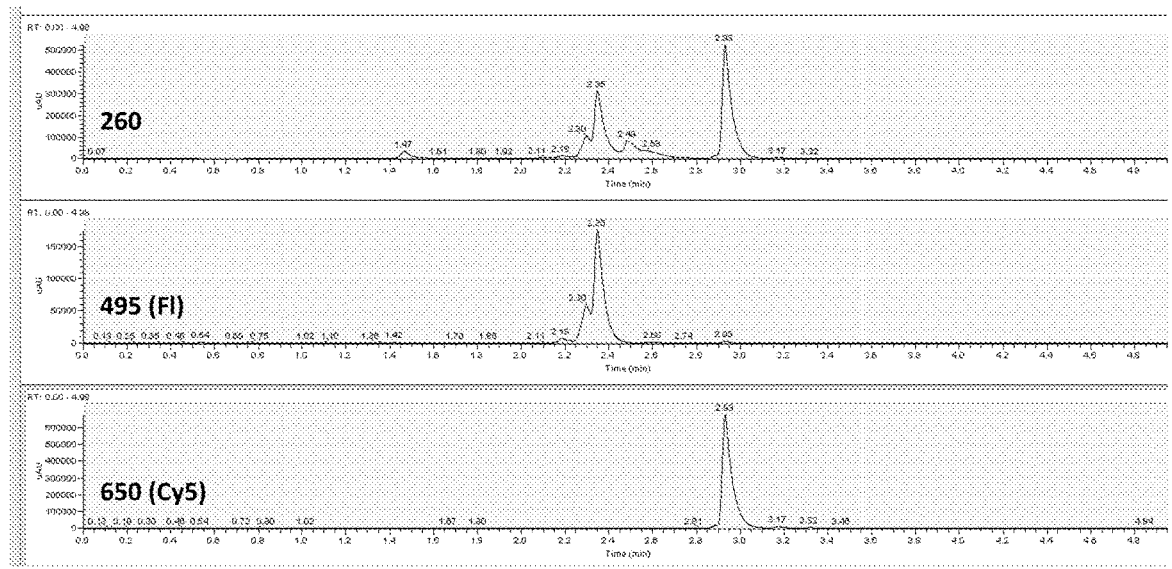
Figure 12D:
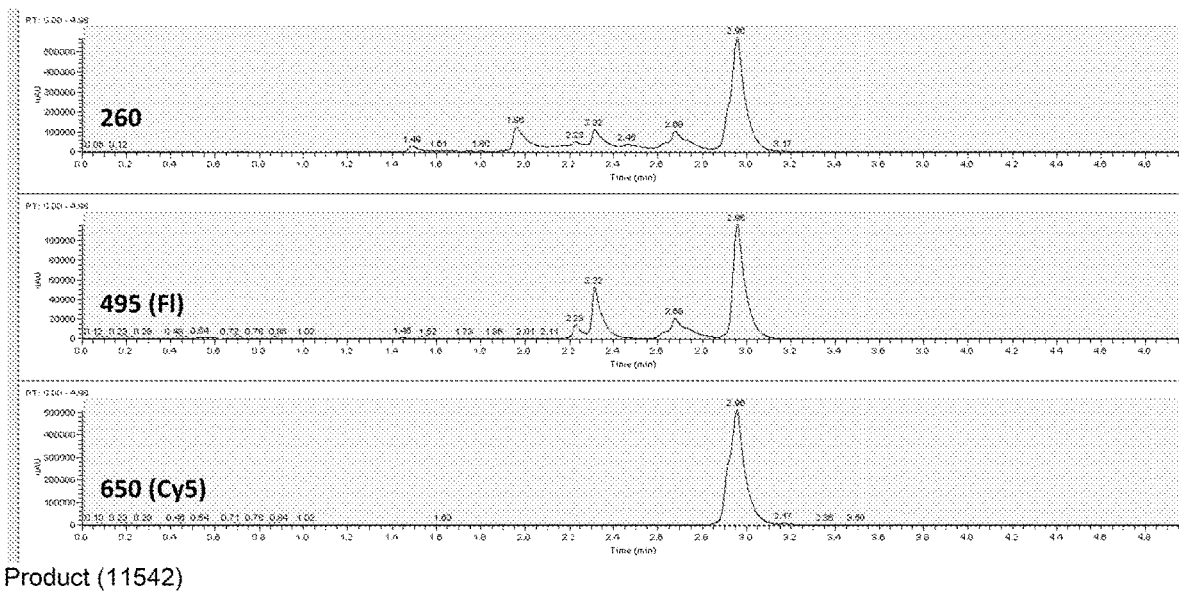

In a first set of conditions, ligation experiments were conducted with incubation for seven to eight days. These experiments were performed in the same ligation buffer as above with 50 µM of each oligonucleotide and incubated for a week at room temperature. FIG. 12D shows LC-MS analysis of the ligation of CFL and CCy5 in the absence (top) and presence (bottom) of a splint (positive control), where ligation reactions were incubated for seven days. Three LC traces were recorded for each reaction at 260 nm (to detect all nucleic acids), at 495 nm (to detect the CFL oligonucleotide and the ligation product), and at 650 nm (to detect the CCy5 oligonucleotide and the ligation product).

In the absence of the splint, no ligation occurred, and only starting materials CFL (4339 Da) and CCy5 (7329 Da) were detected (FIG. 12D, top). When the splint oligonucleotide was present for seven days, a characteristic peak was observed in 495 nm channel with a retention time of 2.98 min, which corresponds to the ligated product (11542 Da) (FIG. 12D, bottom). This peak overlapped with that for the CCy5 oligonucleotide observed at the 650 nm channel and, thus, was indistinguishable from CCy5 at 650 nm.

Figure 12E:
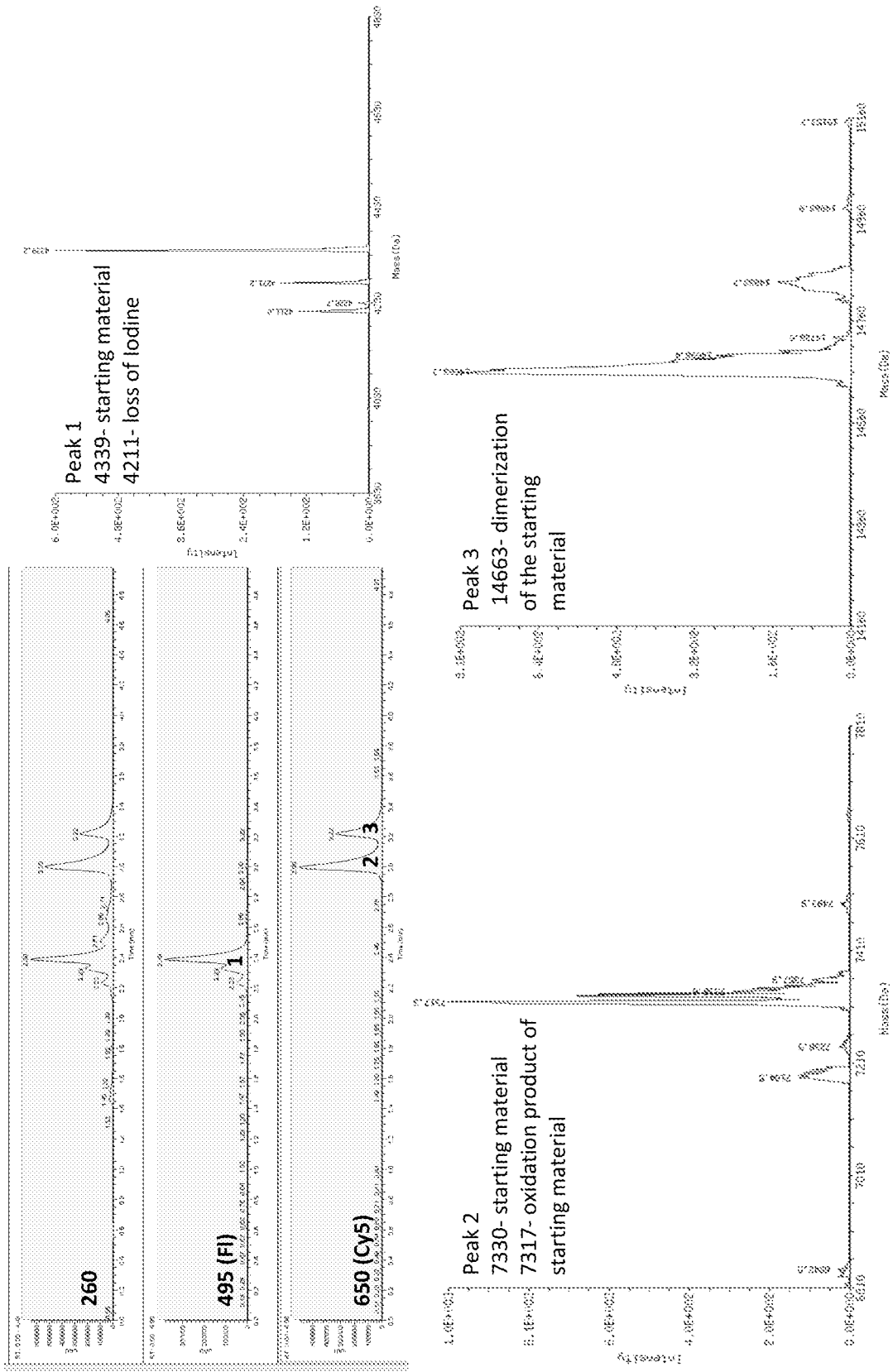

FIG. 12E shows the LC-MS analysis of CFL and CCy5 in the absence of a splint, where ligation reactions were incubated for eight days at 400 µM of each oligonucleotide. No ligation product was detected. Peak 1 (at 495 nm) contained CFL starting material (4339 Da), as well as traces of the loss of iodine product (4211 Da) and an unknown degradation product (4271 Da, possibly ethyl mercaptane displacement). Peak 2 (at 650 nm) contained CCy5 starting material (7329 Da) and oxidized CCy5 oligonucleotide (7317 Da). Peak 3 (at 650 nm) contained dimerized CCy5 (14663 Da).

Figure 12F:
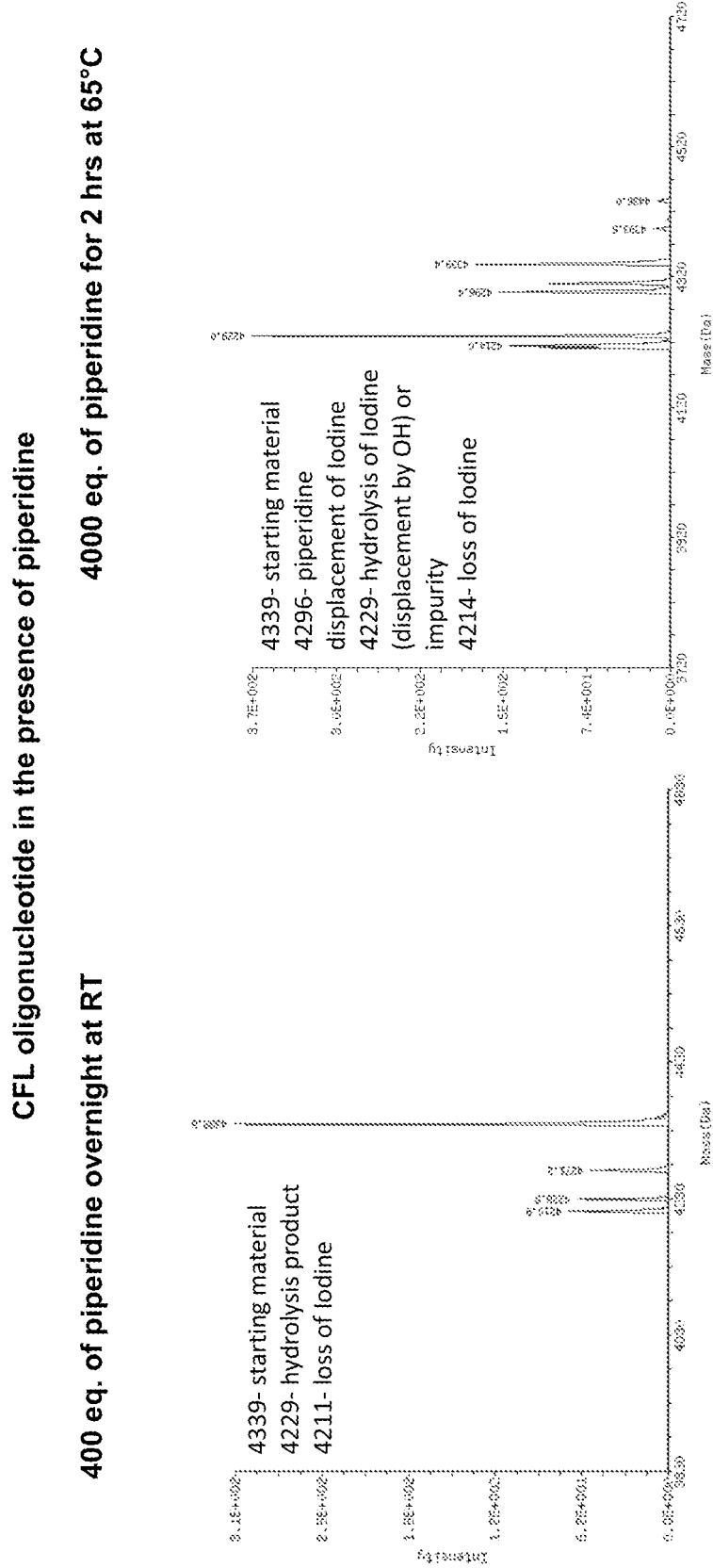

In a second set of conditions, iodine displacement reactions were conducted in the presence of piperdine and at a pH higher than 7.0. FIG. 12F shows MS analysis for a reaction of CFL oligonucleotide with piperidine, where this reaction was intended to displace the terminal iodine present in CFL. One reaction condition included oligonucleotides at 100 µM, piperidine at 40 mM (400 equivalents) in 100 mM borate buffer, pH 9.5, for 20 hrs at room temperature (data shown in left panel of FIG. 12F); and another reaction condition included oligonucleotides at 400 µM, piperidine at 2 M (4,000 equivalents) in 200 mM borate buffer, pH 9.5, for 2 hrs at 65° C. (data shown in right panel of FIG. 12F).

In the reaction condition including 40 mM of piperidine (FIG. 12F, left), no piperidine displacement was observed, and a small amount of hydrolysis product was detected (4229 Da). In addition, traces of the loss of iodine (4211 Da) and unknown degradation product (4271 Da) were observed. In the reaction condition including 2 M of piperidine (FIG. 12F, right), piperidine displacement of iodine was observed (4296 Da), and the amount of starting material was substantially diminished (4339 Da). In addition, peaks corresponding to hydrolysis of iodine (by displacement of OH) or impurity (4229 Da) and loss of iodine (4214 Da) were also observed. These data show that the presence of an amine (e.g., as part of chemical library synthesis) will not detrimentally effect the oligonucleotide portion of the library members and/or interfere with this ligation strategy.

Figure 12G:
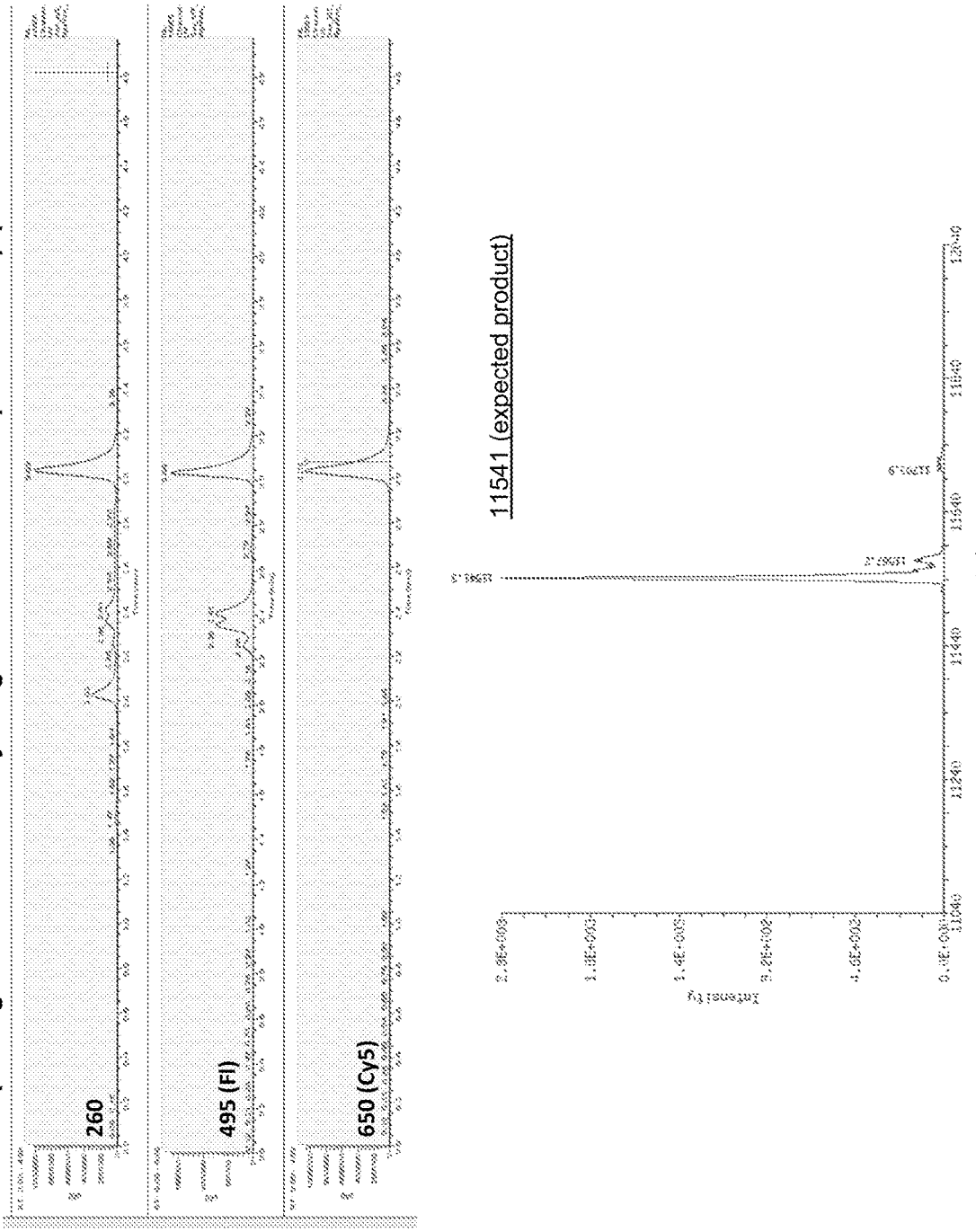

In a third set of conditions, splint ligation reactions were conducted in the presence of piperdine and at a pH higher than 7.0. FIG. 12G shows a splint ligation reaction of CFL and CCy5 oligonucleotides at 50 μM performed in the presence of 400 equivalents of piperidine in 100 mM borate buffer, pH 9.5, for 20 hrs at room temperature. The characteristic peak detected in the LC trace (at 495 nm) contained predominantly the product of ligation at 11541.3 Da (calc'd 11540 Da). Based on these results, it can be concluded that that piperidine does not impair enzymatic ligation and that the presence of other amines (e.g., as part of chemical library synthesis) will likely not interfere with this ligation strategy.

Taking together, these data indicate that this ligation strategy can be performed under various reaction conditions that are suitable for a broad range of chemical transformations, including extended incubation times, elevated pH conditions, and/or presence of one or more amines. Thus, the present methods can be useful for developing library members with diverse reaction conditions and precluding the necessity of buffer exchange, such as precipitation or other resource-intensive methods.

Example 7

Minimization of Shuffling with Modified Nucleotides

During single-stranded enzymatic ligation with T4 RNA ligase, low to moderate extent of terminal nucleotide shuffling can occur. Shuffling can result in the inclusion or excision of a nucleotide, where the final product or complex includes or excludes a nucleotide compared to the expected ligated sequence (i.e., a sequence having the complete sequence for both the acceptor and donor oligonucleotides).

Though low levels of shuffling can be tolerated, shuffling can be minimized by including a modified phosphate group. In particular, the modified phosphate group is a phosphorothioate linkage between the terminal nucleotide at the 3'-terminus of an acceptor oligonucleotide and the nucleotide adjacent to the terminal nucleotide. By using such a phosphorothioate linkage, shuffling was greatly reduced. Only residual shuffling was detected by mass spectrometry, where shuffling likely arose due to incomplete conversion of the native phosphodiester linkage into the phosphorothioate linkage or to low levels of oxidation of the phosphorothioate linkage followed by conversion into the native phosphodiester linkage. Taking together this data and the ligation data in Example 6, one or more modified phosphate groups (e.g., a phosphorothioate or a 5'-N-phosphoramidite linkage) could be included in any oligonucleotide sequence described herein (e.g., between the terminal nucleotide at the 3'-terminus of a headpiece, a complex, a building block tag, or any tag described herein, and the nucleotide adjacent to the terminal nucleotide) to minimize shuffling during single-stranded ligation.

A single stranded headpiece (ssHP, 3636 Da) was phosphorylated at the 5'-terminus and modified with a hexylamine linker at the 3'-terminus to provide the sequence of 5'-P-mCGAGTCACGTC/Aminohex/-3' (SEQ ID NO: 29). The headpiece was ligated to a tag (tag 15, XTAGSS000015, 2469 Da) having the sequence of 5'-mCAGTGTCmA-3' (SEQ ID NO: 30), where mC and mA indicate 2'-O methyl nucleotides. LC-MS analysis (FIG. 13A) revealed that the ligation product peak contained up to three species, which was partially separated by LC and had the following molecular weights: 6089 Da (expected), 5769 Da (−320 Da from expected) and 6409 Da (+320 Da from expected). This mass difference of 320 Da corresponds exactly to either removal or addition of an extra O-Me C nucleotide ("terminal nucleotide shuffling").

Experiments with other terminal O-Me nucleotides, as well as terminal 2'-fluoro nucleotides, confirmed that shuffling likely occurs by cleavage of the 5'-terminal nucleotide of the donor oligonucleotide, probably after adenylation of the latter. The mechanism of this event is unknown. Without being limited by mechanism, FIG. 13B illustrates a possible scheme for nucleotide reshuffling during T4 RNA ligase reaction between a headpiece and a tag, where one of skill in the art would understand that this reaction could occur between any donor and acceptor oligonucleotides (e.g., between two tags, where one tag is the donor oligonucleotide and the other tag is the acceptor oligonucleotide).

Generally, the majority of the ligation reaction with T4 RNA ligase (T4Rnl1) provides the expected (normal) ligation product having the combined sequence of both the donor and acceptor oligonucleotides (FIG. 13B-1, reaction on left). A small minority of the reaction provides aberrant ligation products (FIG. 13B-1, reaction on right), where these aberrant products include those having the removal or addition of a terminal nucleotide ("Product−1 nt" and "Product+1 nt," respectively, in FIG. 13B-2).

Without being limited by mechanism, cleavage of the donor oligonucleotide ("headpiece" or "HP" in FIG. 13B-1) may occur by reacting with the 3'-OH group of the acceptor ("tag"), thereby providing a 5'-phosphorylated donor lacking one nucleotide ("HP-1 nt") and an adenylated nucleotide with an accessible 3'-OH group ("1 nt"). FIG. 13B-2 shows two exemplary schemes for the reaction between the headpiece (HP), tag, HP-1 nt, and 1 nt. To provide a product with an excised terminal nucleotide (FIG. 13B-2, left), the 5'-phosphorylated donor lacking one nucleotide (HP-1 nt) acts a substrate for the ligation event. This HP-1 nt headpiece is re-adenylated by T4 RNA ligase (to provide "Adenylated HP-1 nt" in FIG. 13B-2) and ligated to the tag, resulting in a ligation product minus one nucleotide ("Product-1 nt"). To provide a product with an additional terminal nucleotide (FIG. 13B-2, left), the adenylated nucleotide (1 nt) likely serves as a substrate for ligation to the tag, thereby producing an oligonucleotide having one nucleotide longer than the acceptor ("Tag+1 nt"). This Tag+1 nt oligonucleotide likely serves as an acceptor for the unaltered headpiece, where this reaction provides a ligation product having an additional nucleotide ("Product+1 nt"). LC-MS analyses of "Product", "Product-1 nt", and "Product+1 nt" were performed (FIG. 13B-3). When an aberrant tag and an aberrant headpiece (i.e., Tag+1 nt and HP-1 nt, respectively) recombine, then the resultant ligation product is indistinguishable from the expected product.

Figure 13C:
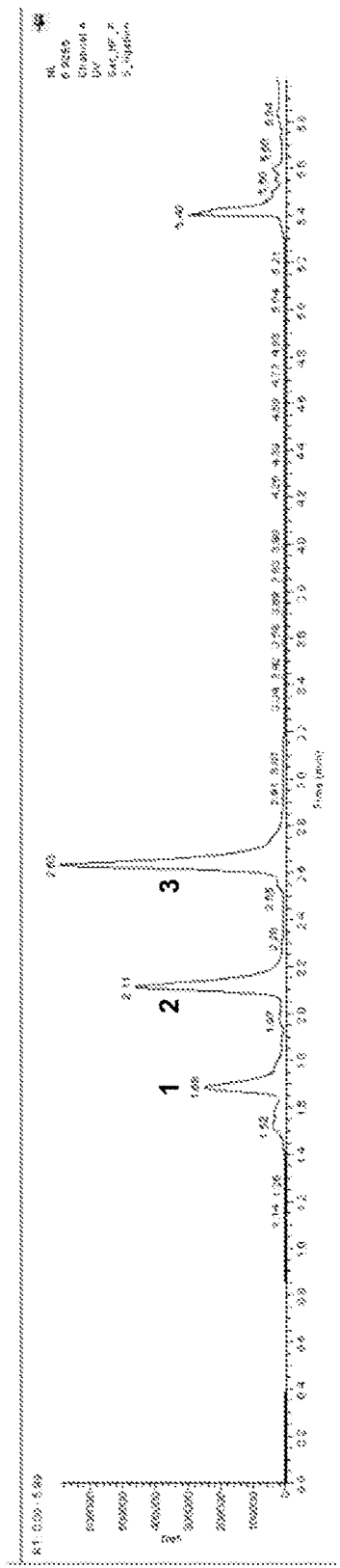
Figure 13C:
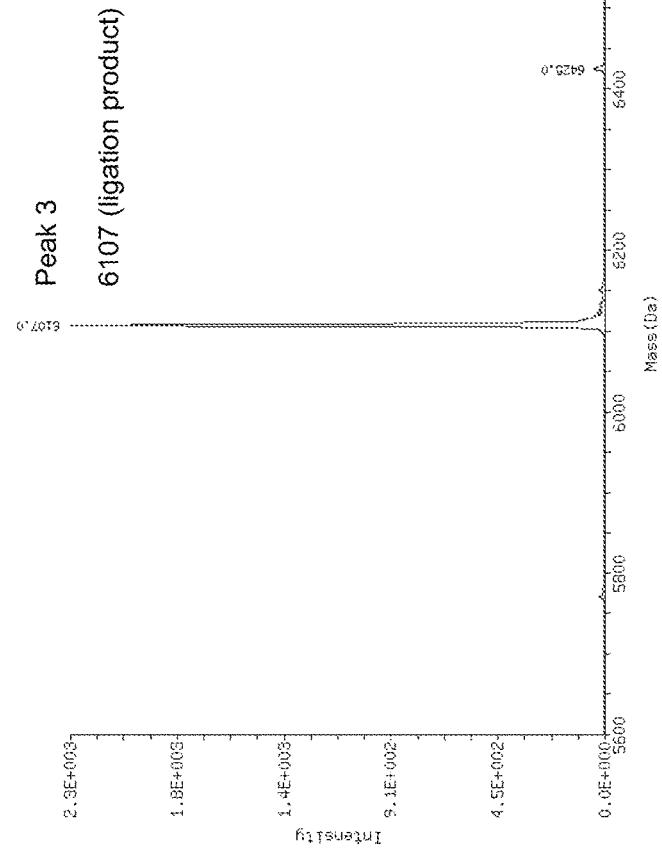

To further study the mechanism of terminal nucleotide reshuffling, a headpiece (HP-PS) having the sequence of 5'P-mC*GAGTCACGTC/Aminohex/-3' (SEQ ID NO: 31) was prepared. Headpiece HP-PS has the same sequence as ssHP but contains one modification, namely the first phosphodiester linkage between 5'-terminal nucleotide mC and the following G was synthesized as a phosphorothioate linkage (one non-bridging phosphate oxygen was substituted by a sulfur). LC-MS analysis of the HP-PS ligation to tag 15 revealed that shuffling was almost completely inhibited (FIG. 13C). Traces of +/−320 peaks likely correspond to the oxidative conversion of the phosphorothioate linkage into native phosphodiester linkages or incomplete sulfurization.

Example 8

Size Exclusion Chromatography of Library Members

Libraries of chemical entities that are generated using short, single-stranded oligonucleotides as encoding elements are well suited for the enrichment of binders via size exclusion chromatography (SEC). SEC is chromatographic technique that separates molecules on the basis of size, where larger molecules having higher molecular weight flow through the column faster than smaller molecules having lower molecular weight.

Figure 14:
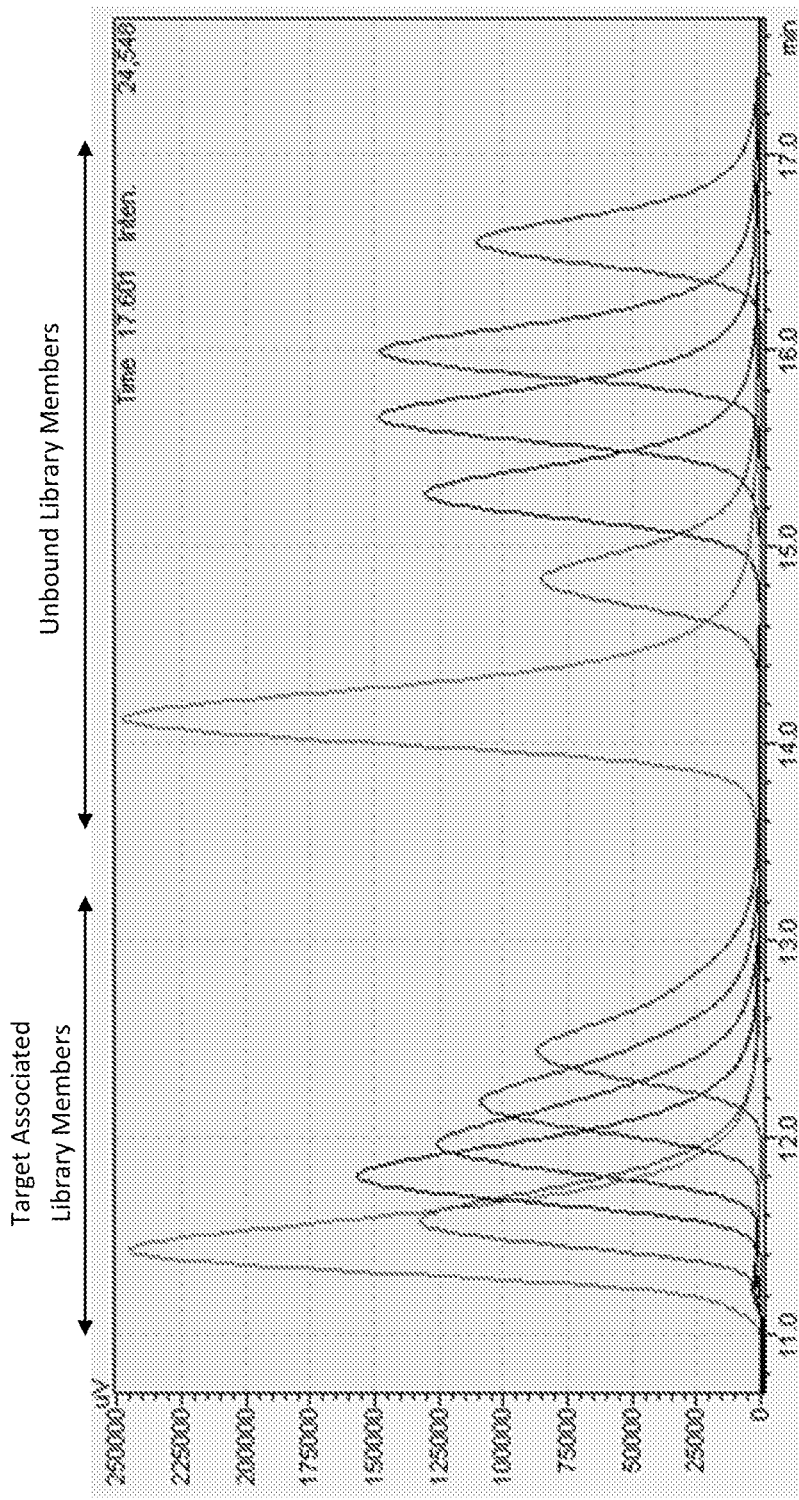
FIG. 14 is a graph showing separation of library members using size exclusion chromatography, where target-bound library members (left on graph) elute at a shorter time than unbound library members (right on graph).

Complexes of proteins and ssDNA library members can be readily separated from unbound library members using SEC. FIG. 14 is an ultraviolet trace from an SEC experiment in which a small molecule covalently attached to short ssDNA (a range of oligonucleotides with defined lengths in the 20-50 mer range) was mixed with a protein target known to bind the small molecule. The peaks that elute first from the column, in the 11-13 minute time range, represent target-associated library members. The later peaks, eluting from 14-17 minutes, represent unbound library members. The ratio of protein target to library molecule was 2:1, so approximately 50% of the library molecules should associate with the protein in the early eluting fraction, as observed in FIG. 14. Libraries with larger, double-stranded oligonucleotide coding regions cannot be selected using this method since the unbound library members co-migrate with the bound library members on SEC. Thus, small molecule libraries attached to encoding single-stranded oligonucleotides in the 20-50mer length range enable the use of a powerful separation technique that has the potential to significantly increase the signal-to-noise ratio required for the effective selection of small molecule binders to one or more targets, e.g., novel protein targets that are optionally untagged and/or wild-type protein. In particular, these approaches allow for identifying target-binding chemical entities in encoded combinatorially-generated libraries without the need for tagging or immobilizing the target (e.g., a protein target).

Example 9

Figure 15A:
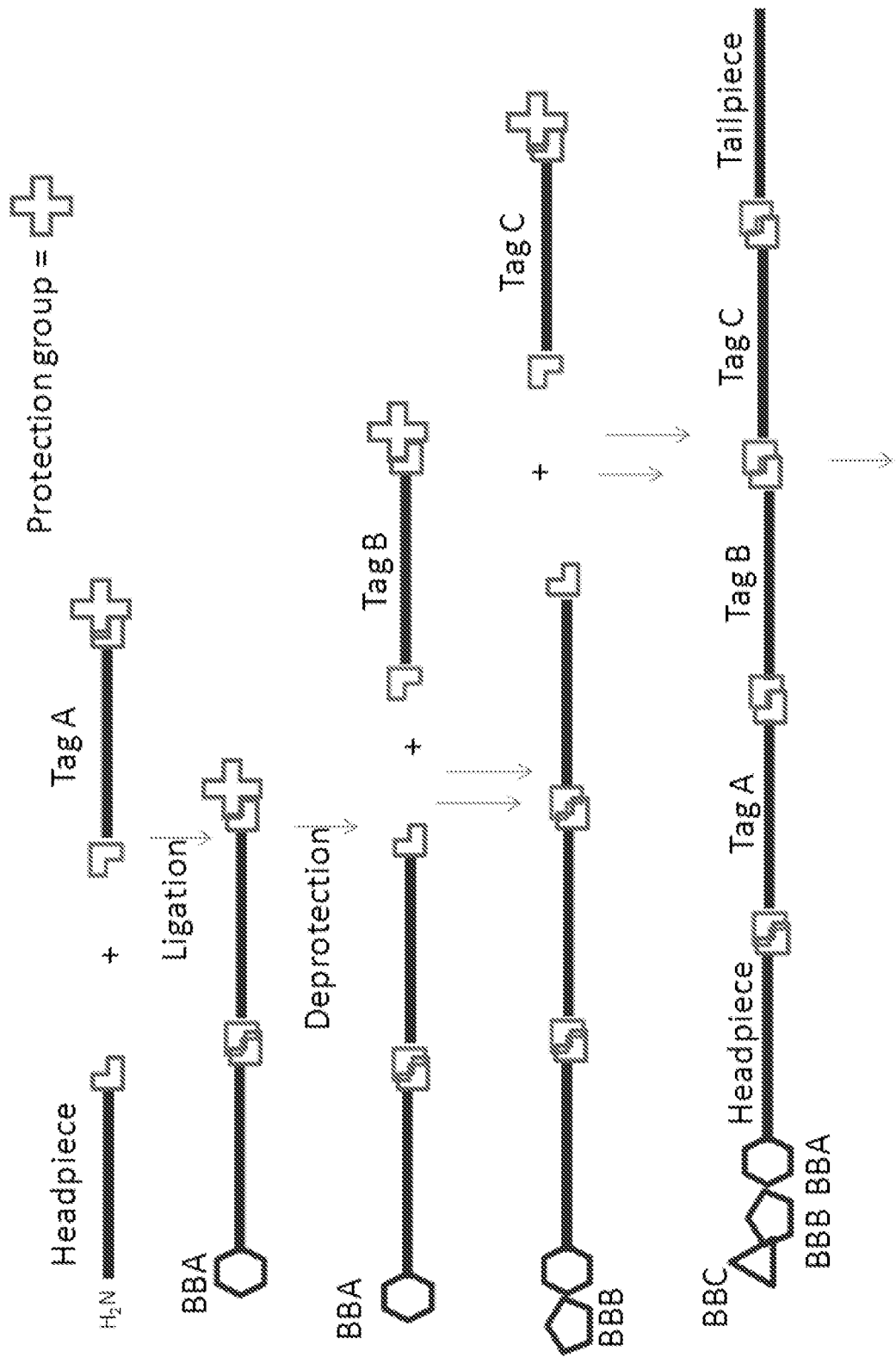
FIG. 15A is an exemplary schematic showing the chemical ligation of encoding DNA tags using a single chemistry that is not splint-dependent, e.g. 5'-azido/3'-alkynyl. The reactive groups are present on the 3' and 5' ends of each tag (Tag A, B, and C), and one of the reactive groups on either end (for example, the 3' end) is protected to prevent the cyclization, polymerization, or wrong-cycle ligation of the tags. The cycle of tag ligation includes chemical ligation, followed by deprotection of the remaining functional group to render the growing ligated entity competent for the next cycle of ligation. Each cycle also includes addition of one or more building blocks (BBA, BBB, and BBC, which are encoded by Tag A, B, and C, respectively). The chemical ligation process can optionally include addition of a tailpiece.
Figure 15B:
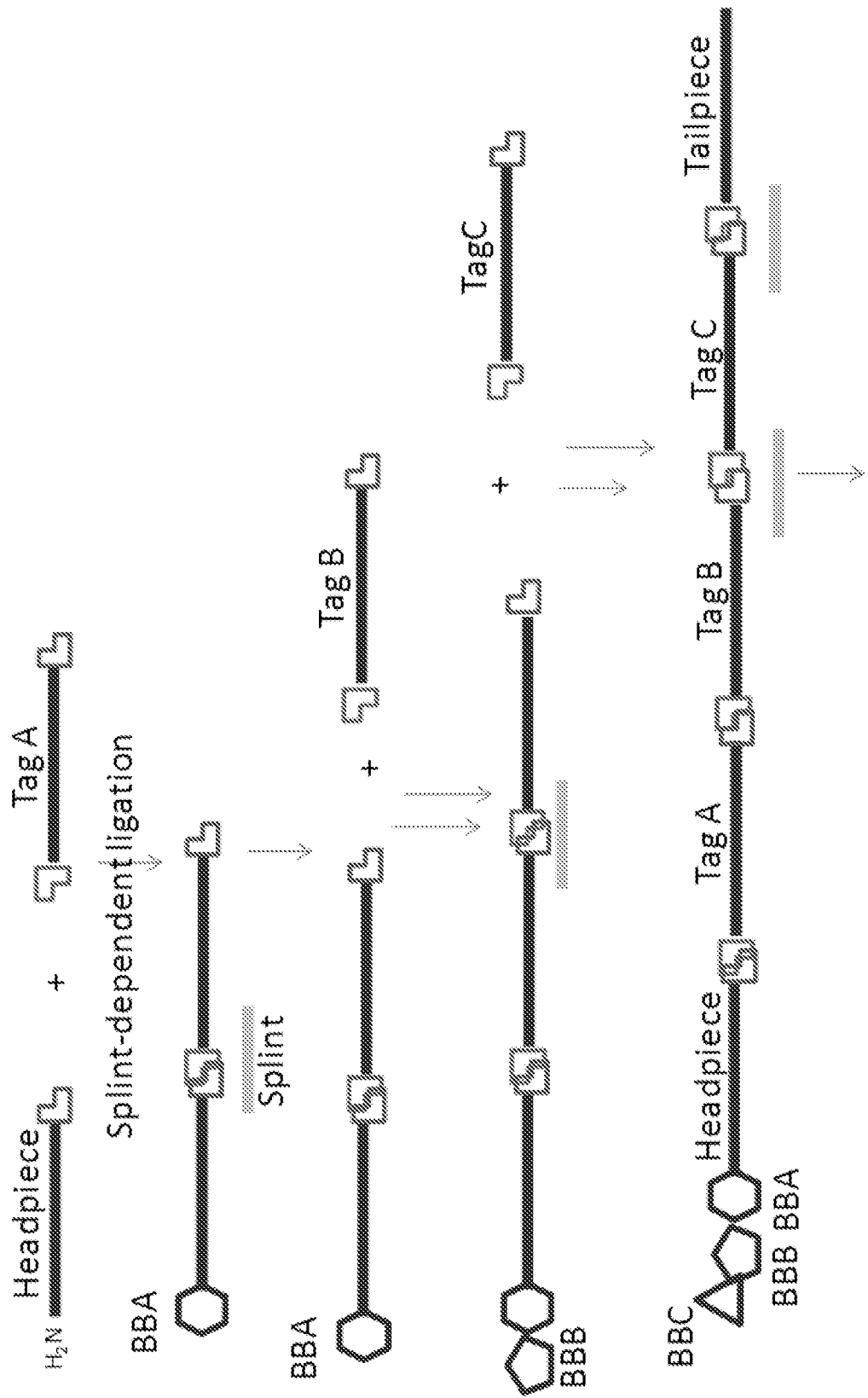
FIG. 15B is an exemplary schematic showing the chemical ligation of encoding DNA tags using a single chemistry that is splint-dependent. The template-dependent nature of this approach reduces the frequency of occurrence of tag polymerization, tag cyclization, as well as of mistagging events. Similar to FIG. 15A, this schematic includes tags (Tag A, B, and C) and one or more building blocks encoded by tags (BBA, BBB, and BBC).
Figure 15C:
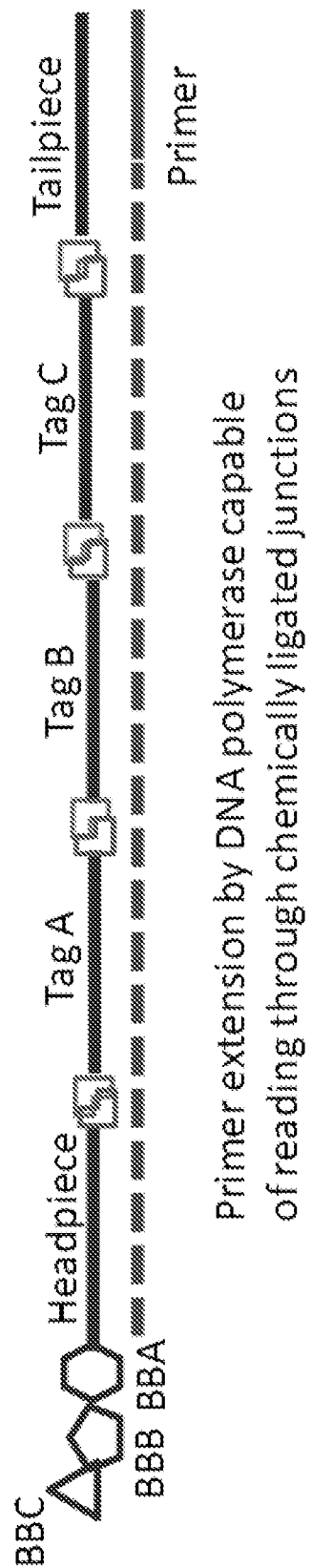
FIG. 15C is an exemplary schematic showing the use of a succession of chemically ligated tags as a template for template-dependent polymerization, generating cDNA that is competent for PCR amplification and sequencing, as well as using a template-dependent polymerase capable of reading through the chemically ligated junctions.

Encoding with Chemically Ligated DNA Tags Using the Same Chemistry for Each Ligation Step Encoding DNA tags can be ligated enzymatically or chemically. A general approach to chemical DNA tag ligation is illustrated in FIG. 15A. Each tag bears co-complementary reactive groups on its 5' and 3' ends. In order to prevent polymerization or cyclization of the tags, either (i) protection of one or both reactive groups (FIG. 15A), e.g., in case of TIPS-protected 3' alkynes, or (ii) splint-dependent ligation chemistry (FIG. 15B), e.g., in the case of 5'-iodo/3'-phosphorothioate ligation, is used. For (i), unligated tags can be removed or capped after each library cycle to prevent mistagging or polymerization of the deprotected tag. This step may be optional for (ii), but may still be included. Primer extension reactions, using polymerase enzymes that are capable of reading through chemically ligated junctions, can also be performed to demonstrate that ligated tags are readable and therefore the encoded information is recoverable by post-selection amplification and sequencing (FIG. 15C).

Figure 16A:
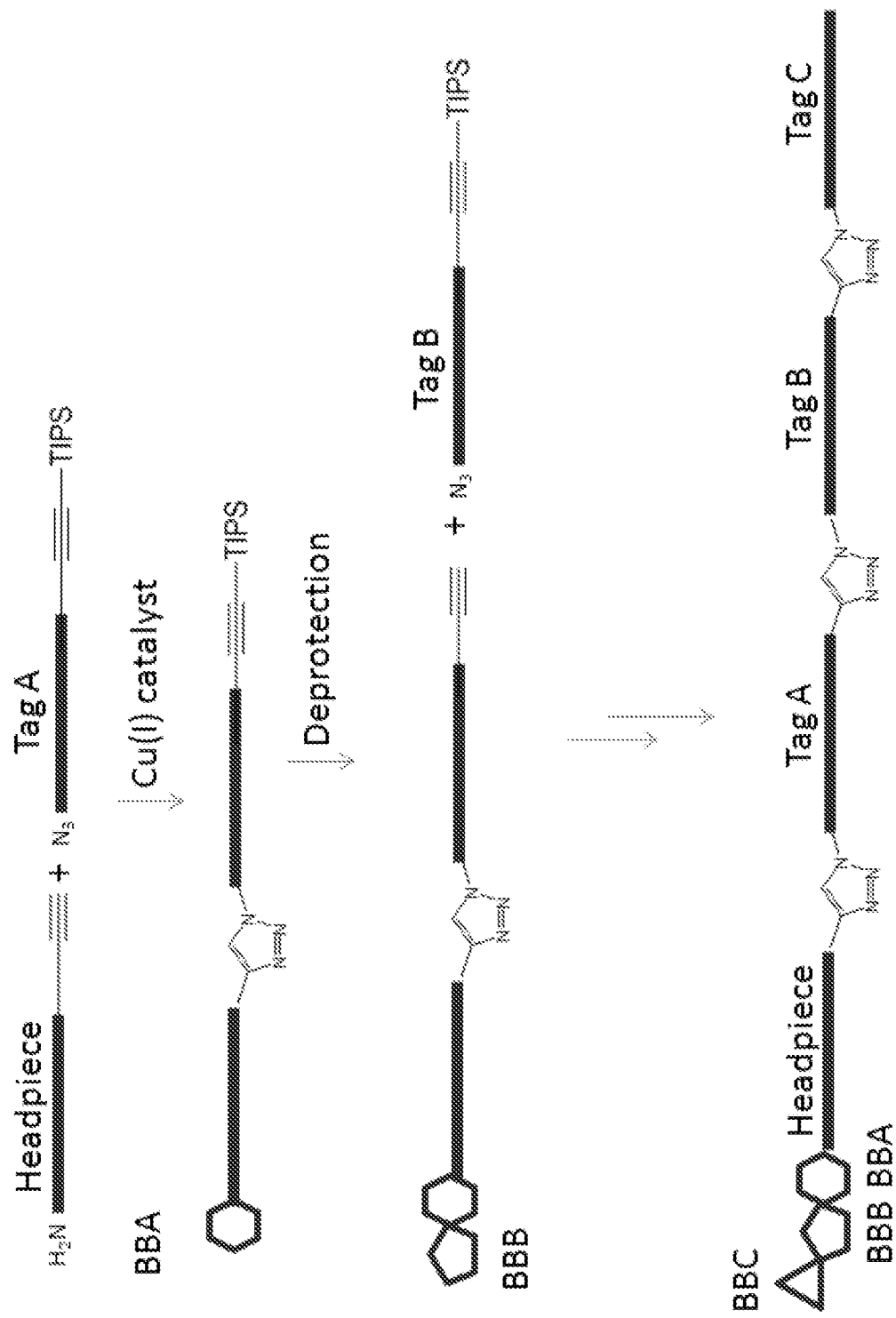
FIG. 16A is an exemplary schematic showing the chemical ligation of encoding DNA tags using TIPS-protected alkynyl tags and "click" chemistry. Each cycle of library synthesis includes Cu(I)-catalyzed chemical ligation of the TIPS-protected tag to the deprotected alkyne from the previous cycle. After the ligation, the TIPS group is removed (deprotected), thereby activating the alkyne for the next chemical ligation step.

A library tagging strategy that implements ligation of the tags using "click-chemistry" (Cu(I) catalyzed azide/alkyne cycloaddition) is shown in FIG. 16A. The implementation of this strategy relies on the ability of precise successive ligation of the tags, avoiding mistagging, and tag polymerizations, as well as the ability to copy the chemically ligated DNA into amplifiable natural DNA (cDNA) for post-selection amplification and sequencing (FIG. 16C).

Figure 16B:
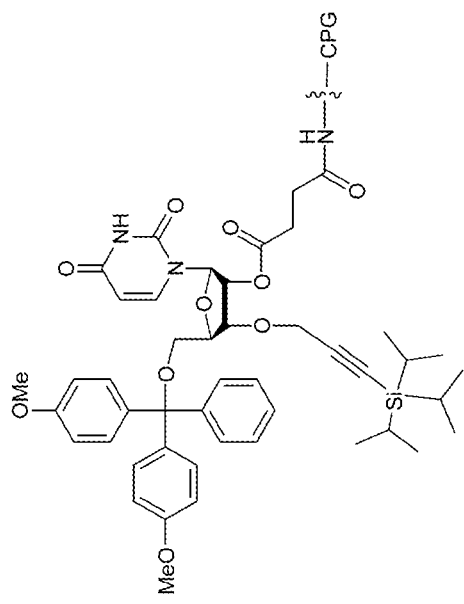
FIG. 16B shows the structure of DMT-succinyl-3'-O-TIPS-propargyl uridine CPG that is used to initiate solid-phase synthesis of oligonucleotides bearing 3'-O-TIPS-propargyl uridine at the 3'-terminus.
Figure 16C:
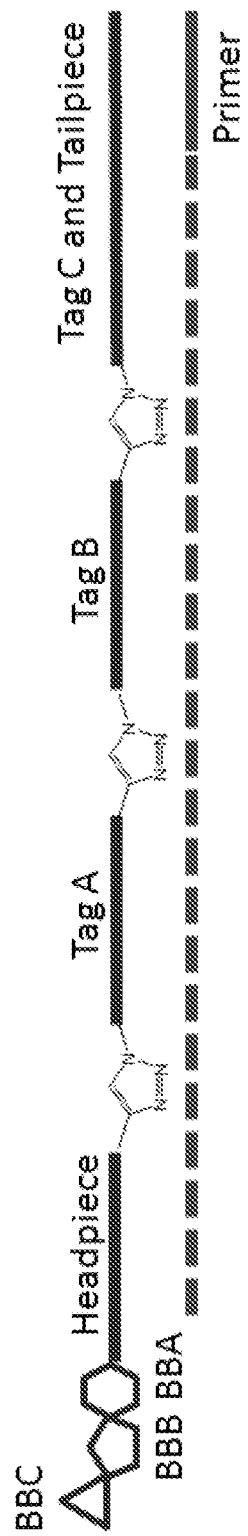
FIG. 16C is an exemplary schematic showing the use of a succession of "click" chemically ligated tags as a template for template-dependent polymerization, generating cDNA that is competent for PCR amplification and sequencing, as well as using a template-dependent polymerase capable of reading through the "click" chemically ligated junctions.

To achieve accurate tag ligation triisopropylsilyl (TIPS)-protected 3' propargyl nucleotides, (synthesized from propargyl U in the form of a CPG matrix used for oligonucleotide synthesis) was used (FIG. 16B). The TIPS protecting group can be specifically removed by treatment with tetrabutylammonium fluoride (TBAF) in DMF at 60° C. for 1-4 hours. As a result, the ligation during library synthesis includes a 5'-azido/3'-TIPS-propargyl nucleotide (Tag A) reacting with the 3'-propargyl of the headpiece through a click reaction. After purification, the previous cycle is treated with TBAF to remove TIPS and generate the reactive alkyne which in turn reacts with the next cycle tag. The procedure is repeated for as many cycles as it is necessary to produce 2, 3 or 4 or more successively installed encoding tags (FIG. 16A).

Materials and Methods

Oligos: The following oligos were synthesized by Trilink Biotechnologies, San Diego Calif.: ss-HP-alkyne: 5'-NH$_2$-TCG AAT GAC TCC GAT AT (3'-Propargyl G)-3'(SEQ ID NO: 32); ss-azido-TP: 5'-azido dT ATA GCG CGA TAT ACA CAC TGG CGA GCT TGC GTA CTG-3'(SEQ ID NO: 33); and B-azido: 5' azido dT ACA CAC TGG CGA GCT TGC GTA CTG-3' (SEQ ID NO: 34).

ClickTag-TIPS: 5'-azdido dT AT GCG TAC AGT CC (propargyl U-TIPS)-3' (SEQ ID NO: 35) and 5'Dimethoxytrityl 2'-succinyl 3'-O-(triisopropyl silyl) Propargyl uridine cpg were synthesized by Prime Organics, Woburn Mass.

The following oligos were synthesized by IDT DNA technologies, Coralville, Iowa: FAM-click-primer: (5'-6-FAM) CAG TAC GCA AGC TCG CC-3' (SEQ ID NO: 36) and Cy5-click-primer: (5'-Cy5) CAG TAC GCA AGC TCG CC-3' (SEQ ID NO: 37).

DNA55-control: /5'Biotin-TEG//ispC3//ispC3/-TCGAATGACTCCGATATGT ATA GCG CGA TAT ACA CAC TGG CGA GCT TGC GTA CTG-3' (SEQ ID NO: 38).

rDNA55-control: /5Bio-TEG//ispC3//ispC3/-TCGAATGACTCCGATAT(riboG)T ATA GCG CGA TAT ACA CAC TGG CGA GCT TGC GTA CTG-3' (SEQ ID NO: 39)

Synthesis of the templates: In the following examples, the phrase "chemically ligated tags", or control sequences related to them, are referred to as "templates" because the subsequent step ("reading") utilizes them as templates for template-dependent polymerization.

Tag ligation: To a solution of 1 equivalent (1 mM) of ssHP-alkyne and 1 equivalent (1 mM) of ss-azidoTP in 500 mM pH 7.0 phosphate buffer, was added a solution of pre-mixed 2 eq of Cu(II)Acetate (to a final concentration of 2 mM), 4 eq of sodium ascorbate (to a final concentration of 4 mM), 1 eq TBTA (to a final concentration of 1 mM) in DMF/water. The mixture was incubated at room temperature overnight. After LC-MS confirmation of the completion of the reaction, the reaction was precipitated using salt/ethanol.

"Single click" templates Y55 and Y185 were synthesized by the reaction of ss-HP-alkyne with ss-azido-TP and B-azido, respectively. Double and triple click templates (YDC and YTC) were synthesized by click ligation of ss-HP-alkyne with ClickTag-TIPS, followed by deprotection of TIPS using TBAF (tetrabutylammonium fluoride) in DMF at 60° C. for an hour, followed by click ligation with ss-azido TP. For triple click template (YTC), the ligation and deprotection of ClickTag-TIPS was repeated twice.

Figure 17A:
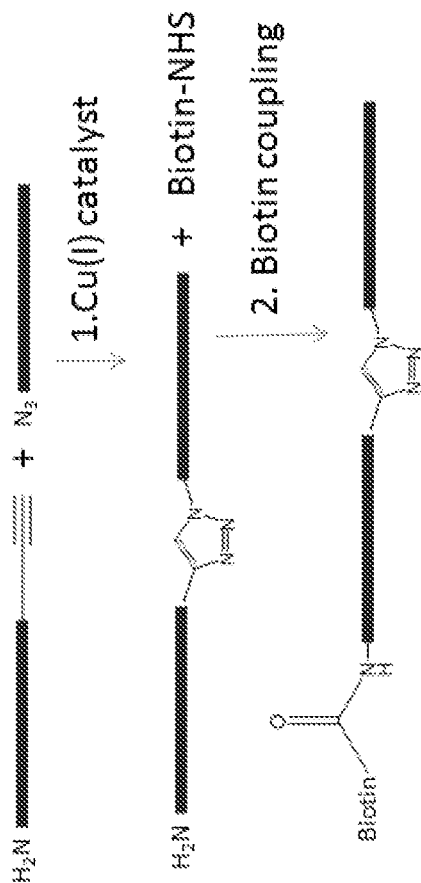
FIGS. 17A-17C show the synthesis of 5'-biotinylated, "single-click" templates Y55 and Y185.

The templates were reacted with biotin-(EG)$_4$-NHS and desalted (FIG. 17A). The final products were purified by RP HPLC and/or on a 15-20% polyacryl amide gel/8M urea and analyzed by LC-MS.

Enzymes: The following DNA polymerases with their reaction buffers were purchased from New England Biolabs: Klenow fragment of E. coli DNA polymerase I, Klenow fragment (exo-), E. coli DNA polymerase I, Therminator™, 9° N™, Superscript III™.

Streptavidin magnetic Dynabeads® M280 were purchased from Invitrogen.

Template-dependent polymerization assessment: Each template (5 µM) was incubated with 1 equivalent of either Cy5 or FAM Click-primer in 40 to 50 µL of the corresponding 1× reaction buffer and each enzyme, using reaction conditions according to the manufacturer's guidelines for 1 hour. Certain reactions (such as SSII or SSIII transcriptions) were additionally supplemented with 1 mM MnCl$_2$. The product of the reaction was loaded on 125 µL of pre-washed SA beads for 30 minutes with shaking. The beads were then collected, and the flowthrough was discarded. Beads were washed with 1 mL of Tris-buffered saline (pH 7.0) and eluted with 35 µL, of 100 mM NaOH. The eluate was immediately neutralized by adding 10 µL of 1 M Tris HCl, pH 7.0. The products were analyzed using LC-MS.

Results and Discussion

Figure 17C:
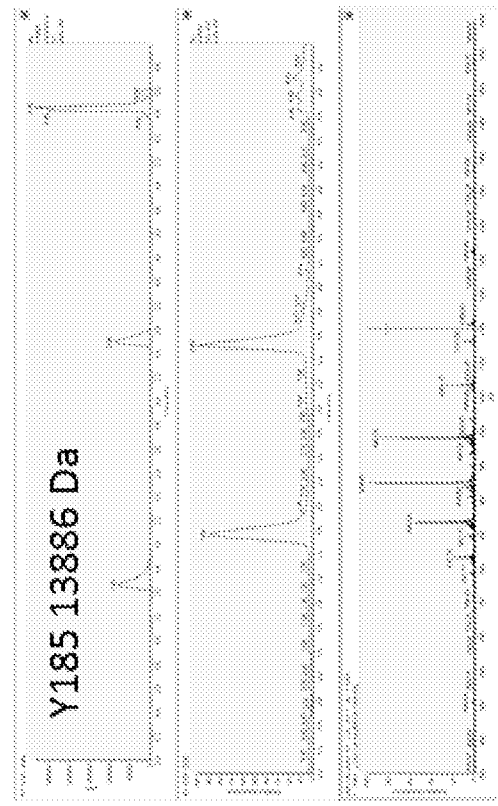
Figure 17B:
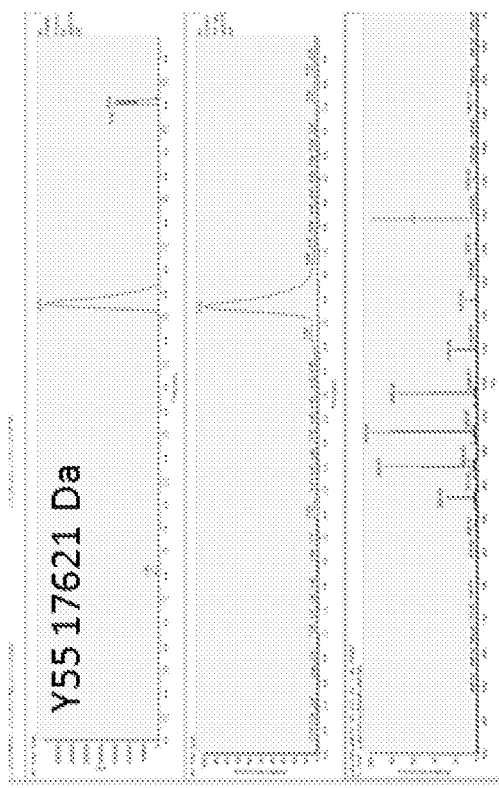

Template Preparation: Each template, Y55, Y185 (FIGS. 17B and 17C), YDC and YTC (FIG. 19) was synthesized and purified to greater than 85% purity (the major impurity being un-biotinylated template). LC-MS revealed the following MWs for the templates: Y55 17,624 (calculated 17,619) Da; YDC 22,228 (calculated 22,228) Da; and YTC 26,832 (calculated 26,837) Da.

The single click templates Y55 and Y185 (FIGS. 17B and 17C) were synthesized from oligonucleotides that bear only one click chemistry functionality (alkyne or azide). The efficiency of the click reaction (chemical ligation) was over 90% in an overnight reaction using Cu(I) catalyst generated in situ.

Templates YDC and YTC (FIGS. 19A-19D) serve to demonstrate successive chemical ligations. Both YDC and YTC use individual tags which simultaneously contain both azido and TIPS-protected alkyne functionalities. Template YTC demonstrates three successive cycles of tagging as may be used to encode three steps of chemical library generation.

All of the above templates were tested for primer extension through and beyond the click-ligation linkages to demonstrate that ligated tags are readable, and therefore that encoded information is recoverable.

Figure 18A:
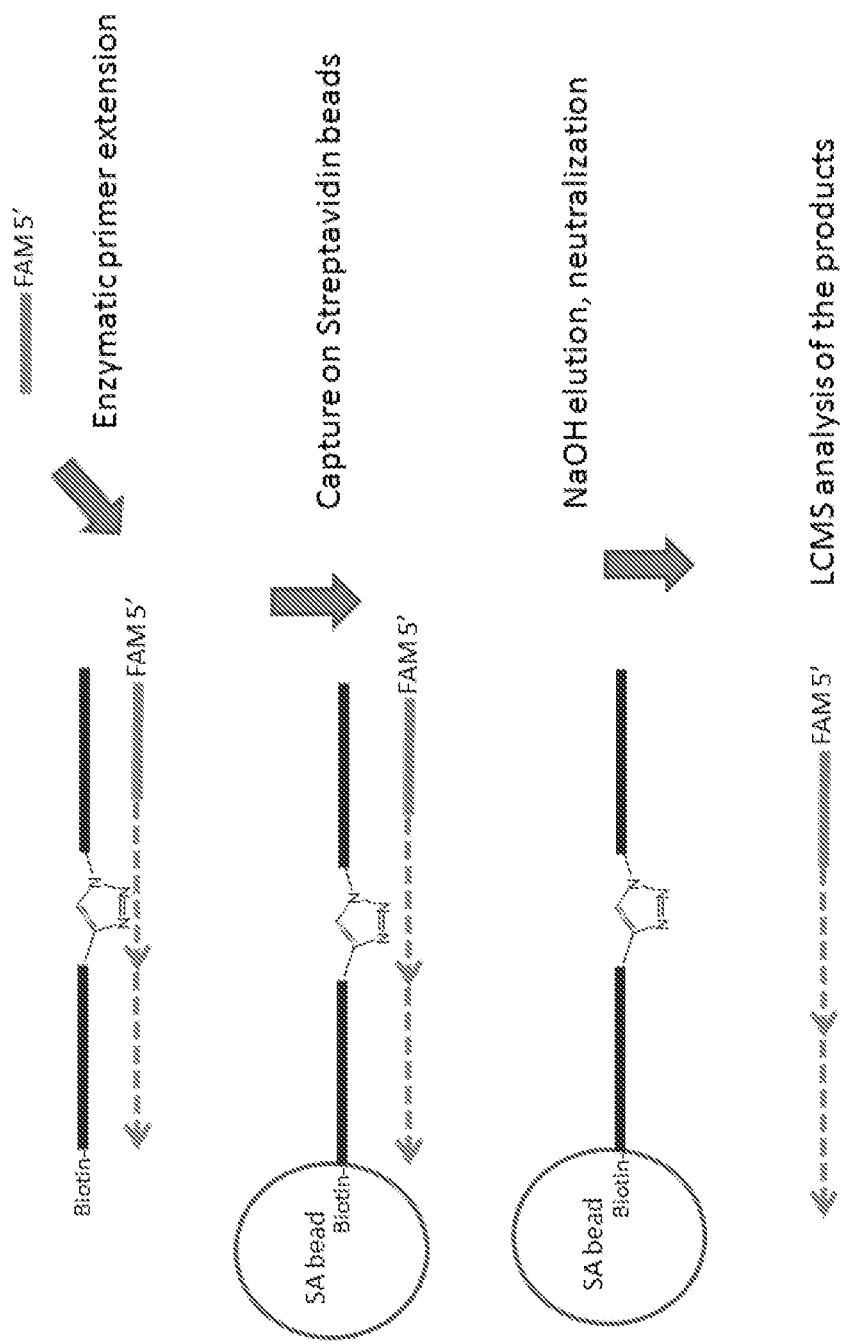
FIGS. 18A-18C provide an exemplary assay for the "read-through" of a "single-click" template.

Template-Dependent Polymerization Using "Single-Click" Template Y55:

A large set of polymerases was tested to read through a triazole click linkage (FIG. 18A). Initial experiments were performed using Cy5-click-primer. In later experiments FAM-click-primer was used. The fluorophore had no effect on the copying of the template, i.e., the results were equivalent using either primer. As a control template DNA55-control and rDNA55-control were used (to test the effect of a single ribonucleotide in the template, since propargyl-G used for a click ligation is a ribonucleotide derivative).

Expected full length products in all three templates have the same molecular weight, which is 17446 (FAM primer) (FIG. 18B) or 17443 (Cy5 primer). A small amount of the product which corresponds to primer extension up to, but stopping at, the click ligation linkage (11880 Da) was also observed for some polymerases.

A set of polymerases that can produce substantial degree of read-through of the click linkage (production of full-length cDNA) were discovered and are tabulated below.

| Full-length cDNA yields of over 50% |
| --- |
| Klenow fragment of E. coli DNA polymerase I |
| Klenow fragment (exo-) |
| E. coli DNA polymerase I |
| Therminator ™ |
| 90°N ™ |
| Superscript III ™ supplemented with 1 mM MnCl$_2$ |

Figure 18C:
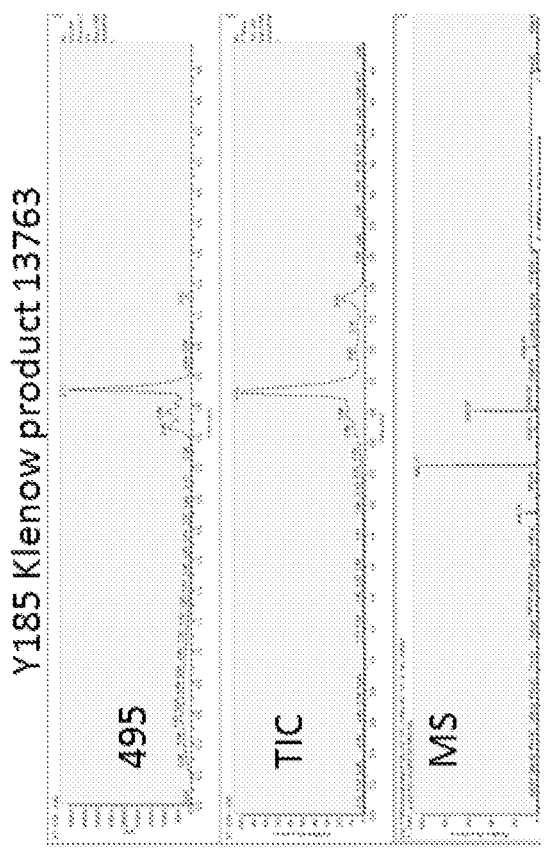
Figure 18B:
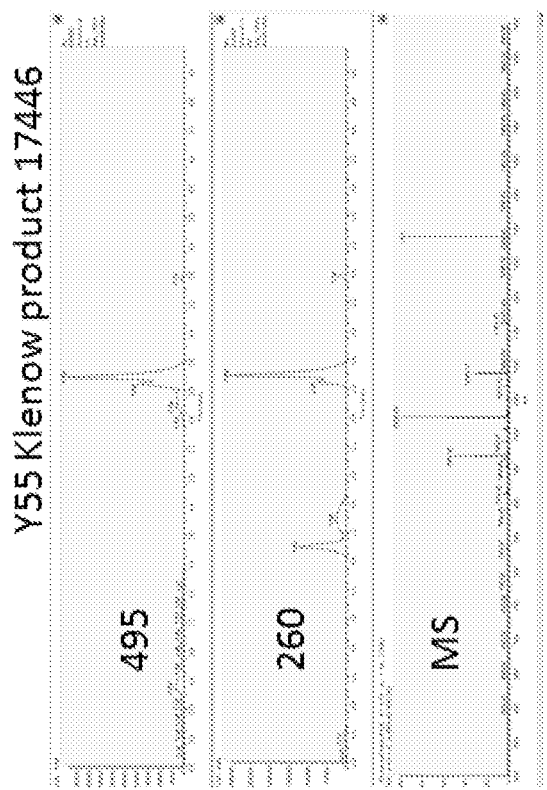
Figure 19A:
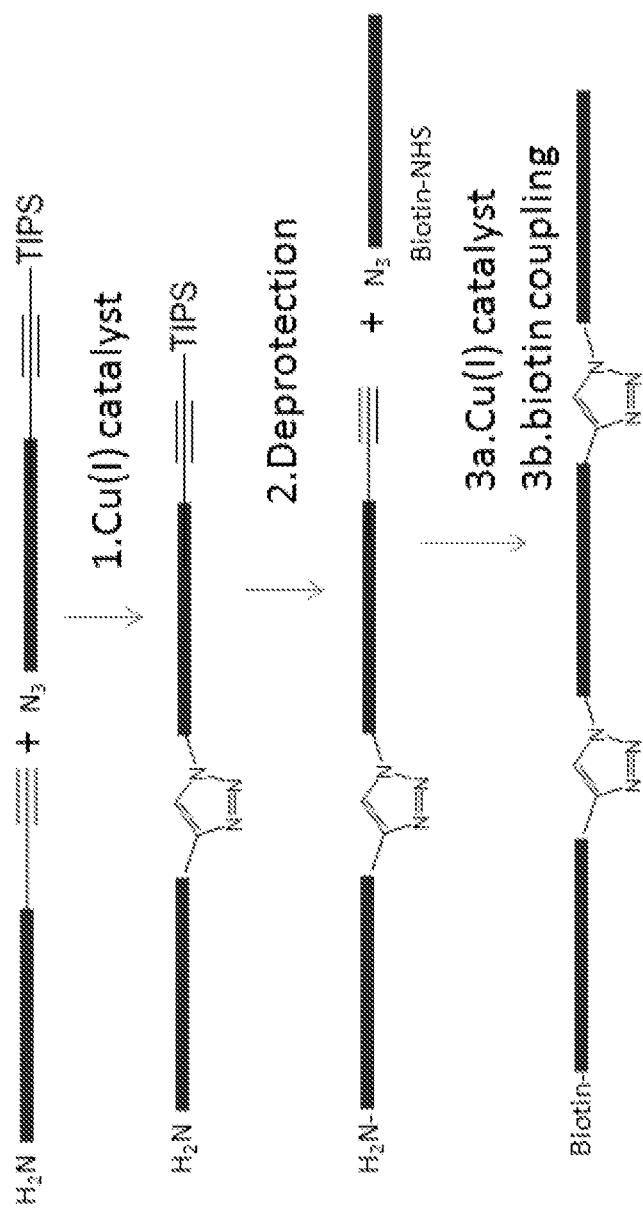
FIGS. 19A-19D provides the synthesis of 5'-biotinylated "double-click" template YDC and "triple-click template" YTC using a TIPS-protected alkynyl tag.
Figure 19B:
Figure 19D:
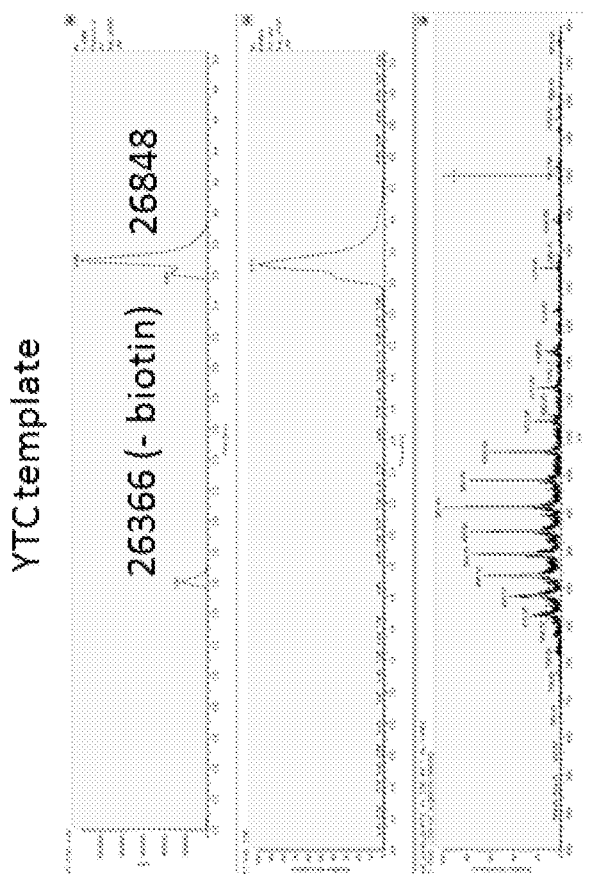
Figure 19C:
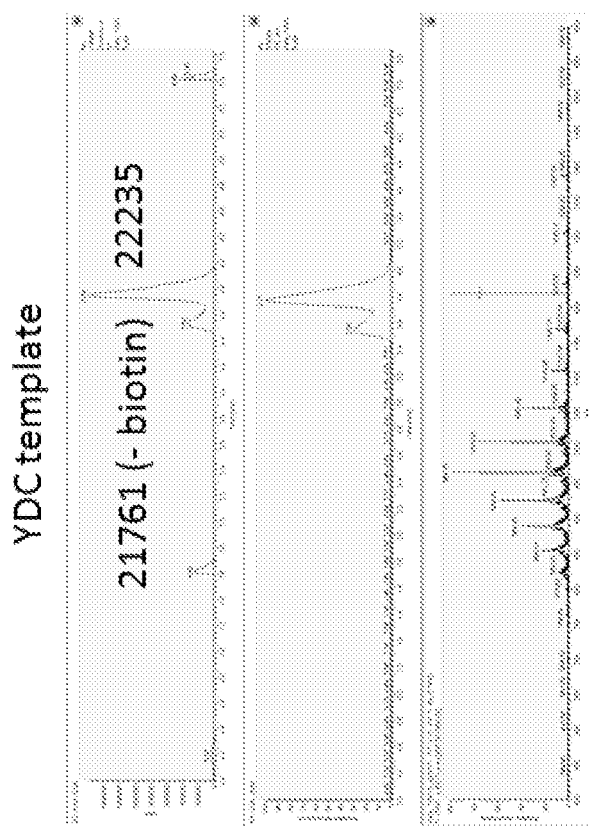

The highest yields (over 80% read-through at a single click junction) were achieved when using Klenow fragment with incubation at 37° C. (FIG. 18B). Somewhat lower yield was observed using E. coli DNA polymerase I. 50% yields with Therminator™ and 9° N™ polymerases, as well as Klenow fragment exo- were achieved.

Superscript III™ reverse transcriptase produced about 50% yield of cDNA when the buffer was supplemented with 1 mM MnCl$_2$. However, manganese caused the mis-incorporation of nucleotides which was observed by MS, i.e., polymerization fidelity was reduced.

Template-Dependent Polymerization Using "Single-Click" Template Y185:

Template Y185 features the same primer binding site as all templates used in this example, except, due to a different tailpiece B-azido, the distance between the last nucleotide of the primer binding site to the click linkage is 8 nucleotides, as compared to 20 nucleotides in Y55 and all other templates. The template was used to test whether transcription of a click linkage was still possible when the enzyme was in initiation-early elongation conformation. Klenow was capable of copying the Y185 template with similar efficiency to Y55, opening the possibility of reducing the length of the click-ligated encoding tags (FIG. 18C).

Figure 20A:
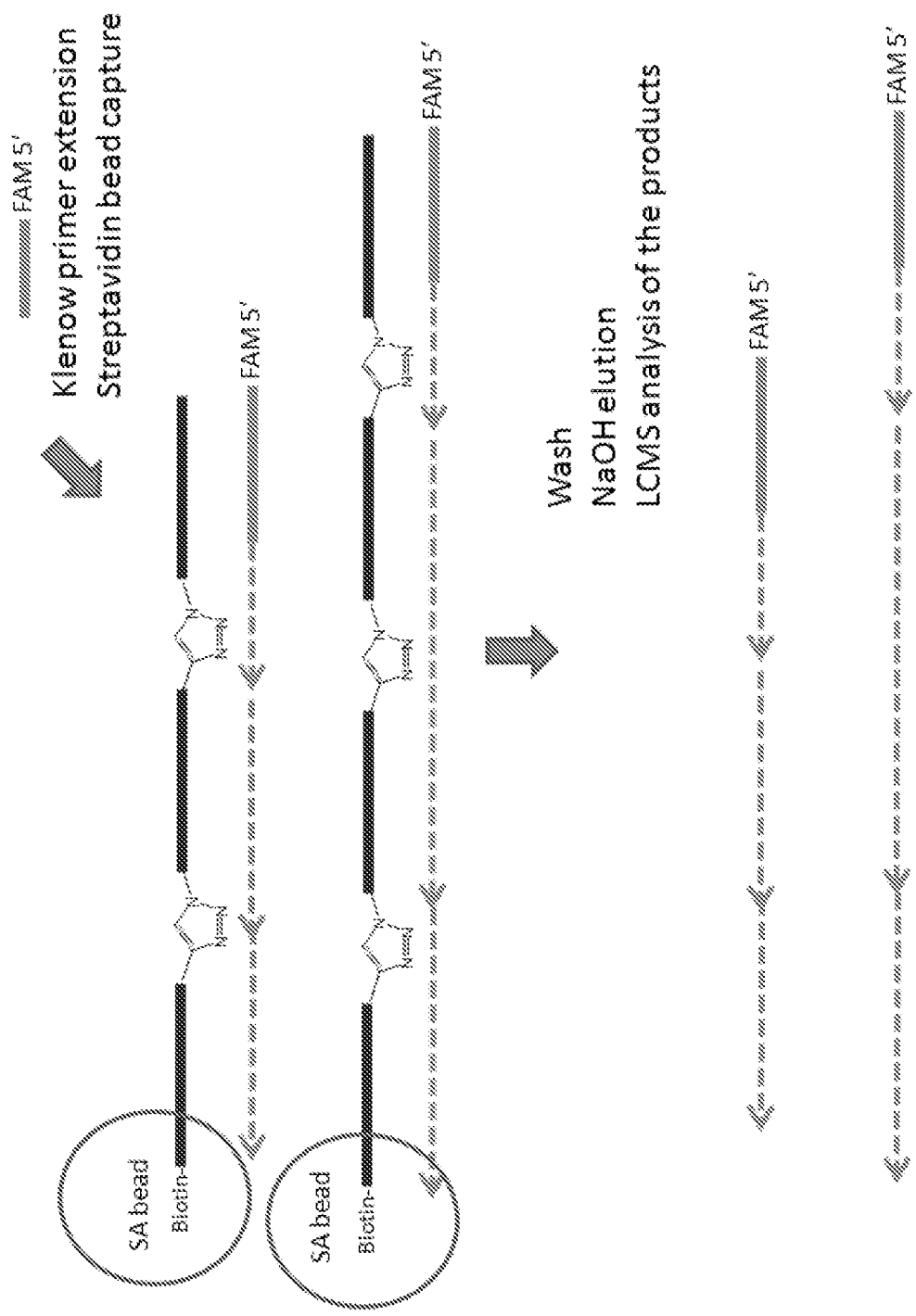
FIGS. 20A-20C provide an exemplary click "read-through" assay using "double-click" and "triple-click" templates.

Template-Dependent Polymerization Using Double and Triple Click-Ligated Templates YDC and YTC:

After establishing that the Klenow fragment was the most efficient enzyme to read through the click ligation linkages under the assay condition employed, cDNA using YDC and YTC templates (FIGS. 20A-20C) were also generated. Primer extension reactions with both YDC and YTC templates produced full length products. Other observed products, which composed around 10-15% of total reaction output, corresponded to partially extended primer, stalled at each click junction, such as e.g., 11880 Da and 16236 Da. The yields were measured by LC-MS analysis in the presence of the internal standard and were about 80-90% per junction (i.e., around 85% for 1 click, 55% for 2-click and 50% for 3-click templates, see FIG. 21).

Figures 20B, 20C:
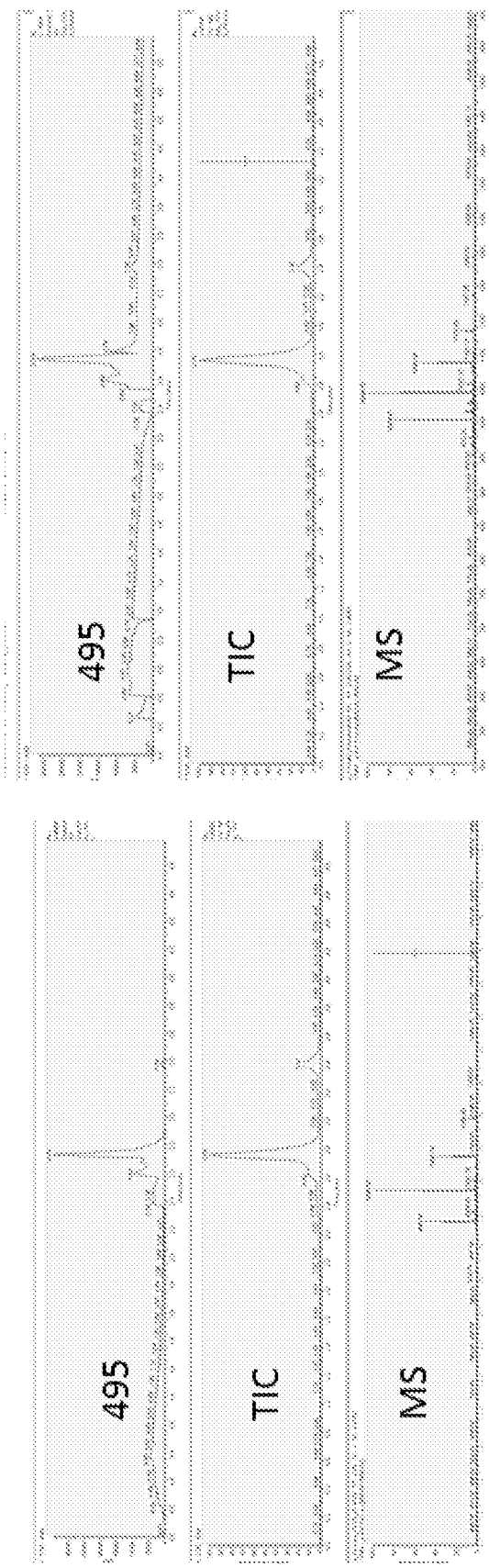
Figure 21:
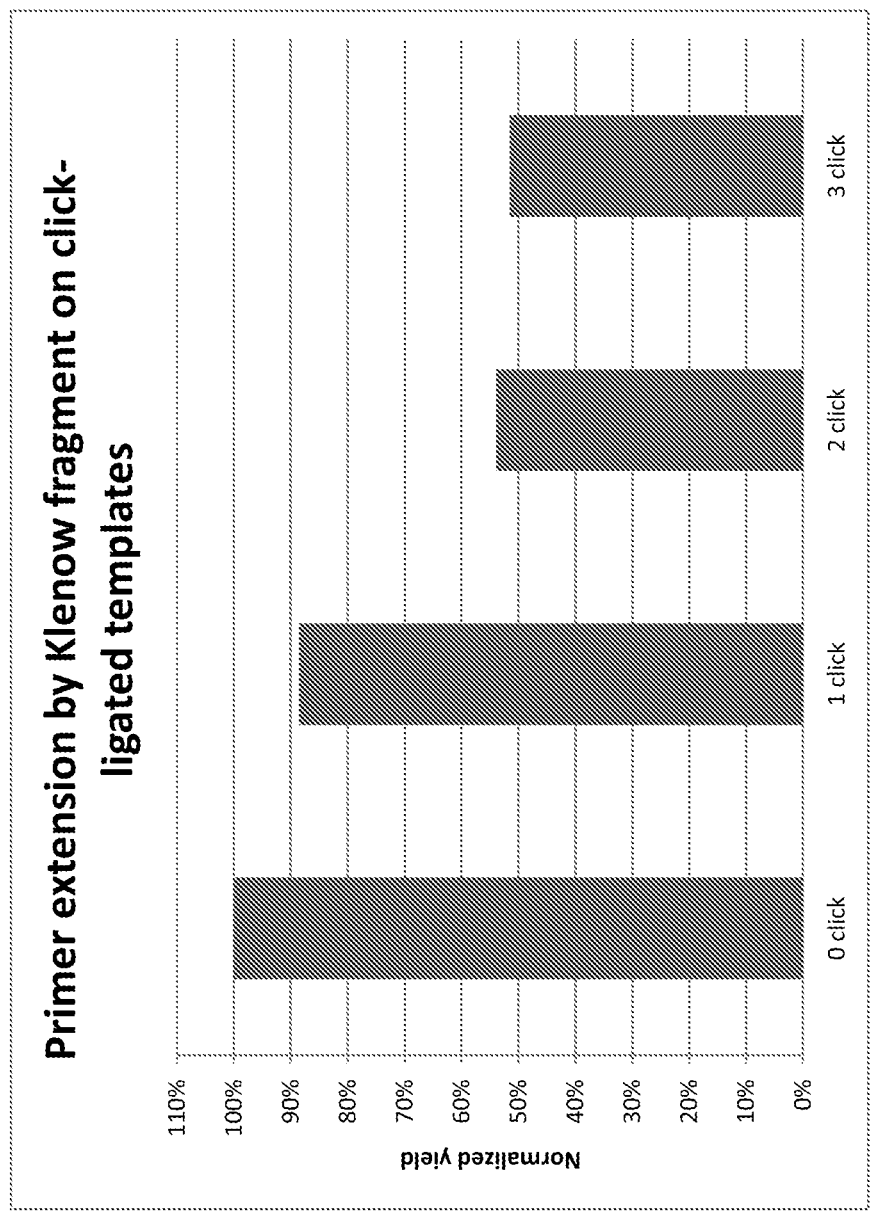
FIG. 21 is a graph showing the efficiency of the click "read-through" using "single-click", "double-click" and "triple-click" templates in comparison to a control "no-click" DNA template. These data were obtained using the "read-through" assay described herein, and the yields were measured by LC MS analysis by comparison to an internal standard.

The product of YDC transcription lacked 1 dA nucleotide (calculated 22110, observed 27197 Da; −313 dA FIG. 20B) and the product of YTC transcription lacked 2 dA nucleotides (calculated 26773, observed 26147; −626 2×dA) (FIG. 20C). This correlates with the number of propargyl U nucleotides in the template. Without wishing to be limited by mechanism, it can be hypothesized that Klenow skipped over those U's in the context of T-triazole-U junction. In contrast, the propargyl G nucleotide in the 1$^{st}$ click junction was correctly copied.

Example 10

Figure 24A:
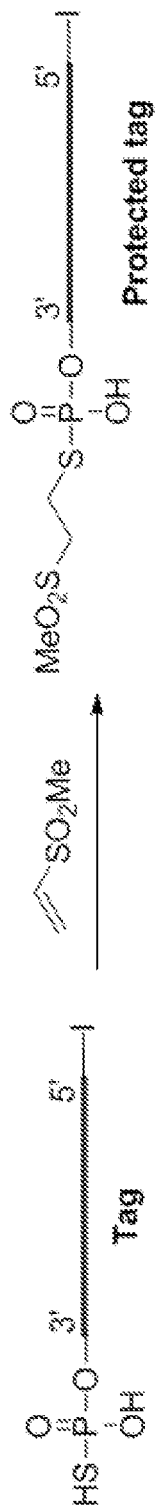
FIGS. 24A-24B show the protection and use of 3'-phosphorothioate/5'-iodo groups on DNA tags.

Use of 3'-phosphorothioate/5'-iodo Tags to Chemically Ligate a Succession of Encoding DNA Tags that Encode a Chemical Library Covalently Installed Upon the 5'-Terminus Protection of 3'-phosphorothioate on Tag:

As shown in FIG. 24A, a 5'-iodo-3'-phosphorothioate tag (1 eq.) was dissolved in water to give a final concentration of 5 mM. Subsequently, vinyl methyl sulfone (20 eq.) was added and the reaction was incubated at room temperature overnight. Upon completion of the reaction, the product was precipitated by ethanol.

Figure 24B:
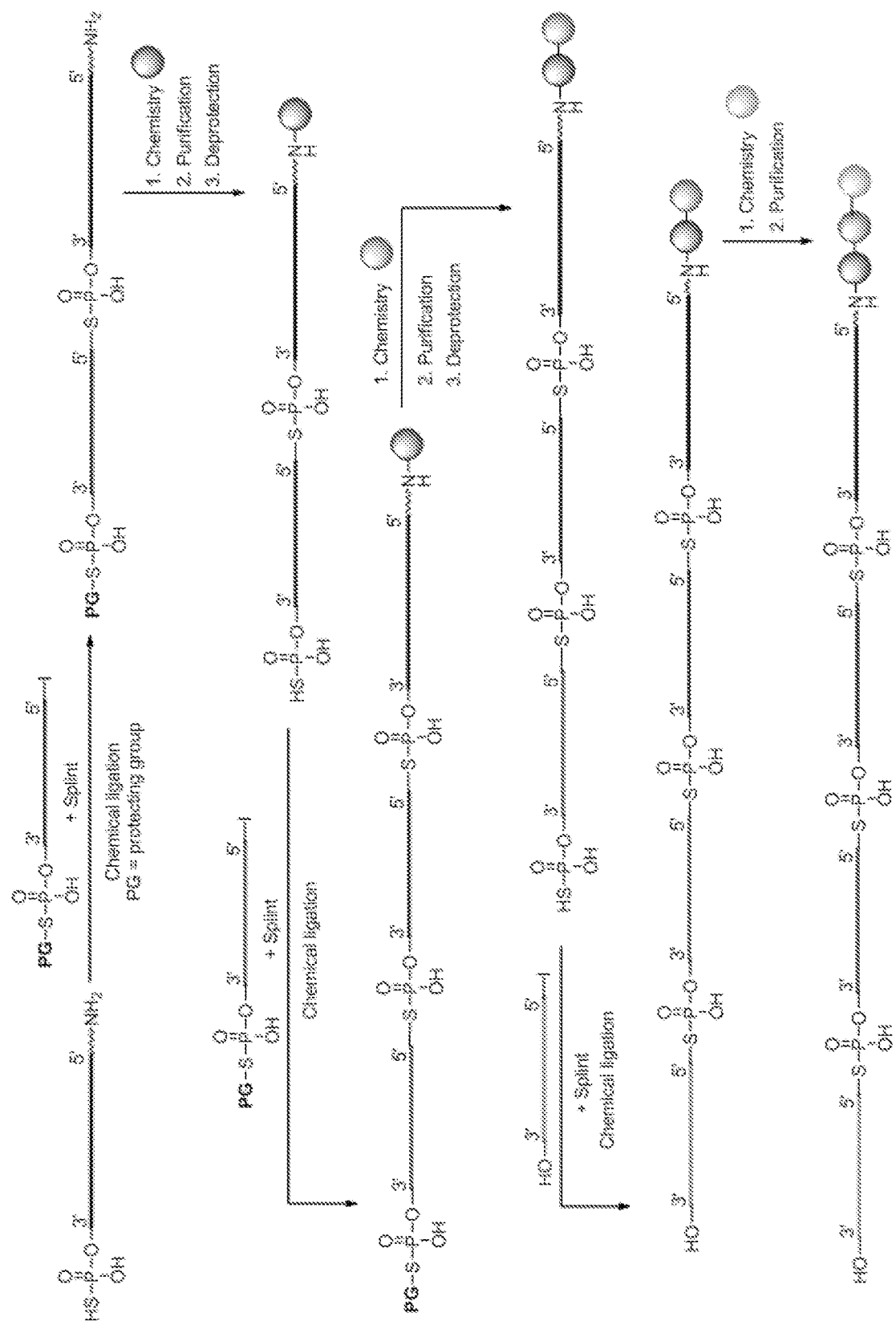

Library Synthesis (FIG. 24B)

Cycle A:

To each well in the split was added single-stranded DNA headpiece (1 eq., 1 mM solution in 500 mM pH 9.5 borate buffer), one cycle A protected tag (1.5 eq.), and splint (1.2 eq.). The chemical ligation was incubated at room temperature overnight. To each well (in the split) was then added one Fmoc amino acid (100 eq.), followed by 4-(4,6-dimethoxy-1,3,5-triazin-2-yl)-4-methylmorpholinium chloride (100 eq.). The chemical reaction was incubated at room temperature overnight. Upon completion, all wells were pooled and the products precipitated using ethanol. The cycle A pool was purified using LC and lyophilized to dryness, and then dissolved in water to give a 1 mM final concentration and piperidine (10% v/v) was added to perform the deprotection of cycle A tag (60° C., 2 h). The deprotected product was precipitated again using ethanol.

Cycle B:

The deprotected cycle A pool was dissolved in 500 mM, pH 9.5, borate buffer to give a 1 mM concentration and then split into separate reaction wells (1 eq. of cycle A product in each well). To each well was added one cycle B protected tag (1.5 eq.), and splint (1.2 eq.). The chemical ligation was incubated at room temperature overnight. To each well (in the split) was added a mixture of one formyl acid (100 eq.), diisopropyl carbodiimide (100 eq.) and 1-hydroxy-7-aza-benzotriazole (100 eq.). The chemical reaction was incubated at room temperature overnight. Upon completion, all wells were pooled and the products precipitated using ethanol. The cycle B pool was purified using LC and lyophilized to dryness, and then dissolved in water to give a 1 mM final concentration and piperidine (10% v/v) was added to perform the deprotection of cycle B tag (60° C., 2 h). The deprotected product was precipitated again using ethanol.

Cycle C:

The deprotected cycle B pool was dissolved in 500 mM pH 5.5 phosphate buffer to give a 1 mM concentration and then split into separate reaction wells (1 eq. of cycle B product in each well). To each well was added one cycle C tag (1.5 eq.) and splint (1.2 eq.). The chemical ligation was incubated at room temperature overnight. To each well (in the split) was added an amine (80 eq.) and sodium cyanoborohydride (80 eq.). The chemical reaction was incubated at 60° C. for 16 h. Upon completion, all wells were pooled and the products precipitated using ethanol. The cycle C pool was purified using LC and lyophilized to dryness.

Example 11

Figure 22A:
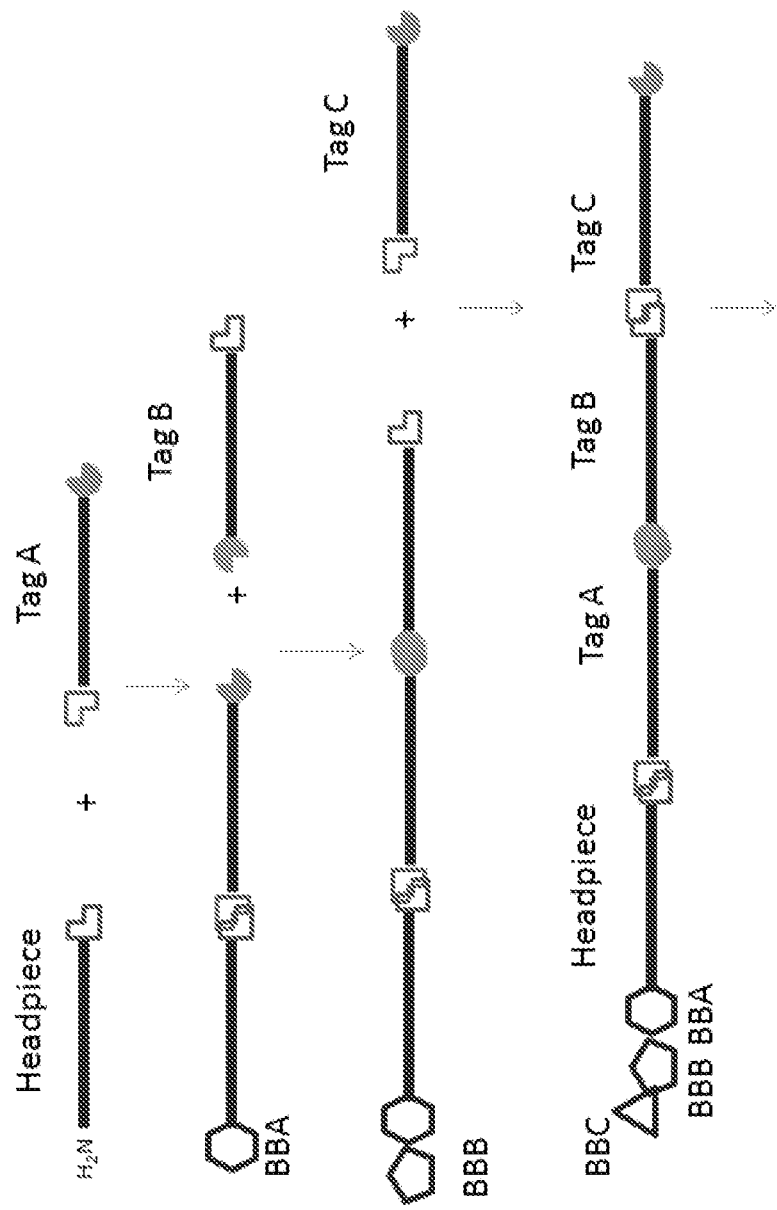

Encoding with Chemically Ligated DNA Tags Using a Pair of Orthogonal Chemistries for Each Successive Tag Ligation Step Another approach for generation of chemically ligated encoding DNA tags is the use of a pair of orthogonal chemistries for successive ligations (FIG. 22A). Tags that bear orthogonal reactive groups at their ends will not tag polymerize or cyclize, and the orthogonal nature of successive ligation steps will reduce the frequency of mistagging events. Such approaches require (i) having at least two orthogonal chemistries available for oligonucleotide conjugation, and (ii) available read-through strategy for each of the junctions thus created (FIGS. 22B and 22C). This approach may also obviate the need for the use of protection groups or capping steps, thereby simplifying the tag ligation process.

Figure 23:
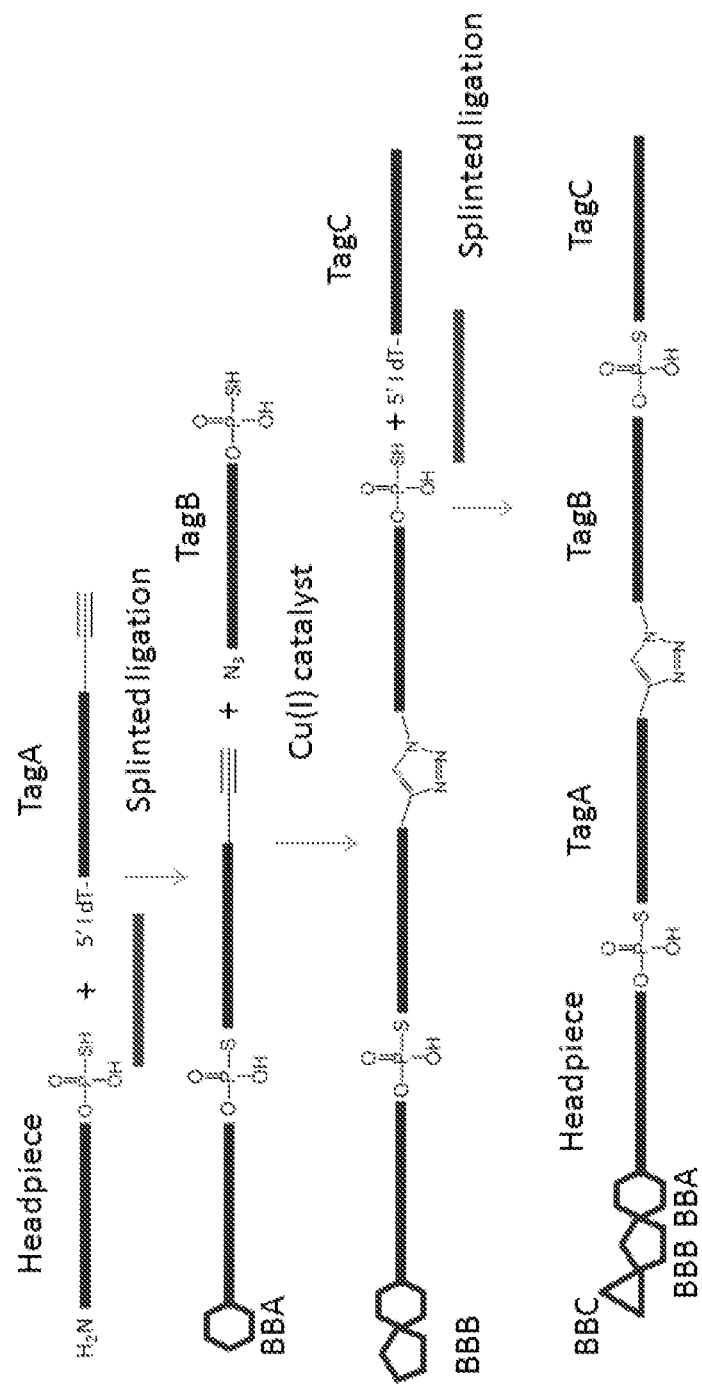
FIG. 23 is an exemplary schematic showing the chemical ligation strategy for DNA encoding tags that utilizes two specific successive orthogonal chemistries. Each tag contains click-reactive and phosphorothioate/iodo-reactive groups. Tags bearing orthogonal reactive groups at their 3' and 5' ends cannot polymerize and have a reduced frequency of occurrence of mistagging events. Without wishing to be limited, this approach may eliminate the need for the TIPS-protection of the 3'-alkyne. In cycle A, the 5'-iodo/3'-alkynyl tag is ligated using splint-dependent ligation to the 3'-phosphorothioate headpiece, leaving a reactive 3' alkyne for the next cycle of chemical ligation to a 5'-azido/3'-phosphorothioate tag. The orthogonal ligation cycles may be repeated as many times as is desired.
Figure 25A:
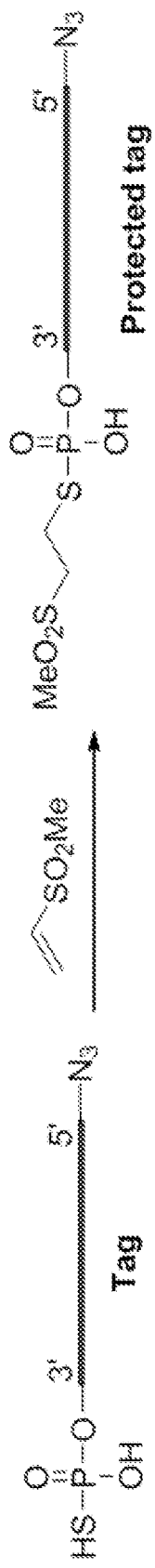
FIGS. 25A-25B show the protection and use of 3'-phosphorothioate groups on DNA tags.
Figure 25B:
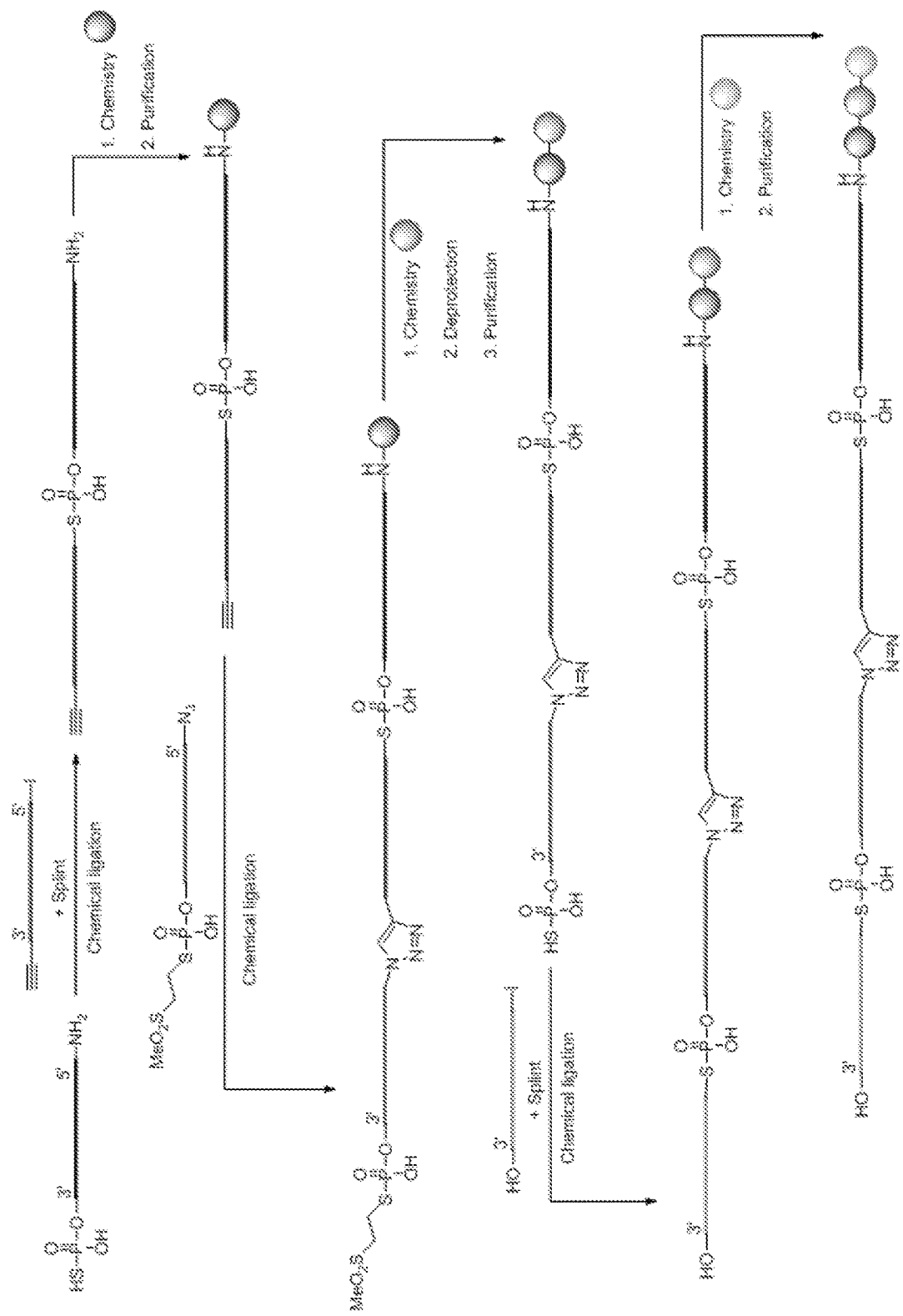

Orthogonal Chemical Ligation Strategy Utilizing 5'-Azido/3'-Alkynyl and 5'-Iodo/3'-Phosphorothioate Ligation for Successive Steps:

An example of the use of two orthogonal chemistries tag ligation is the combination of 5'-azido/3'-alkynyl and 5'-iodo/3'-phosphorothioate ligations. FIG. 23 shows an exemplary schematic of the synthesis of a 3-cycle orthogonal chemical ligation tagging strategy using these successive ligation chemistries. FIGS. 25A-25B show an example of the use of 3'-phosphorothioate/5'-azido and 3'-propargyl/5'-iodo tags to chemically ligate a succession of orthogonal encoding DNA tags that encode a chemical library covalently installed upon the 5'-terminus.

Protection of 3'-phosphorothioate on Tags:

As shown in FIG. 25A, a 5'-azido-3'-phosphorothioate tag (1 eq.) was dissolved in water to give a final concentration of 5 mM. Subsequently, vinyl methyl sulfone (20 eq.) was added and the reaction was incubated at room temperature overnight. Upon completion of the reaction, the product was precipitated by ethanol.

Library Synthesis (FIG. 25B)

Cycle A:

To each well in the split was added single stranded DNA headpiece (1 eq., 1 mM solution in 500 mM pH 9.5 borate buffer), one cycle A tag (1.5 eq.), and splint (1.2 eq.). The chemical ligation was incubated at room temperature overnight. To each well (in the split) was then added one Fmoc amino acid (100 eq.), followed by 4-(4,6-dimethoxy-1,3,5-triazin-2-yl)-4-methylmorpholinium chloride (100 eq.). The chemical reaction was incubated at room temperature overnight. Upon completion, all wells were pooled and the products precipitated using ethanol. The cycle A pool was purified using LC and lyophilized to dryness. Fmoc deprotection was performed on cycle A pool by treating the pool (1 mM in water) with piperidine (10% v/v) for 2 h at room temperature. The deprotected product was precipitated again using ethanol.

Cycle B:

The purified cycle A pool was dissolved in 500 mM, pH 7.0 phosphate buffer to give a 1 mM concentration and then split into separate reaction wells (1 eq. of cycle A product in each well). To each well was added one cycle B protected tag (1.2 eq.), copper (II) acetate (2 eq.), sodium ascorbate (4 eq.), and tris-(benzyltriazolylmethyl)amine (1 eq.). The chemical ligation was incubated at room temperature overnight. Upon completion, the products were precipitated (in the split) using ethanol and then diluted to a 1 mM concentration using 500 mM, pH 9.5 borate buffer. To each well (in the split) was then added a mixture of one formyl acid (100 eq.), diisopropyl carbodiimide (100 eq.), and 1-hydroxy-7-aza-benzotriazole (100 eq.). The chemical reaction was incubated at room temperature overnight. Upon completion, all wells were pooled and the products precipitated using ethanol. The cycle B pool was then dissolved in water to give a 1 mM final concentration, and piperidine (10% v/v) was added to perform the deprotection of cycle B tag (room temperature, 18 h). The deprotected product was precipitated again using ethanol. The deprotected Cycle B pool was purified using LC and lyophilized to dryness.

Cycle C:

The purified cycle B pool was dissolved in 500 mM, pH 5.5 phosphate buffer to give a 1 mM concentration and then split into separate reaction wells (1 eq. of cycle B product in each well). To each well was added one cycle C tag (1.5 eq.) and splint (1.2 eq.). The chemical ligation was incubated at room temperature overnight. To each well (in the split) was added an amine (80 eq.) and sodium cyanoborohydride (80 eq.). The chemical reaction was incubated at 60° C. for 16 h. Upon completion, all wells were pooled and the products precipitated using ethanol. The cycle C pool was purified using LC and lyophilized to dryness.

Other Embodiments

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention.

The invention claimed is:

1. A method of tagging a first library comprising an oligonucleotide-encoded chemical entity, said method comprising:
   (i) providing a single-stranded oligonucleotide headpiece having a first functional group and a second functional group, wherein said headpiece comprises at least one terminal 2'-substituted nucleotide comprising said second functional group, wherein said at least one terminal 2'-substituted nucleotide is at the 5'-terminus and/or the 3'-terminus of said headpiece;
   (ii) binding said first functional group of said headpiece to a first component of said chemical entity, wherein said headpiece is directly connected to said first component or said headpiece is indirectly connected to said first component by a bifunctional linker; and
   (iii) ligating said second functional group of said headpiece to a single-stranded oligonucleotide first building block tag to form a complex, wherein said first building block tag comprises at least one terminal 2'-substituted nucleotide at the 5'- and/or the 3'-terminus and said ligating forms a covalent bond between a 2'-substituted nucleotide on the headpiece and a 2'-substituted nucleotide on the first building block tag, and wherein the ligating is carried out using enzymatic ligation;
   wherein said steps (ii) and (iii) can be performed in any order; and
   wherein said first building block tag encodes for the binding reaction of said step (ii), thereby providing a tagged library.

2. The method of claim 1, wherein said first building block tag further comprises at least one 2'-substituted nucleotide at an internal position.

3. The method of claim 1 or 2, wherein each 2'-substituted nucleotide is, independently, 2'-O-methyl guanine, 2'-O-methyl uracil, 2'-O-methyl adenosine, 2'-O-methyl thymidine, 2'-O-methyl inosine, 2'-O-methyl cytidine, 2'-O-methyl diamino purine, 2'-fluoro guanine, 2'-fluoro uracil, 2'-fluoro adenosine, 2'-fluoro thymidine, 2'-fluoro inosine, 2'-fluoro cytidine, or 2'-fluoro diamino purine.

4. The method of claim 1, wherein step (ii) comprises binding said headpiece directly to said first component.

5. The method of claim 1, wherein step (ii) comprises binding said headpiece indirectly to said first component via a bifunctional linker.

6. The method of claim 1, further comprising
   (iv) binding a single-stranded oligonucleotide second building block tag to the 5'-terminus or 3'-terminus of said complex; and
   (v) binding a second component of said chemical library to said first component, wherein said steps (iv) and (v) can be performed in any order.

7. The method of claim 6, wherein said second building block tag comprises a 2'-substituted nucleotide at one or more of the 5'-terminus, the 3'-terminus, and/or the internal position of said second building block tag.

8. The method of claim 6, wherein said step (iv) is carried out using enzymatic ligation.

9. The method of claim 1 or 6, wherein said method further comprises separating said complex from any unreacted tag or unreacted headpiece before any one of binding steps (ii)-(v) and/or purifying said complex before any one of binding steps (ii)-(v).

10. The method of claim 1, wherein said method further comprises binding one or more additional building block tags to said complex and binding one or more additional components to said complex.

11. The method of claim 1, wherein said headpiece comprises a hairpin structure.

12. The method of claim 1 or 10, wherein said headpiece, said first building block tag, said second building block tag, and/or said one or more additional building block tags, if present, further comprises a first library-identifying sequence, a use sequence, and/or an origin sequence.

13. The method of claim 1, wherein said method further comprises binding a first library-identifying tag, a use sequence, an origin sequence, and/or a tailpiece to said complex.

14. The method of claim 1, wherein said method comprises a plurality of headpieces.

15. The method of claim 1 or 8, wherein said enzymatic ligation is carried out using RNA ligase.

16. The method of claim 15, wherein said RNA ligase is T4 RNA ligase.

17. The method of claim 1 or 8, wherein said enzymatic ligation is carried out using DNA ligase.

18. The method of claim 17, wherein said DNA ligase is ssDNA ligase.

* * * * *

UNITED STATES PATENT AND TRADEMARK OFFICE
CERTIFICATE OF CORRECTION

| | | |
|---|---|---|
| PATENT NO. | : 10,865,409 B2 | Page 1 of 1 |
| APPLICATION NO. | : 14/343306 | |
| DATED | : December 15, 2020 | |
| INVENTOR(S) | : Keefe et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 619 days.

Signed and Sealed this
Seventh Day of February, 2023

Katherine Kelly Vidal
*Director of the United States Patent and Trademark Office*